US009517018B2

(12) United States Patent
Lisogurski et al.

(10) Patent No.: US 9,517,018 B2
(45) Date of Patent: Dec. 13, 2016

(54) METHODS AND SYSTEMS FOR POWER OPTIMIZATION IN A MEDICAL DEVICE

(71) Applicant: Covidien LP, Mansfield, MA (US)

(72) Inventors: Daniel Lisogurski, Boulder, CO (US); Clark R. Baker, Jr., Newman, CA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 15/006,031

(22) Filed: Jan. 25, 2016

(65) Prior Publication Data

US 2016/0135692 A1 May 19, 2016

Related U.S. Application Data

(62) Division of application No. 13/484,711, filed on May 31, 2012, now Pat. No. 9,241,643.

(51) Int. Cl.

| | |
|---|---|
| ***A61B 5/00*** | (2006.01) |
| ***A61B 5/0205*** | (2006.01) |
| ***A61B 5/024*** | (2006.01) |
| ***A61B 5/0402*** | (2006.01) |
| ***A61B 5/1455*** | (2006.01) |

(Continued)

(52) U.S. Cl.

CPC ......... *A61B 5/0205* (2013.01); *A61B 5/02416* (2013.01); *A61B 5/0402* (2013.01); *A61B 5/14551* (2013.01); *A61B 5/14552* (2013.01); *A61B 5/7225* (2013.01); *A61B 5/7292* (2013.01); *A61B 5/0095* (2013.01); *A61B 5/0261* (2013.01); *A61B 5/0295* (2013.01); *A61B 2560/0209* (2013.01)

(58) Field of Classification Search

CPC . A61B 5/021; A61B 5/02416; A61B 5/02433; A61B 5/14551; A61B 5/7285

See application file for complete search history.

(56) References Cited

U.S. PATENT DOCUMENTS

| | | |
|---|---|---|
| 5,343,818 A | 9/1994 | McCarthy et al. |
| 5,349,952 A | 9/1994 | McCarthy et al. |

(Continued)

FOREIGN PATENT DOCUMENTS

| | | |
|---|---|---|
| WO | WO 2006/080856 | 8/2006 |
| WO | WO 2006/083180 | 8/2006 |

OTHER PUBLICATIONS

Takada, H. et al., "Acceleration Plethysmography to Evaluate Aging Effect in Cardiovascular System," Medical Progress Through Technology, vol. 21, pp. 205-210, 1997.

(Continued)

*Primary Examiner* — Mark Remaly

(57) ABSTRACT

A physiological monitoring system may use photonic signals to determine physiological parameters. The system may vary parameters of a light drive signal used to generate the photonic signal from a light source such that power consumption is reduced or optimized. Parameters may include light intensity, firing rate, duty cycle, other suitable parameters, or any combination thereof. In some embodiments, the system may use information from a first light source to generate a light drive signal for a second light source. In some embodiments, the system may vary parameters in a way substantially synchronous with physiological pulses, for example, cardiac pulses. In some embodiments, the system may vary parameters in response to an external trigger.

21 Claims, 30 Drawing Sheets

(51) Int. Cl.

*A61B 5/0295* (2006.01)
*A61B 5/026* (2006.01)

(56) References Cited

U.S. PATENT DOCUMENTS

| | | | | |
|---|---|---|---|---|
| 5,351,685 | A | 10/1994 | Potratz | |
| 5,485,847 | A | 1/1996 | Baker, Jr. | |
| 5,515,847 | A | 5/1996 | Braig et al. | |
| 5,560,355 | A | 10/1996 | Merchant et al. | |
| 5,575,284 | A | 11/1996 | Athan et al. | |
| 5,590,652 | A | 1/1997 | Inai | |
| 5,746,697 | A | 5/1998 | Swedlow et al. | |
| 5,766,127 | A | 6/1998 | Pologe et al. | |
| 5,846,190 | A | 12/1998 | Woehrle | |
| 5,924,979 | A | 7/1999 | Swedlow et al. | |
| 6,005,658 | A | 12/1999 | Kaluza et al. | |
| 6,217,523 | B1 | 4/2001 | Amano et al. | |
| 6,226,539 | B1 | 5/2001 | Potratz | |
| 6,697,655 | B2 | 2/2004 | Sueppel et al. | |
| 6,697,658 | B2 | 2/2004 | Al-Ali | |
| 6,731,967 | B1 | 5/2004 | Turcott | |
| 6,863,652 | B2 * | 3/2005 | Huang ............... | A61B 5/14551 315/224 |
| 6,912,413 | B2 | 6/2005 | Rantala et al. | |
| 7,003,339 | B2 | 2/2006 | Diab et al. | |
| 7,120,479 | B2 | 10/2006 | Chew et al. | |
| 7,162,288 | B2 | 1/2007 | Nordstrom et al. | |
| 7,295,866 | B2 | 11/2007 | Al-Ali | |
| 7,324,848 | B1 | 1/2008 | Turcott | |
| 7,382,247 | B2 | 6/2008 | Welch et al. | |
| 7,623,990 | B2 | 11/2009 | Anderson et al. | |
| 2005/0084202 | A1 | 4/2005 | Smith et al. | |
| 2005/0109339 | A1 | 5/2005 | Stahmann et al. | |
| 2005/0187446 | A1 | 8/2005 | Nordstrom et al. | |
| 2006/0264720 | A1 | 11/2006 | Chew et al. | |
| 2007/0038049 | A1 | 2/2007 | Huang | |
| 2007/0149871 | A1 | 6/2007 | Sarussi et al. | |
| 2007/0208240 | A1 * | 9/2007 | Nordstrom ......... | A61B 5/14551 600/323 |
| 2011/0213397 | A1 | 9/2011 | Mathonnet | |
| 2011/0237911 | A1 | 9/2011 | Lamego et al. | |
| 2011/0237912 | A1 | 9/2011 | Couronne et al. | |
| 2011/0245636 | A1 | 10/2011 | Li et al. | |
| 2012/0116193 | A1 | 5/2012 | Huang | |

OTHER PUBLICATIONS

International Search Report and Written Opinion of the International Searching Authority for application No. PCT/US2013/043338, mailed on Oct. 2, 2013.

EPO Form 1507S, Extended European Search Report and Search Opinion, from the European Patent Office in European Patent Application No. 13797928.2 dated Dec. 17, 2015.

* cited by examiner

METHODS AND SYSTEMS FOR POWER OPTIMIZATION IN A MEDICAL DEVICE

CROSS-REFERENCE TO RELATED APPLICATION

This application is a divisional of U.S. patent application Ser. No. 13/484,711, filed May 31, 2012, which is hereby incorporated by reference herein in its entirety.

SUMMARY

The present disclosure relates to power optimization, and more particularly relates to conserving and optimizing power in a photoplethysmography system or other medical device.

Systems and methods are provided for optimizing power consumption in an optical physiological monitoring system. The system may vary light drive signal parameters to reduce power consumption or vary power use. The system may vary parameters in a technique correlated to cardiac pulse cycles. In some embodiments, reducing power consumption may allow for increased battery life in portable systems or increased portability. In some embodiments, varying light output during a cardiac cycle may reduce heating effects of the emitters. Parameters that may be varied include light intensity, firing rate, duty cycle, other suitable parameters, or any combination thereof. The generated signals may be used to determined physiological parameters such as blood oxygen saturation, hemoglobin, blood pressure, pulse rate, other suitable parameters, or any combination thereof.

In some embodiments, the system may use information from a first light source to control a second light source. The system may generate a first light drive signal for activating a first light source to emit a first photonic signal. The first light source and second light source may each include one or more emitters. The system may receive a light signal attenuated by the subject, wherein the light signal comprises a component corresponding to the first photonic signal. The system may analyze the component of the light signal to determine when to activate a second light source. The system may generate a second light drive signal, based on the analysis of the first component, for activating the second light source to emit one or more second photonic signals. The system may determine one or more physiological parameters based on the light signals.

In some embodiments, the system may vary a light drive signal in a way substantially synchronous with physiological pulses, for example, cardiac pulses. The system may generate a light drive signal for activating a light source to emit a photonic signal, wherein at least one parameter of the light drive signal is configured to vary substantially synchronously with physiological pulses of the subject. The system may receive a light signal attenuated by the subject, wherein the signal comprises a component corresponding to the emitted photonic signal. The system may determine physiological parameters based on the signal. In some embodiments, the system may vary light levels with other periodic (or mostly periodic) physiological changes. For example, venous return changes with intrathoracic pressure during a respiration cycle can affect the baseline level of the photoplethysmography waveform. The system may vary the emitter output such that similar signal quality is available at the detector over time varying volumes of venous blood present in the path of light.

In some embodiments, the system may vary a light drive signal based on a received external trigger. The system may receive an external trigger based on a signal other than a light signal received by the physiological monitor. The trigger may include a signal received from an ECG sensor, an ECG sensor configured to detect an R-wave, a blood pressure sensor, a respiration rate sensor, any other suitable sensor, or any combination thereof. The system may, in response to the external trigger, vary the light intensity, duty cycle, light source firing rate, any other suitable parameter, or any combination thereof.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
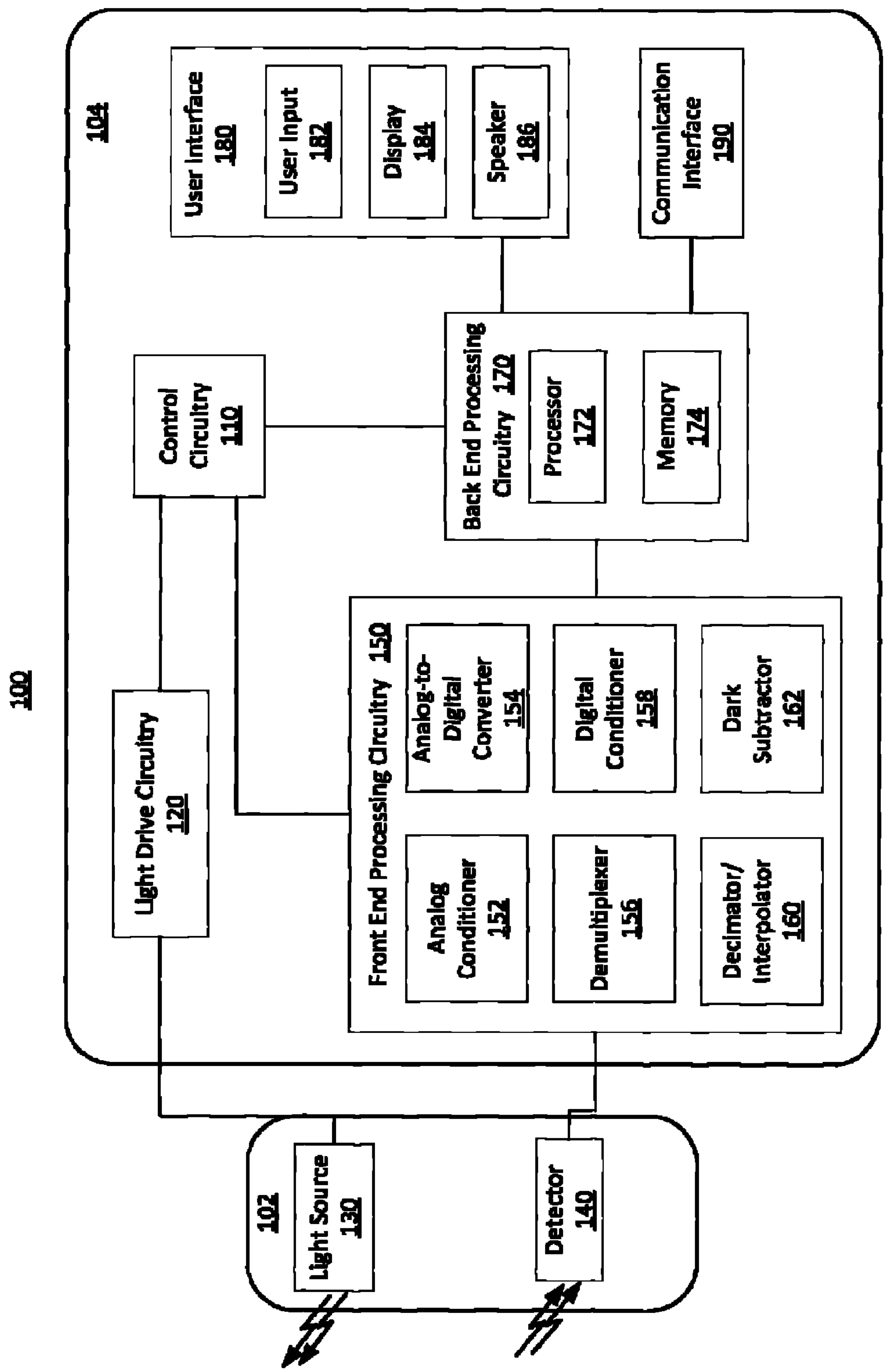
FIG. 1 is a block diagram of an illustrative physiological monitoring system in accordance with some embodiments of the present disclosure.

The present disclosure is directed towards power optimization in a medical device. A physiological monitoring system may monitor one or more physiological parameters of a patient, typically using one or more physiological sensors. The system may include, for example, a light source and a photosensitive detector. Providing a light drive signal to the light source may account for a significant portion of the system's total power consumption. Thus, it may be desirable to reduce the power consumption of the light source, while still enabling high quality physiological parameters to be determined. The system may reduce the power consumption by modulating parameters associated with the light drive signal in techniques correlated to the cardiac cycle or other cyclical physiological activity. For example, the system may decrease brightness during a particular portion of the cardiac cycle. It may also be desirable to reduce the power consumption by the light drive signal to reduce heating effects caused by an emitter.

An oximeter is a medical device that may determine the oxygen saturation of an analyzed tissue. One common type of oximeter is a pulse oximeter, which may non-invasively measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate and blood pressure.

An oximeter may include a light sensor that is placed at a site on a patient, typically a fingertip, toe, forehead or earlobe, or in the case of a neonate, across a foot. The oximeter may use a light source to pass light through blood perfused tissue and photoelectrically sense the absorption of the light in the tissue. In addition, locations which are not typically understood to be optimal for pulse oximetry serve as suitable sensor locations for the blood pressure monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a logarithm taken thereof, a scaled version of a logarithm taken thereof, a derivative taken thereof, a difference taken thereof, etc.) may be referred to as the photoplethysmograph (PPG) signal. In addition, the term "PPG signal," as used herein, may also refer to an absorption signal (i.e., representing the amount of light absorbed by the tissue), a transmission signal (i.e., representing the amount of light received from the tissue), any suitable mathematical manipulation thereof, or any combination thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the photonic signal interacting with the tissue is selected to be of one or more wavelengths that are attenuated by the blood in an amount representative of the blood constituent concentration. Red and infrared (IR) wavelengths may be used because it has been observed that highly oxygenated blood will absorb relatively less red light and more IR light than blood with a lower oxygen saturation. By comparing the intensities of two wavelengths at different points in the pulse cycle, it is possible to estimate the blood oxygen saturation of hemoglobin in arterial blood.

The system may process data to determine physiological parameters using techniques well known in the art. For example, the system may determine blood oxygen saturation using two wavelengths of light and a ratio-of-ratios calculation. The system also may identify pulses and determine pulse amplitude, respiration, blood pressure, other suitable parameters, or any combination thereof, using any suitable calculation techniques. In some embodiments, the system may use information from external sources (e.g., tabulated data, secondary sensor devices) to determine physiological parameters.

In some embodiments, it may be desirable to implement techniques to optimize power consumption in an oximeter or other system. For example, in a battery powered system, reducing the power requirements may allow for smaller devices, longer life, or both. In some embodiments, powering the light source may include a large amount of the power load a device may experience. In some embodiments, variation of parameters in the light drive signal may enable a particular amount of power to be used more efficiently. For example, the brightness of a light source may be decreased during a less important period and increased during a more important period. In some embodiments, parameter variation may reduce the impact of heating effects caused by a light source on a subject. Techniques to vary the amount of time a light source is turned on, to vary the brightness of the light source, other techniques, or any combination thereof, may be employed to modify power consumption.

In some embodiments, the brightness of one of more light sources may be modulated in a technique that is related to the cardiac cycle. The cardiac cycle is the substantially periodic repetition of events that occur, for example, during heartbeats. The cardiac cycle may include a systole period and diastole period. The cardiac cycle may include pressure changes in the ventricles, pressure changes in the atria, volume changes in the ventricles, volume changes in the atria, opening and closing of heart valves, heart sounds, and other cyclic events. In some embodiments, the heart may enter a non-periodic state, for example, in certain types of arrhythmia and fibrillation.

As used herein, "cardiac cycle modulation" will refer to the modulation techniques generally correlated to the cardiac cycle. It will be understood that cardiac cycle modulation may include modulation aligned with pulses of the heart, pulses of a particular muscle group, other suitable pulses, any other suitable physiological cyclical function, or any combination thereof. In some embodiments, the system may use a cardiac cycle modulation with a period on the order of the cardiac cycle period. For example, the cardiac cycle modulation may repeat every cardiac cycle. In some embodiments, the system may use a cardiac cycle modulation with a period on the order of some multiple of the cardiac cycle period. For example, the cardiac cycle modulation may repeat every three cardiac cycles. In some embodiments, the cardiac cycle modulation may relate to both a cardiac cycle and a respiratory cycle. The cardiac cycle and the respiratory cycle may have a time varying phase relationship. It will be understood that cardiac cycle modulation techniques, while generally related to the cardiac cycle, may not necessarily be precisely correlated to the cardiac cycle and may be related to predetermined parameters, other physiological parameters, other physiological cycles, external triggers (e.g., respiration), user input, other suitable techniques, or any combination thereof.

As used herein, "drive cycle modulation" (described below) will refer to a relatively higher frequency modulation technique that the system may use to generate one or more wavelengths of intensity signals. Cardiac cycle modulation may have a period of, for example, around 1 second, while drive cycle modulation may have a period around, for example, 1.6 milliseconds.

In some embodiments, conventional servo algorithms may be used in addition to any combination of cardiac cycle modulation and drive cycle modulation. Conventional servo algorithms may adjust the light drive signals due to, for example, ambient light changes, emitter and detector spacing changes, sensor positioning, other suitable parameters, or any combination thereof. Generally, conventional servo algorithms vary parameters at a slower rate than cardiac cycle modulation. For example, a conventional servo algorithm may adjust drive signal brightness due to ambient light every several seconds. The system may use conventional servo algorithms in part to keep received signal levels within the range of an analog to digital converter's dynamic range. For example, a signal with amplitudes that are large may saturate an analog to digital convertor. In response to a signal with high amplitudes, the system may reduce emitter brightness. In a further example, the quality of a low amplitude signal may be degraded by quantization noise by an analog to digital converter. In response, the system may increase the emitter brightness.

In some embodiments, a technique to remove ambient and background signals may be used in addition to or in place of a power saving light modulation scheme. In a drive cycle modulation technique, the system may cycle light output at a rate significantly greater than the cardiac cycle. For example, a drive cycle modulation cycle may include the system turning on a first light source, followed by a "dark" period, followed by a second light source, followed by a "dark" period. The system may measure the ambient light detected by the detector during the "dark" period and then subtract this ambient contribution from the signals received during the first and second "on" periods. In some embodiments, drive cycle modulation may be implemented using time division multiplexing as described above, code division multiplexing, carrier frequency multiplexing, phase division multiplexing, feedback circuitry, DC restoration circuitry, any other suitable technique, or any combination thereof. For example, the system may use frequency division multiplexing in a drive cycle modulation technique. The cardiac cycle modulation may represent a lower frequency envelope function on the higher frequency drive cycle. For example, cardiac cycle modulation may be an envelope on the order of 1 Hz superimposed on a 1 kHz sine wave drive cycle modulation.

In some embodiments, the system may use various cardiac cycle modulation schemes to adjust the brightness of a light source controlled by the light drive signal used in determining physiological parameters. The system may modulate the brightness of the light source using a periodic waveform, for example, a sinusoidal or triangle wave. The period of the waveform may be substantially related to the cardiac pulse rate, for example, in a one-to-one relationship, a two-to-one relationship, any other suitable relationship, or any suitable combination thereof. The system may align the peak of the modulated light drive signal with a particular point in the cardiac cycle to improve the quality of the determined physiological parameter, for example, it may be aligned with the diastolic period, the systolic period, the dicrotic notch, any other suitable point, or any combination thereof. In some embodiments, the system may modulate the light drive signal with a square wave function, such that it is at a low brightness level during a first part of the cardiac cycle and a high brightness level during a second part of the cardiac cycle. In some embodiments, the low brightness level may include turning one or more light sources off.

In some embodiments, the cardiac cycle modulation technique may be selected or varied, for example, based on empirical data. The system may determine or vary the phase relationship of a cardiac cycle modulation based on the determined physiological parameter. For example, the system may vary the timing of a cardiac cycle modulation technique to determine pulse identification based on a metric related to the determined pulse, such as a standard deviation. In another example, data points may be analyzed to determine if a cardiac pulse peak is aligned with a cardiac cycle modulation maximum, and the system may make phase relationship adjustments accordingly. In some embodiments, more complex variation algorithms may be used depending on the determined physiological parameter. Selections and variations of cardiac cycle modulation techniques may also be based on empirical data, user input, lookup tables, historical information, other suitable information or any combination thereof.

In some embodiments, the system may combine cardiac cycle modulation techniques. For example, the system may use a first cardiac cycle modulation technique during a first pulse cycle and a second cardiac cycle modulation technique during a second pulse cycle. More complex selections, alterations, overlapping, and convolving of cardiac cycle modulation techniques may be used depending, in part, on the determined physiological parameter or parameters.

In some embodiments, the system may correct for non-linearity of light sources. For example, the emitted intensity of light from an LED may not vary linearly with the drive current. The system may account for non-linearity by adjusting drive signals, by adjusting amplification of received signal gain, by adjusting received signal processing, by any other suitable method, or any combination thereof. For example, the system may adjust the drive signal to an LED to improve the linearity. Corrections may be determined using a calibration step, lookup tables for known components, empirical data, any other suitable techniques, or any combination thereof. For example, the emission intensity relative to a drive signal may be known for a particular LED. Information may be encoded in a calibration resistor or non-volatile calibration memory included in the sensor or the system. In another example, the system may calibrate emission output by comparing the intensity of received signals generated in response to a high current drive signal with those generated in response to a low current drive signal. In some embodiments, the operating range of a component (e.g., an LED) may be limited. In some embodiments, a component may operate with a linear relationship between drive signal and output intensity within a known range of drive signals, and in a non-linear relationship outside that range of drive signals.

In some embodiments of cardiac cycle modulation, the system may modulate multiple light sources using a plurality of modulation techniques. For example, in a system with two light sources, the system may operate a first light source at full or regular brightness, while operating one or more additional light sources in a switched or otherwise modulated mode. In some embodiments, the system may operate a first light source according to a first cardiac cycle modulation technique and a second light source according to a second cardiac modulation technique. The first and second cardiac cycle modulation techniques may be the same, correlated, or unrelated. In some embodiments, the system may use the first light source to determine periods of interest in the cardiac cycle. The system may, according to the periods of interest, power additional light sources, alter the modulation of the additional light sources, perform other suitable power optimization techniques, or any combination thereof. In some embodiments, the system may include a first light source (e.g., a light source powered at full or regular brightness) of a type that is a more efficient light source than the one or more additional light sources. For example, the first light source may be a high efficiency infrared (IR) LED while the one or more additional light sources may be lower efficiency red LEDs or laser diodes. In some embodiments, the first light source may be selected based on efficiency parameters and information from the first light source may be used only to control a second light source. For example, a highly efficient first light source that is not at a wavelength of interest for physiological parameter determination may be used to control one or more second light sources at wavelengths of interest. In this case, the light from the first light source may be used only for controlling the second light source and not for determining physiological parameters.

In some embodiments, the system may use the first light source to determine a pulse rate or identify elements of the cardiac cycle, and the system may use the pulse rate or identified elements in part to control modulation of the light drive signal. Identified elements may include peaks, valleys, troughs, notches, fiducial points, other suitable elements, or any combination thereof. Fiducial points may be related to the zero crossings of first and higher order derivatives of the waveform. In some embodiments, the system may modulate the first light drive signal according to a first cardiac cycle modulation technique and may modulate the one or more additional light drive signal according to a second cardiac cycle modulation technique. For example, the system may operate the first light source at full or regular brightness for a first "on" period, and then "off" for a second period. The system may use the first "on" period to adjust or calibrate a second modulation technique. The system may implement the second modulation technique for the "off" period, using, for example, one or more light sources that may or may not include the first light source. As described above, this cardiac cycle modulation may be implemented in addition to a drive cycle modulation, conventional servo algorithms, or any combination thereof.

As used herein, the terms "on" and "off" are merely exemplary and may not necessarily refer to a fully on or off state. For example, "on" and "off" may refer to switching power or other components, high and low brightness output states, high and low values within a continuous modulation, high and low values of electrical current provided to an emitter, high and low values of a duty cycle, high and low values of a decimation ratio (i.e., how often an emitter is switched on), any other suitable relatively distinct states, or any combination thereof. In some embodiments, "on" and "off" states may relate to high and low values of a variable that varies with multiple discrete steps. For example, an emitter brightness may be provided by the system as off, low, medium, and high. In this example, an "off" state may refer to off or low emission and "on" may refer to medium or high. In another example, "off" may refer to an off state and "on" may refer to a low, medium, or high output depending on a second input or system variable.

In some embodiments, historical information may be used to determine the timing of cardiac cycle modulation. For example, information from previous pulse cycles may be used to determine "on" and "off" states. In some embodiments, the system may use statistical information from historical information, for example, mean period and/or standard deviation of one or more previous pulse cycles. The system may use a mean period to determine or estimate the time period between a previous period of interest and the next period of interest. For example, the system may wait a particular percentage (e.g., 80%) of the mean period following a period of interest before returning to an "on" state. In some embodiments, the particular percentage or other criteria may be based on statistical information. For example, a smaller standard deviation in the period of historical pulses may indicate that there is relatively less variation in the pulse period. The system may increase the amount of time it waits before turning a drive signal back to an "on" state, as the confidence of the position in time of the next period of interest is high. Similarly, the system may reduce the waiting period in response to a relatively high standard deviation in the period of historical pulses. For example, the system may identify a relatively high standard deviation in the period of historical pulses when a significant respiratory sinus arrhythmia is present. In some embodiments, the system may remain in a particular cardiac cycle modulation mode for an amount of time following a historical event. For example, the system may operate in a high power mode without cardiac cycle modulation for a certain time period following, for example, high noise levels, a loss of signal, or an irregular cardiac rhythm. In some embodiments, the system may use a cardiac cycle modulation during periodic abnormal rhythms such as a 2nd degree AC block, bundle branch block, or sustained ventricular tachycardia.

The system may use one or more cardiac cycle modulation techniques depending on the desired physiological parameter. In some embodiments, the system may emit light at a relatively higher brightness level during a diastole period when the desired physiological parameter is pulse identification. In some embodiments, the system may emit light at a relatively higher brightness level during a systole period when the desired physiological parameter is a quantification of pulse amplitude variability. In some embodiments, the system may emit light at a relatively higher brightness level during a systole period when the desired physiological parameter is blood oxygen saturation calculated using a ratio-of-ratios calculation. In some embodiments, the system may require sampling an accurate time and amplitude for the peak and foot of a pulse and less accurate sampling of the rising or falling waveform, and may modulate the emitted light accordingly. In some embodiments, the system may emit light at a relatively higher level at a time in the cardiac cycle correlated with dicrotic notches, fiducial points, or other points of interest. Fiducial points may include, for example, local maxima, local minima, points related to the zero crossings of first and higher order derivatives, other points of interest, or any combination thereof.

In some embodiments, the system may vary the algorithm used to determine a physiological parameter based, in part, on the cardiac cycle modulation technique. For example, if a cardiac cycle modulation technique only detects the peaks and valleys of a pulse cycle, a first type of blood oxygen saturation algorithm may be used (e.g., discrete oximetry based only on the peak and valley information). If the cardiac cycle modulation technique detects the entire pulse, a different blood oxygen saturation detection algorithm may be used (e.g., a regression based algorithm).

In some embodiments, the system may alter the cardiac cycle modulation technique based on the level of noise, ambient light, other suitable reasons, or any combination thereof. The system may receive, for example, an increased level of background noise in the signal due to patient motion. The system may increase the brightness of the light sources in response to the noise to improve the signal-to-noise ratio. In some embodiments, the system may increase brightness throughout the cardiac cycle because the system may require increased signal amplitudes to differentiate between fiducial and other points of interest related to physiological parameters and those related to noise or motion. In some embodiments, the system may change from a modulated light output to a constant light output in response to noise, patient motion, or ambient light.

In some embodiments, the system may alter the cardiac cycle modulation technique based on a determined physiological condition. For example, the system may detect non-periodic cardiac behavior (e.g., arrhythmia, fibrillation, or asystole) and change the modulation technique from a modulated light output to a constant light output. It will be understood that pulseless electrical activity, asystole, and/or other electrical arrhythmias may result in ECG activity but not result in detectable pulsatile activity.

In some embodiments, the system may use external triggering to control or modify a cardiac cycle modulation technique. For example, the system may use information from a second sensor such as an ECG sensor, invasive blood pressure sensor, a second pulse oximeter, a second photoplethysmography sensor, a pulse meter, a respiration sensor, any other suitable sensor, or any combination thereof. For example, the external signal may be received from an external ECG sensor configured to provide a trigger signal synchronous with an element of the cardiac cycle such as an R wave. In some embodiments, the system may receive an external trigger from user input or an external processing device. In some embodiments, the system may correlate a cardiac cycle modulation with one or more particular points in an ECG signal. In some embodiments, the system may use an algorithm to determine the delay between the external signal and points of interest. For example, the system may use an algorithm to determine a delay between an ECG R-wave and the fiducial points of interest in a photoplethysmography signal such as the peak of the PPG waveform.

In some embodiments, the system may optimize power consumption by varying a sampling rate. The system may digitize a received signal using an analog to digital converter operating at a particular rate. In some embodiments, the digitizer rate may be constant. In some embodiments, the digitizer rate may be modulated using a technique correlated to a cardiac cycle modulation. For example, the system may sample at a high rate during a period of interest and at a low rate during other periods. In some embodiments, the system may modulate both a light drive signal and a sampling rate. The modulations of the light drive signal and the sampling rate may be correlated. For example, the system may sample the received signal at a low rate during a period of low light output and at a high rate during a period of high light output. The system may decimate or interpolate the digitized signal such that the rate of the processed signal is constant.

The following description and accompanying FIGS. 1-28 provide additional details and features of some embodiments of power optimization in a medical device.

FIG. 1 is a block diagram of an illustrative physiological monitoring system 100 in accordance with some embodiments of the present disclosure. System 100 may include a sensor 102 and a monitor 104 for generating and processing physiological signals of a subject. In some embodiments, sensor 102 and monitor 104 may be part of an oximeter.

Sensor 102 of physiological monitoring system 100 may include light source 130 and detector 140. Light source 130 may be configured to emit photonic signals having one or more wavelengths of light (e.g., Red and IR) into a subject's tissue. For example, light source 130 may include a Red light emitting light source and an IR light emitting light source, e.g., Red and IR light emitting diodes (LEDs), for emitting light into the tissue of a subject to generate physiological signals. In one embodiment, the Red wavelength may be between about 600 nm and about 700 nm, and the IR wavelength may be between about 800 nm and about 1000 nm. It will be understood that light source 130 may include any number of light sources with any suitable characteristics. In embodiments where an array of sensors is used in place of single sensor 102, each sensor may be configured to emit a single wavelength. For example, a first sensor may emit only a Red light while a second may emit only an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 140 may be chosen to be specifically sensitive to the chosen targeted energy spectrum of light source 130.

In some embodiments, detector 140 may be configured to detect the intensity of light at the Red and IR wavelengths. In some embodiments, an array of sensors may be used and each sensor in the array may be configured to detect an intensity of a single wavelength. In operation, light may enter detector 140 after passing through the subject's tissue. Detector 140 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detector 140. After converting the received light to an electrical signal, detector 140 may send the detection signal to monitor 104, where the detection signal may be processed and physiological parameters may be determined (e.g., based on the absorption of the Red and IR wavelengths in the subject's tissue). In some embodiments, the detection signal may be preprocessed by sensor 102 before being transmitted to monitor 104.

In the embodiment shown, monitor 104 includes control circuitry 110, light drive circuitry 120, front end processing circuitry 150, back end processing circuitry 170, user interface 180, and communication interface 190. Monitor 104 may be communicatively coupled to sensor 102.

Control circuitry 120 may be coupled to light drive circuitry 120, front end processing circuitry 150, and back end processing circuitry 170, and may be configured to control the operation of these components. In some embodiments, control circuitry 110 may be configured to provide timing control signals to coordinate their operation. For example, light drive circuitry 120 may generate a light drive signal, which may be used to turn on and off the light source 130, based on the timing control signals. The front end processing circuitry 150 may use the timing control signals to operate synchronously with light drive circuitry 120. For example, front end processing circuitry 150 may synchronize the operation of an analog-to-digital converter and a demultiplexer with the light drive signal based on the timing control signals. In addition, the back end processing circuitry 170 may use the timing control signals to coordinate its operation with front end processing circuitry 150.

Light drive circuitry 110, as discussed above, may be configured to generate a light drive signal that is provided to light source 130 of sensor 102. The light drive signal may, for example, control the intensity of light source 130 and the timing of when light source 130 is turned on and off. When light source 130 is configured to emit two or more wavelengths of light, the light drive signal may be configured to control the operation of each wavelength of light. The light drive signal may comprise a single signal or may comprise multiple signals (e.g., one signal for each wavelength of light). An illustrative light drive signal is shown in FIG. 2A.

Figure 2A:
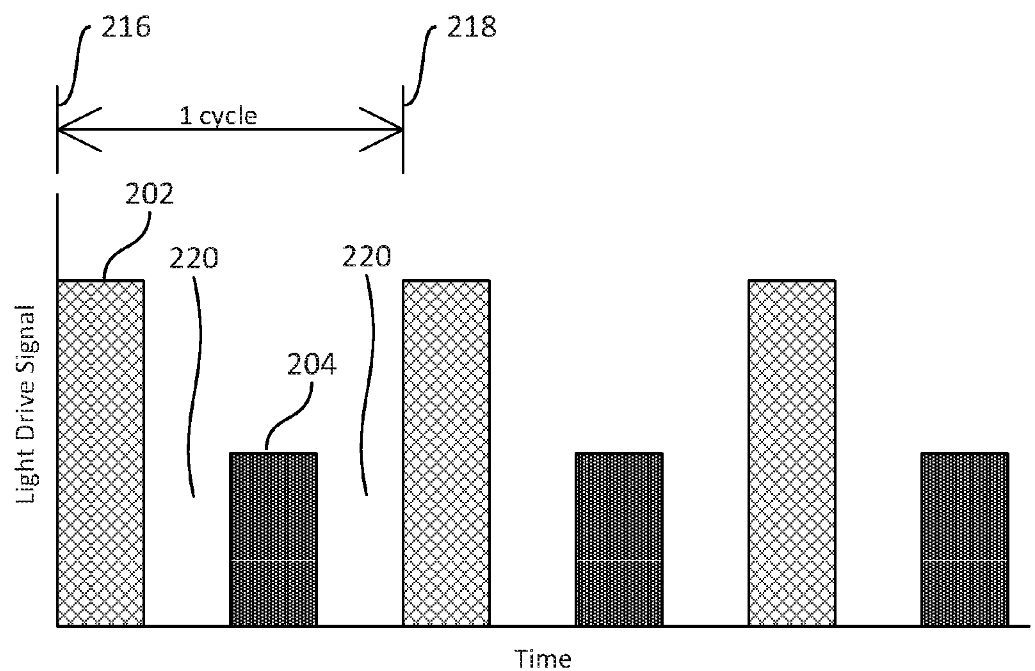
FIG. 2A shows an illustrative plot of a light drive signal in accordance with some embodiments of the present disclosure.

FIG. 2A shows an illustrative plot of a light drive signal including red light "on" period 202 and IR light "on period" 204 in accordance with some embodiments of the present disclosure. Light "on" periods 202, and 204 may be generated by light drive circuitry 120 under the control of control circuitry 110. As used herein, "on" and "off" may refer to switching power or other components, high and low output states, high and low values within a continuous modulation, high and low duty cycles, other suitable relatively distinct states, or any combination thereof. The light drive signal may be provided to light source 130, including red "on" period 202 and IR "on" period 204 to drive red and IR light emitters, respectively, within light source 130. Red "on" period 202 may have a higher amplitude than IR "on" period 204 since red LEDs may be less efficient than IR LEDs at converting electrical energy into light energy. Additionally, red light may be absorbed and scattered more than IR light when passing through perfused tissue at certain oxygen saturations. When the red and IR light sources are driven in this manner they emit pulses of light at their respective wavelengths into the tissue of a subject in order generate physiological signals that physiological monitoring system 100 may process to calculate physiological parameters. It will be understood that the light drive amplitudes of FIG. 2A are merely exemplary, and that any suitable amplitudes or combination of amplitudes may be used, and may be based on the light sources, the subject tissue, the determined physiological parameter, modulation techniques, power sources, any other suitable criteria, or any combination thereof.

The light drive signal of FIG. 2A may also include "off" periods 220 between the Red and IR light "on" periods. "Off" periods 220 are periods during which no drive current may be applied to light source 130. "Off" periods 220 may be provided, for example, to prevent overlap of the emitted light, since light source 130 may require time to turn completely on and completely off. The period from time 216 to time 218 may be referred to as a drive cycle, which includes four segments: a Red light "on" periods 202, followed by an "off" period 220, followed by an IR light "on" period 204, and followed by an "off" period 220. After time 218 the drive cycle may be repeated (e.g., as long as a light drive signal is provided to light source 130). It will be understood that the starting point of the drive cycle is merely illustrative and that the drive cycle can start at any location within FIG. 2A, provided the cycle spans two light "on" periods and two "off" periods. Thus, each Red light "on" period 202 and each IR "on" period 204 may be understood to be surrounded by two dark periods 220.

Referring back to FIG. 1, front end processing circuitry 150 may receive a detection signal from detector 140 and provide one or more processed signals to back end processing circuitry 170. The term "detection signal," as used herein, may refer to any of the signals generated within front end processing circuitry 150 as it processes the output signal of detector 140. Front end processing circuitry 150 may perform various analog and digital processing of the detector signal. One suitable detector signal that may be received by front end processing circuitry 150 is shown in FIG. 2B.

Figure 2B:
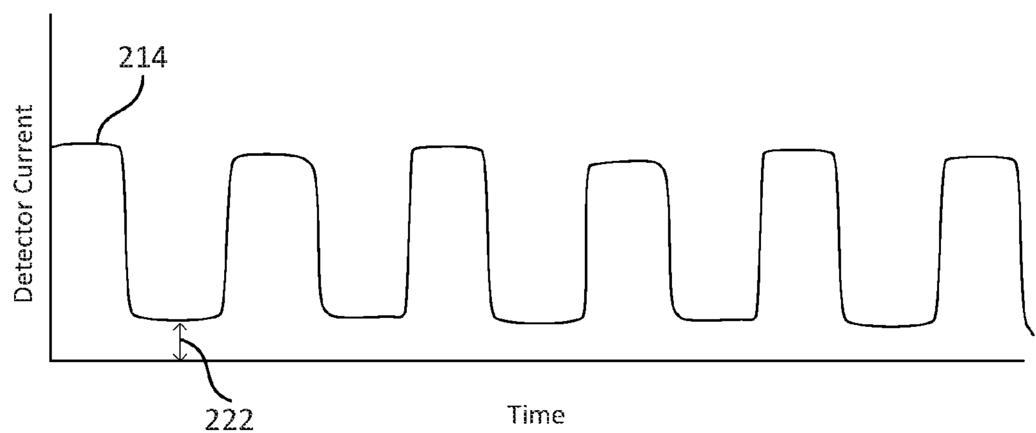
FIG. 2B shows an illustrative plot of a detector signal that may be generated by a sensor in accordance with some embodiments of the present disclosure.

FIG. 2B shows an illustrative plot of detector signal 214 that may be generated by a sensor in accordance with some embodiments of the present disclosure. The peaks of detector current waveform 214 may represent current signals provided by a detector, such as detector 140 of FIG. 1, when light is being emitted from a light source. The amplitude of detector current waveform 214 may be proportional to the light incident upon the detector. The peaks of detector current waveform 214 may be synchronous with light "on" periods driving one or more emitters of a light source, such as light source 130 of FIG. 1. For example, detector current waveform 214 may be generated in response to a light source being driven by the light drive signal of FIG. 2A. The valleys of detector current waveform 214 may be synchronous with periods of time during which no light is being emitted by the light source. While no light is being emitted by a light source during the valleys, detector current waveform 214 may not fall all of the way to zero. Rather, dark current 222 may be present in the detector waveform. Since dark current 222 may interfere with accurate determinations of physiological characteristics, dark current 222 may be removed as discussed in more detail below.

Referring back to FIG. 1, front end processing circuitry 150, which may receive a detection signal, such as detector current waveform 214, may include analog conditioner 152, analog-to-digital converter 154, demultiplexer 156, digital conditioner 158, decimator/interpolator 160, and dark subtractor 162.

Analog conditioner 152 may perform any suitable analog conditioning of the detector signal. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof.

The conditioned analog signal may be processed by analog-to-digital converter 154, which may convert the conditioned analog signal into a digital signal. Analog-to-digital converter 154 may operate under the control of control circuitry 110. Analog-to-digital converter 154 may use timing control signals from control circuitry 110 to determine when to sample the analog signal. Analog-to-digital converter 154 may be any suitable type of analog-to-digital converter of sufficient resolution to enable a physiological monitor to accurately determine physiological parameters.

Demultiplexer 156 may operate on the analog or digital form of the detector signal to separate out different components of the signal. For example, detector current waveform 214 of FIG. 2B includes a Red component, an IR component, and at least one dark component. Demultiplexer 156 may operate on detector current waveform 214 of FIG. 2B to generate a Red signal, an IR signal, a first dark signal (e.g., corresponding to the dark component that occurs immediately after the Red component), and a second dark signal (e.g., corresponding to the dark component that occurs immediately after the IR component). Demultiplexer 156 may operate under the control of control circuitry 110. For example, demultiplexer 156 may use timing control signals from control circuitry 110 to identify and separate out the different components of the detector signal.

Digital conditioner 158 may perform any suitable digital conditioning of the detector signal. The digital conditioner may include any type of digital filtering of the signal (e.g., low pass, high pass, band pass, notch, or any other suitable filtering), amplifying, performing an operation on the signal, performing any other suitable digital conditioning, or any combination thereof.

Decimator/interpolator 160 may decrease the number of samples in the digital detector signal. For example, decimator/interpolator 160 may decrease the number of samples by removing samples from the detector signal or replacing samples with a smaller number of samples. The decimation or interpolation operation may include or be followed by filtering to smooth the output signal.

Dark subtractor 162 may operate on the digital signal. In some embodiments, dark subtractor 162 may subtract dark values from the Red and IR components to generate adjusted Red and IR signals. For example, dark subtractor 162 may determine a subtraction amount from the dark signal portion of the detection signal and subtract it from the peak portion of the detection signal in order to reduce the effect of the dark signal on the peak. For example, in reference to FIG. 2A, a detection signal peak corresponding to red "on" period 202 may be adjusted by determining the amount of dark signal during the "off" period 220 preceding red "on" period 202. The dark signal amount determined in this manner may be subtracted from the detector peak corresponding to red "on" period 202. Alternatively, the "off" period 220 after red "on" period 202 may be used to correct red "on" period 202 rather than the "off" period 220 preceding it. Additionally, an average of the "off" periods 220 before and after red "on" period 202 may be used.

The components of front end processing circuitry 150 are merely illustrative and any suitable components and combinations of components may be used to perform the front end processing operations.

The front end processing circuitry 150 may be configured to take advantage of the full dynamic range of analog-to-digital converter 154. This may be achieved by applying gain to the detection signal by analog conditioner 152 to map the expected range of the detection signal to the full or close to full output range of analog-to-digital converter 154. The output value of analog-to-digital converter 154, as a function of the total analog gain applied to the detection signal, may be given as:

$$\text{ADC Value} \propto \text{Total Analog Gain} \times [\text{Ambient Light} + \text{LED Light}].$$

Ideally, when ambient light is zero and when the light source is off, the analog-to-digital converter 154 will read just above the minimum input value. When the light source is on, the total analog gain may be set such that the output of analog-to-digital converter 154 may read close to the full scale of analog-to-digital converter 154 without saturating. This may allow the full dynamic range of analog-to-digital converter 154 to be used for representing the detection signal, thereby increasing the resolution of the converted signal. In some embodiments, the total analog gain may be reduced by a small amount so that small changes in the light level incident on the detector do not cause saturation of analog-to-digital converter 154.

However, if the contribution of ambient light is large relative to the contribution of light from a light source, the total analog gain applied to the detection current may need to be reduced to avoid saturating analog-to-digital converter 154. When the analog gain is reduced, the portion of the signal corresponding to the light source may map to a smaller number of analog-to-digital conversion bits. Thus, more ambient light noise in the input of analog-to-digital converter 154 may results in fewer bits of resolution for the portion of the signal from the light source. This may have a detrimental effect on the signal-to-noise ratio of the detection signal. Accordingly, passive or active filtering or signal modification techniques may be employed to reduce the effect of ambient light on the detection signal that is applied to analog-to-digital converter 154, and thereby reduce the contribution of the noise component to the converted digital signal.

Back end processing circuitry 170 may include processor 172 and memory 174. Processor 172 may be adapted to execute software, which may include an operating system and one or more applications, as part of performing the functions described herein. Processor 172 may receive and process physiological signals received from front end processing circuitry 150. For example, processor 172 may determine one or more physiological parameters based on the received physiological signals. Memory 174 may include any suitable computer-readable media capable of storing information that can be interpreted by processor 172. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. Back end processing circuitry 170 may be communicatively coupled with use interface 180 and communication interface 190.

User interface 180 may include user input 182, display 184, and speaker 186. User input 182 may include any type of user input device such as a keyboard, a mouse, a touch screen, buttons, switches, a microphone, a joy stick, a touch pad, or any other suitable input device. The inputs received by user input 182 can include information about the subject, such as age, weight, height, diagnosis, medications, treatments, and so forth. In an embodiment, the subject may be a medical patient and display 184 may exhibit a list of values which may generally apply to the patient, such as, for example, age ranges or medication families, which the user may select using user input 182. Additionally, display 184 may display, for example, an estimate of a subject's blood oxygen saturation generated by monitor 104 (referred to as an "$SpO_2$" measurement), pulse rate information, respiration rate information, blood pressure, any other parameters, and any combination thereof. Display 184 may include any type of display such as a cathode ray tube display, a flat panel display such a liquid crystal display or plasma display, or any other suitable display device. Speaker 186 within user interface 180 may provide an audible sound that may be used in various embodiments, such as for example, sounding an audible alarm in the event that a patient's physiological parameters are not within a predefined normal range.

Communication interface 190 may enable monitor 104 to exchange information with external devices. Communications interface 190 may include any suitable hardware, software, or both, which may allow monitor 104 to communicate with electronic circuitry, a device, a network, a server or other workstations, a display, or any combination thereof. Communications interface 190 may include one or more receivers, transmitters, transceivers, antennas, plug-in connectors, ports, communications buses, communications protocols, device identification protocols, any other suitable hardware or software, or any combination thereof. Communications interface 190 may be configured to allow wired communication (e.g., using USB, RS-232 or other standards), wireless communication (e.g., using WiFi, IR, WiMax, BLUETOOTH, UWB, or other standards), or both. For example, communications interface 190 may be configured using a universal serial bus (USB) protocol (e.g., USB 2.0, USB 3.0), and may be configured to couple to other devices (e.g., remote memory devices storing templates) using a four-pin USB standard Type-A connector (e.g., plug and/or socket) and cable. In some embodiments, communications interface 190 may include an internal bus such as, for example, one or more slots for insertion of expansion cards.

It will be understood that the components of physiological monitoring system 100 that are shown and described as separate components are shown and described as such for illustrative purposes only. In some embodiments the functionality of some of the components may be combined in a single component. For example, the functionality of front end processing circuitry 150 and back end processing circuitry 170 may be combined in a single processor system. Additionally, in some embodiments the functionality of some of the components of monitor 104 shown and described herein may be divided over multiple components. For example, some or all of the functionality of control circuitry 110 may be performed in front end processing circuitry 150, in back end processing circuitry 170, or both. In other embodiments, the functionality of one or more of the components may be performed in a different order or may not be required. In an embodiment, all of the components of physiological monitoring system 100 can be realized in processor circuitry.

Figure 2C:
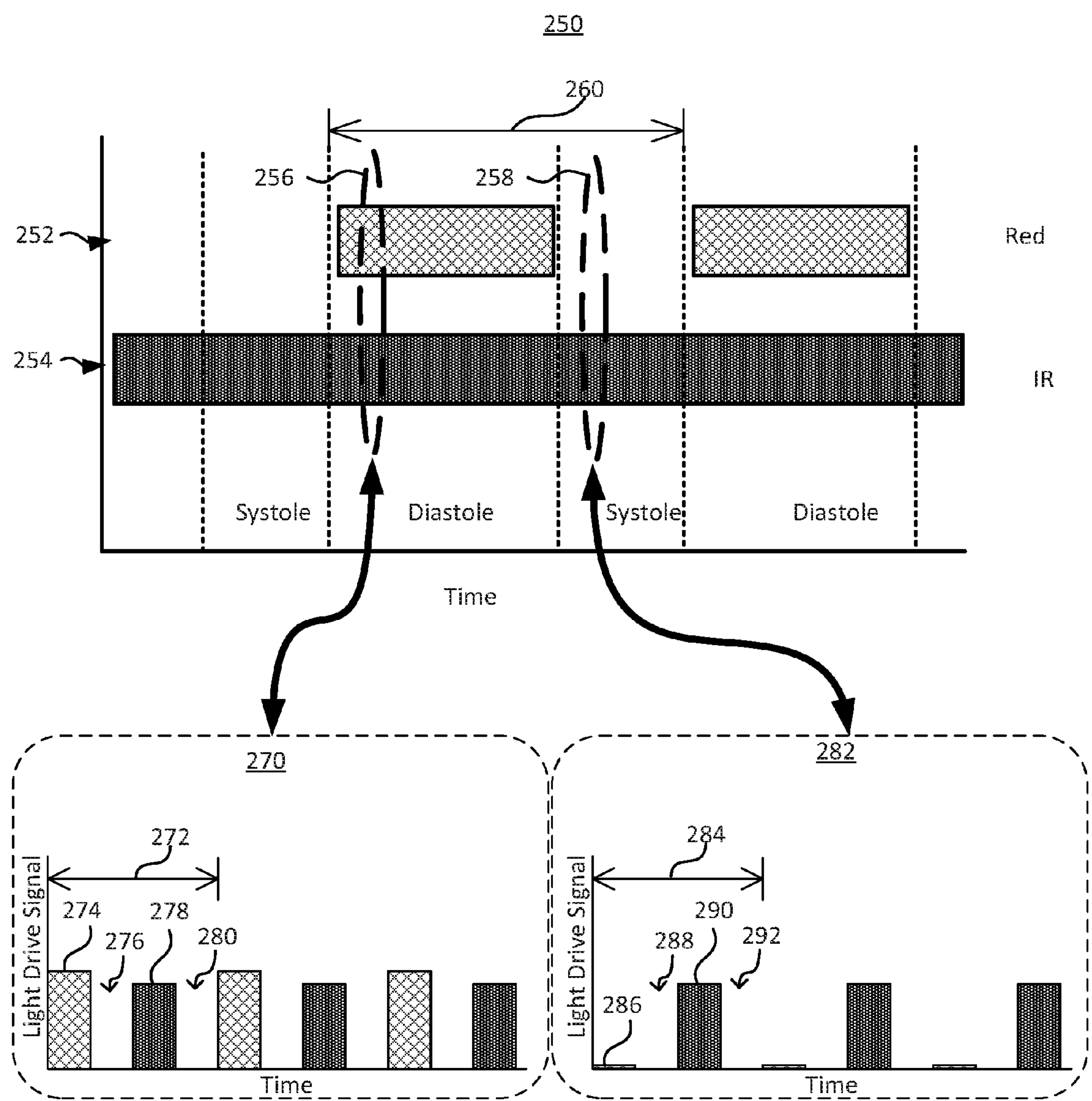
FIG. 2C shows illustrative timing diagrams of a drive cycle modulation and cardiac cycle modulation in accordance with some embodiments of the present disclosure.

FIG. 2C shows illustrative timing diagrams of drive cycle modulation and cardiac cycle modulation in accordance with some embodiments of the present disclosure. Plot 250 may include a timing diagram of an exemplary cardiac cycle modulation, including red light modulation 252 and IR light modulation 254. In the embodiment illustrated in plot 250, the IR light remains at a constant level and the red light is "on" only during the diastole period. The period of the modulation cycle may correspond to time interval 260. In a further embodiment, the system may replace some or all of the "off" periods with "on" periods of lower light intensity, shorter duty cycles, any other suitable parameter variations, or a combination thereof. It will be understood that the aforementioned cardiac cycle modulation technique is merely exemplary and that the system may use any suitable cardiac cycle modulation technique.

Region 256 of plot 250 indicates an interval of the timing diagram where both red light modulation 252 and IR light modulation 254 are in an "on" portion of the cardiac cycle modulation. Plot 270 shows an illustrative portion of region 256, where the system is employing a cardiac cycle modulation in addition to the drive cycle modulation. Plot 250 may include a drive cycle modulation technique with a period of time interval 272. The time scale of plot 270 may be significantly shorter than the time scale of plot 250, such that time interval 272 is significantly shorter than time interval 260. For example, time interval 260 (i.e., the period of the cardiac cycle modulation) may be on the order of 1 second, while time interval 272 (i.e., the period of the drive cycle modulation) may be on the order of 1 ms. Time interval 272 may include a sequence of red "on" portion 274, a first "off" portion 276, IR "on" portion 278, and a second "off" portion 280. The first "off" portion 276 and second "off" portion 280 may be used to determine the level of ambient light, noise, dark current, other suitable signals, or any combination thereof. The system may subtract the background or dark level from the levels received during red "on" portion 274 and IR "on" period 278.

Region 258 of plot 250 indicates an interval of the timing diagram where the red light modulation 252 is in an "off" portion of the cardiac cycle modulation and IR light modulation 254 is in an "on" portion of the cardiac cycle modulation. Plot 282 shows an illustrative portion of region 258, where the system is employing a drive cycle modulation technique in addition to the cardiac cycle modulation. Plot 282 may include a drive cycle modulation technique with a period of time interval 284. The time scale of plot 282 may be significantly shorter than the time scale of plot 250, such that time interval 284 is significantly shorter than time interval 260. In some embodiments, the time scale of plot 282 may be the same as the time scale of plot 270. Time interval 284 may include a sequence of red "on" portion 286, a first "off" portion 288, IR "on" portion 290, and a second "off" portion 292. The red "on" portion 286 may include less red light emitted than during red "on" portion 274, or no red light emitted, as red light modulation 252 is in an "off" phase during region 258. The first "off" portion 288 and second "off" portion 292 may be used to determine the level of ambient light, noise, dark current, other suitable signals, or any combination thereof. The system may subtract the background or dark level from the levels received during red "on" portion 286 and IR "on" portion 290.

Red light modulation 252 may be in an "on" portion during region 256 (illustrated in detail in plot 270) and an "off" portion during region 258 (illustrated in detail in plot 282). Thus, the level of red light indicated by red "on" portion 274 is at a high level and the level of red light indicated by red "on" portion 286 is at a low level. This is illustrative of an embodiment where drive cycle modulation occurs together with cardiac cycle modulation. It will be understood that the techniques illustrated by FIG. 2C are merely exemplary and that other suitable techniques may be used for drive cycle modulation, as described above. It will also be understood that other suitable methods may be used to combine the drive cycle modulation and the cardiac cycle modulation. It will also be understood that the combining technique may depend in part on the particular drive cycle modulation and cardiac cycle modulation technique. It will also be understood that conventional servo algorithms may be used in addition to combinations of drive cycle modulation and cardiac cycle modulation.

Figure 3:
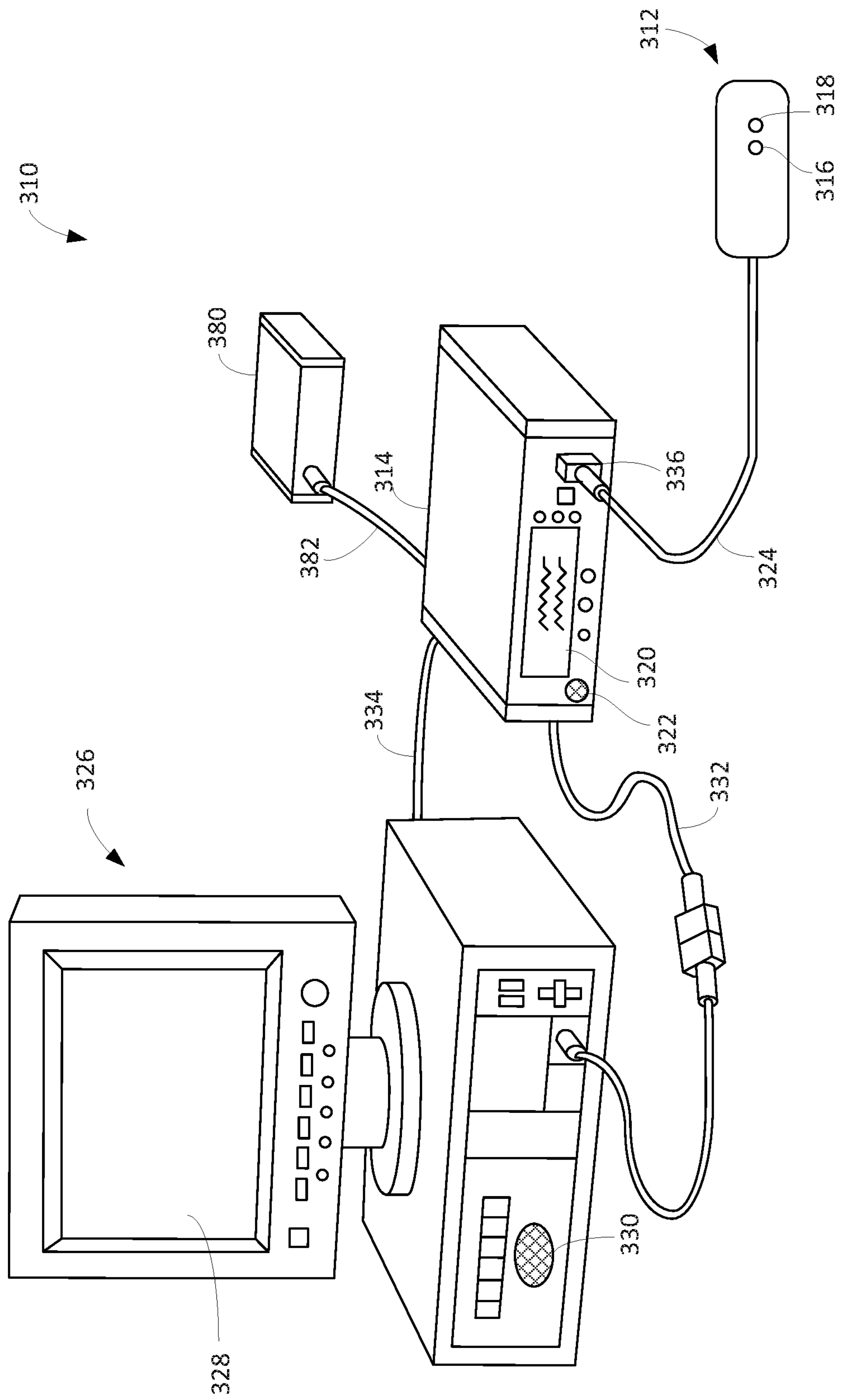
FIG. 3 is a perspective view of an embodiment of a physiological monitoring system in accordance with some embodiments of the present disclosure.

FIG. 3 is a perspective view of an embodiment of a physiological monitoring system 310 in accordance with some embodiments of the present disclosure. In some embodiments, one or more components of physiological monitoring system 310 may include one or more components of physiological monitoring system 100 of FIG. 1. System 310 may include sensor unit 312 and monitor 314. In some embodiments, sensor unit 312 may be part of an oximeter. Sensor unit 312 may include one or more light source 316 for emitting light at one or more wavelengths into a subject's tissue. One or more detector 318 may also be provided in sensor unit 312 for detecting the light that is reflected by or has traveled through the subject's tissue. Any suitable configuration of light source 316 and detector 318 may be used. In an embodiment, sensor unit 312 may include multiple light sources and detectors, which may be spaced apart. System 310 may also include one or more additional sensor units (not shown) that may, for example, take the form of any of the embodiments described herein with reference to sensor unit 312. An additional sensor unit may be the same type of sensor unit as sensor unit 312, or a different sensor unit type than sensor unit 312 (e.g., a photoacoustic sensor). Multiple sensor units may be capable of being positioned at two different locations on a subject's body.

In some embodiments, sensor unit 312 may be connected to monitor 314 as shown. Sensor unit 312 may be powered by an internal power source, e.g., a battery (not shown). Sensor unit 312 may draw power from monitor 314. In another embodiment, the sensor may be wirelessly connected to monitor 314 (not shown). Monitor 314 may be configured to calculate physiological parameters based at least in part on data relating to light emission and acoustic detection received from one or more sensor units such as sensor unit 312. For example, monitor 314 may be configured to determine pulse rate, blood pressure, blood oxygen saturation (e.g., arterial, venous, or both), hemoglobin concentration (e.g., oxygenated, deoxygenated, and/or total), any other suitable physiological parameters, or any combination thereof. In some embodiments, calculations may be performed on the sensor units or an intermediate device and the result of the calculations may be passed to monitor 314. Further, monitor 314 may include display 320 configured to display the physiological parameters or other information about the system. In the embodiment shown, monitor 314 may also include a speaker 322 to provide an audible sound that may be used in various other embodiments, such as for example, sounding an audible alarm in the event that a subject's physiological parameters are not within a predefined normal range. In some embodiments, the system 310 includes a stand-alone monitor in communication with the monitor 314 via a cable or a wireless network link. In some embodiments, monitor 314 may be implemented as monitor 104 of FIG. 1.

In some embodiments, sensor unit 312 may be communicatively coupled to monitor 314 via a cable 324. Cable 324 may include electronic conductors (e.g., wires for transmitting electronic signals from detector 318), optical fibers (e.g., multi-mode or single-mode fibers for transmitting emitted light from light source 316), any other suitable components, any suitable insulation or sheathing, or any combination thereof. In some embodiments, a wireless transmission device (not shown) or the like may be used instead of or in addition to cable 324. Monitor 314 may include a sensor interface configured to receive physiological signals from sensor unit 312, provide signals and power to sensor unit 312, or otherwise communicate with sensor unit 312. The sensor interface may include any suitable hardware, software, or both, which may be allow communication between monitor 314 and sensor unit 312.

Calibration device 380, which may be powered by monitor 314, a battery, or by a conventional power source such as a wall outlet, may include any suitable calibration device. Calibration device 380 may be communicatively coupled to monitor 314 via communicative coupling 382, and/or may communicate wirelessly (not shown). In some embodiments, calibration device 380 is completely integrated within monitor 314. In some embodiments, calibration device 380 may include a manual input device (not shown) used by an operator to manually input reference signal measurements obtained from some other source (e.g., an external invasive or non-invasive physiological measurement system).

In the illustrated embodiment, system 310 includes a multi-parameter physiological monitor 326. The monitor 326 may include a cathode ray tube display, a flat panel display (as shown) such as a liquid crystal display (LCD) or a plasma display, or may include any other type of monitor now known or later developed. Multi-parameter physiological monitor 326 may be configured to calculate physiological parameters and to provide a display 328 for information from monitor 314 and from other medical monitoring devices or systems (not shown). For example, multi-parameter physiological monitor 326 may be configured to display an estimate of a subject's blood oxygen saturation and hemoglobin concentration generated by monitor 314. Multi-parameter physiological monitor 326 may include a speaker 330.

Monitor 314 may be communicatively coupled to multi-parameter physiological monitor 326 via a cable 332 or 334 that is coupled to a sensor input port or a digital communications port, respectively and/or may communicate wirelessly (not shown). In addition, monitor 314 and/or multi-parameter physiological monitor 326 may be coupled to a network to enable the sharing of information with servers or other workstations (not shown). Monitor 314 may be powered by a battery (not shown) or by a conventional power source such as a wall outlet.

In some embodiments, all or some of monitor 314 and multi-parameter physiological monitor 326 may be referred to collectively as processing equipment. In some embodiments, any of the processing components and/or circuits, or portions thereof, of FIGS. 1 and 3 may be referred to collectively as processing equipment. For example, processing equipment may be configured to generate light drive signals, amplify, filter, sample and digitize detector signals, and calculate physiological information from the digitized signal. In some embodiments, all or some of the components of the processing equipment may be referred to as a processing module.

Figure 4:
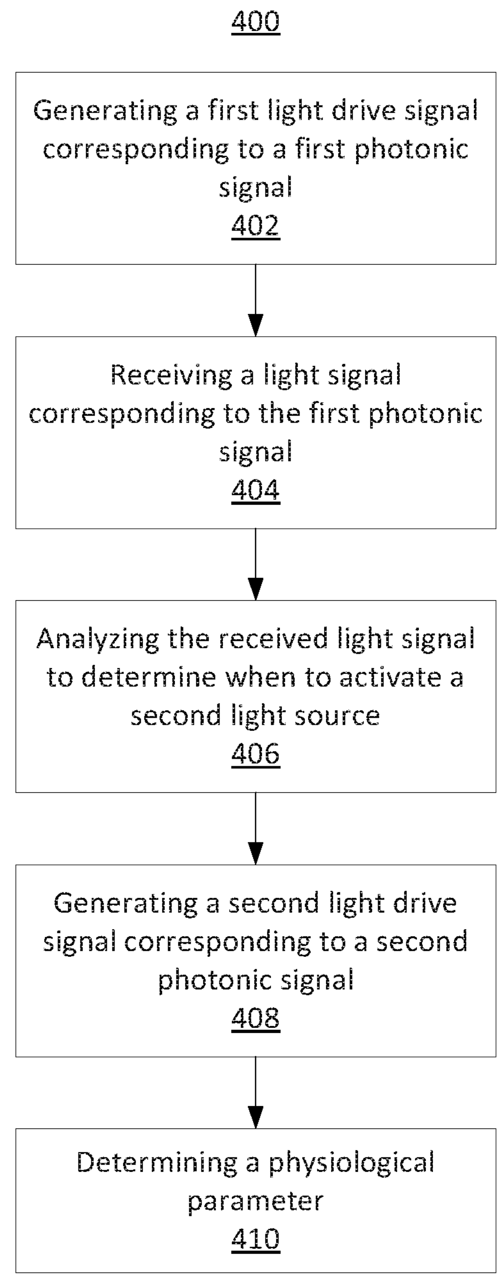
FIG. 4 is a flow diagram showing illustrative steps for determining a physiological parameter in accordance with some embodiments of the present disclosure.

FIG. 4 is flow diagram 400 showing illustrative steps for determining a physiological parameter in accordance with some embodiments of the present disclosure. In some embodiments, the system may emit a photonic signal from a first light source and use information from the related attenuated signal to generate a light drive signal for a second light source.

In step 402, the system may generate a first light drive signal. The light drive signal may be used by a light source to emit a photonic signal. The light source may be one or more LEDs, laser diodes, other suitable device, or any combination thereof. For example, the light source may include light source 130 of FIG. 1 or light source 316 of FIG. 3. In some embodiments, the light source may include LEDs of multiple wavelengths, for example, a red LED and an IR led. In some embodiments, the light source may include multiple LEDs of the same wavelength, multiple LEDs of different wavelengths, any other suitable arrangement, or any combination thereof. In some embodiments, the light source may include a fiber optic or other light pipe to communicate light from one location to another. In some embodiments, the light drive signal may include or be a component of a cardiac cycle modulation. For example, the first light drive signal may be configured to activate one LED to emit a photonic signal and not activate other LEDs, such that some physiological parameters may be determined, but with lower power consumption than when the other LEDs are illuminated.

In step 404, the system may receive a light signal. The light may be received using a sensor, for example, detector 140 of FIG. 1 or detector 318 of FIG. 3. The light signal may be attenuated by the subject. The received light signal may in part include light from the first photonic signal. For example, the system may emit light that is reflected by the subject or transmitted through the subject. The interaction of the emitted light with the subject may cause the light to become attenuated. In some embodiments, the attenuation of the light may depend on the wavelength of the light and the tissue with which the light interacts. For example, particular wavelengths of light may be attenuated more strongly by oxyhemoglobin than other wavelengths. In some embodiments, the system may amplify the received signal using front end processor circuitry. In some embodiments, the gain may be modulated using a technique correlated to the cardiac cycle modulation. The gain of the amplifier may be adjusted based on the emitted light brightness, historical information related to the brightness of prior received attenuated signals, other suitable information, or any combination thereof, so that the amplified signal matches the range of the analog-to-digital converter and thus increases resolution. In some embodiments, the system may account for the gain using hardware, software, or any combination thereof, such that the original intensity information is retained.

In step 406, the system may analyze the received light signal to determine when to activate a second light source and/or parameters of a second photonic signal In some embodiments, the second light source may include one or more emitters. In some embodiments, the system may identify peaks, valleys, inflection points, slope changes, fiducial points, other suitable elements, or any combination thereof in the received light source. In some embodiments, the system may use information determined from analyzing the first light source in addition to other information. Other information may include, for example, historical analysis of prior cardiac cycles and information from external sensors. For example, the system may determine an average pulse period from a number of prior pulse cycles. Statistical information such as the standard deviation may also be calculated to in part determine a confidence parameter for the historical information. In some embodiments, the system may use a respiration rate. For example, the system may determine a respiration rate from an external sensor and use information from the respiration rate to determine a modulation technique. In some embodiments, the cardiac cycle modulation applied to the second light drive signal may be varied based on the historical and statistical information. In some embodiments, the system may determine to turn on a second light source with a time offset to the element of interest in the cardiac cycle. For example, the system may turn on the second light source a certain number of milliseconds prior to the peak (or expected peak) of a pulse signal. In a further example, the system may wait a certain number of milliseconds following a peak in an ECG signal. In some embodiments, the time offsets may be adjusted based on prior signal analysis, adjusted by user input, adjusted by predetermined values, adjusted by any other suitable technique, or any combination thereof. In some embodiments, parameters of the second photonic signal, for example duty cycle, decimation ratio, and brightness, may be determined based on analysis of the received light signal.

In step 408, the system may generate a second light drive signal. The second light drive signal may be configured to activate a second light source or a different emitter from the first light source to emit a second photonic signal. For example, in a cardiac cycle modulation where a first light source remains on at a constant level (e.g., in a drive cycle modulation) and a second light source is turned on and off to optimize power consumption, the second light drive signal may cause a second light source to emit light at a particular time or times in the cardiac cycle. Light from the second photonic signal may be attenuated by the subject and received by a sensor. In some embodiments, the system may adjust the second light drive signal based on historical data. For example, the system may use information from prior pulse cycles to determine an optimal emitter brightness.

In step 410, the system may determine a physiological parameter using information from the attenuated photonic signals. The physiological parameter may be determined using any suitable hardware technique, software technique, or combination thereof. In some embodiments, processing equipment remote to the system may be used to determine physiological parameters. The system may display the determined physiological parameter using a local display (e.g., display 320 of FIG. 3 or display 328 of FIG. 3), display them on a remote display, publish the data to a server or website, make the parameters available to a user by any other suitable technique, or any combination thereof.

Figure 5:
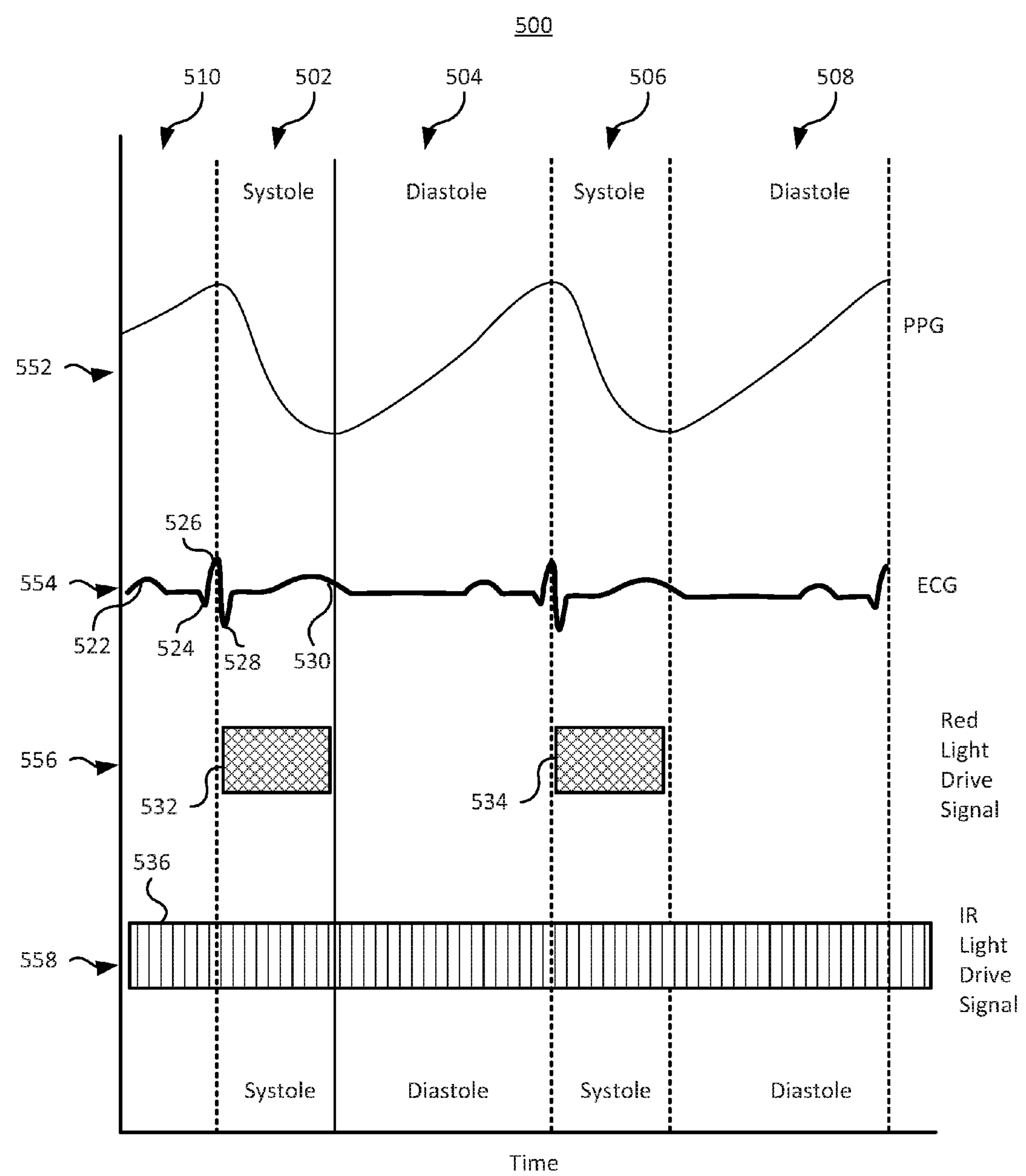
FIG. 5 shows an illustrative timing diagram of a physiological monitoring system in accordance with some embodiments of the present disclosure.

FIG. 5 shows illustrative timing diagram 500 of a physiological monitoring system in accordance with some embodiments of the present disclosure. In some embodiments, the system may use a first light drive signal to identify the systole periods of the cardiac cycle and modulate a second light drive signal to increase light intensity concurrent with the systole periods. Timing diagram 500 may include time on the abscissa axis and either arbitrary amplitude or unitless dimensions on the ordinate axis depending on the row of the diagram. Timing diagram 500 may include time periods related to the cardiac cycle, including systole period 502, diastole period 504, systole period 506, and diastole period 508. Timing diagram 500 may also include diastole period 510, though only a portion of this diastole period is drawn. Timing diagram 500 may include PPG signal 552, ECG signal 554, red light drive signal 556, and IR light drive signal 558. PPG signal 552 and ECG signal 554 are shown with arbitrary units on the ordinate axis. Red light drive signal 556 and IR light drive signal 558 are shown as "on" or "off" states without units associated with the ordinate axis.

Timing diagram 500 may include ECG signal 554, which is indicative of electrical signals associated with the cardiac cycle. ECG signal 554 may include P wave 522, Q wave 524, R wave 526, S wave 528, and T wave 530. In some embodiments, ECG signals may be used in addition to or in place of information from PPG signal 552.

It will be understood that the particular alignment of ECG signal 554 with elements in PPG signal 552 is dependent upon the location on the subject where the PPG signal is measured. For example, a PPG signal is typically monitored at a location remote from the heart, creating a time delay between the ECG signal and corresponding pulses in the PPG. Additionally, there may be a time delay between the electrical depolarization of the heart (QRS complex of an ECG) and the ejection of blood from the heart. This time delay may include an electro-mechanical delay before the heart muscle contracts and a period of isovolumetric contraction where the muscle tension in the heart increases but the pressure does not exceed the aortic pressure. During the period of isovolumetric contraction, the aortic valve may remain closed.

In some embodiments, the system may send a drive signal without a cardiac modulation to a first light source. For example, the system may not apply a cardiac cycle modulation to IR light drive signal 558. IR light drive signal 558 may, for example, correspond to the first light drive signal generated at step 402 of FIG. 4. In some embodiments, the system may detect an attenuated photonic signal associated with IR light drive signal 558 throughout the cardiac pulse cycle. In some embodiments, elements of the cardiac cycle may be identified using other signals, for example, ECG signal 554. The system may determine periods of the cardiac cycle and apply a cardiac cycle modulation to a second light source. For example, red light drive signal 556 may be switched on at period 532 during systole period 502, off during diastole period 504, on at period 534 during systole period 506, and off during diastole period 508. Red light drive signal 556 may, for example, correspond to the second light drive signal generated at step 408 of FIG. 4. Thus, the cardiac cycle modulation applied to red light drive signal 556 may be substantially synchronous with the systole periods of the cardiac cycle. In some embodiments, the system may determine the timing of the systole periods using information from the attenuated first photonic signal associated with IR light drive signal 558. In some embodiments, the system may use historical information from multiple cardiac cycles to determine the red light drive signal 556.

It will be understood, and illustrated in the following figures, that the cardiac cycle modulation shown in timing diagram 500 is merely illustrative and that the system may use other suitable modulation techniques. It will also be understood, for this figure and the following figures, that the system may use a drive cycle modulation technique as illustrated in FIG. 2C and conventional servo algorithms in addition to the cardiac cycle modulation. It will also be understood, for this figure and the following figures, that the alignment of PPG signal 552, ECG signal 554, red light drive signal 556 and IR light drive signal 558 is merely exemplary and may include various time offsets and adjustments (not shown) dependent upon placement of sensors on the subject, physiological conditions, emitter equipment, sensor equipment, other suitable reasons, or any combination thereof. In some embodiments, the system may not include IR light drive signal 558 and may apply a cardiac cycle modulation technique to all light drive signals, as will be illustrated in FIGS. 10-16.

Figure 6:
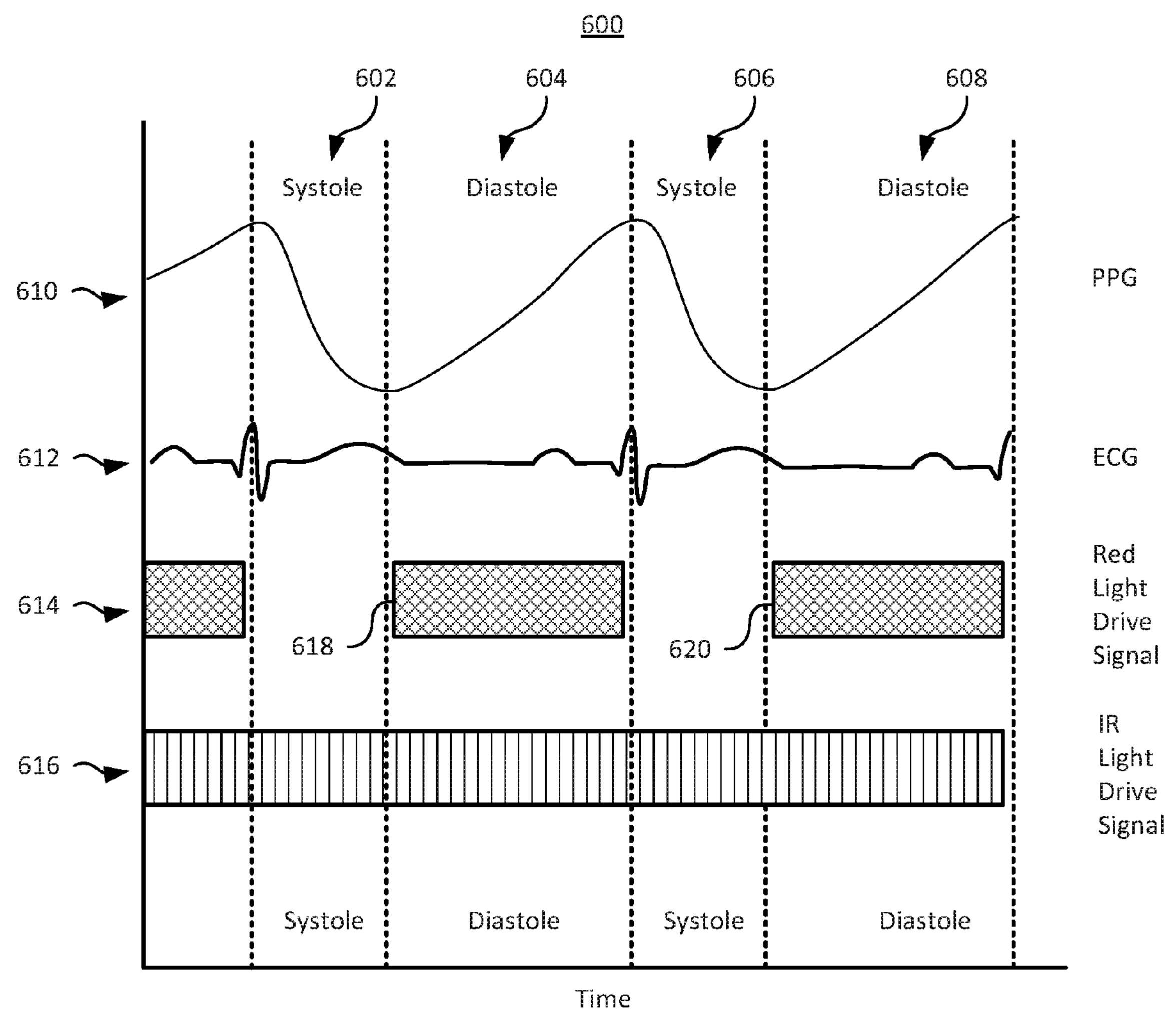
FIG. 6 shows another illustrative timing diagram of a physiological monitoring system in accordance with some embodiments of the present disclosure.

FIG. 6 shows another illustrative timing diagram 600 of a physiological monitoring system in accordance with some embodiments of the present disclosure. In some embodiments, the system may use a first light drive signal to identify diastole period periods in the cardiac cycle and modulate a second light drive signal to increase light intensity concurrent with the diastole period periods. Timing diagram 600 may include time periods related to the cardiac cycle, including systole period 602, diastole period 604, systole period 606, and diastole period 608. Timing diagram 600 may include PPG signal 610, ECG signal 612, red light drive signal 614, and IR light drive signal 616. PPG signal 610 and ECG signal 612 are shown with arbitrary units on the ordinate axis. Red light drive signal 614 and IR light drive signal 616 are shown as "on" or "off" portions without units associated with the ordinate axis.

In some embodiments, the system may send a drive signal without a cardiac cycle modulation to a first light source. For example, the system may generate IR light drive signal 616 without cardiac cycle modulation. IR light drive signal 616 may, for example, be the first light drive signal of step 402 of FIG. 4. In some embodiments, the system may detect an attenuated photonic signal associated with IR light drive signal 616 throughout the cardiac cycle. In some embodiments, elements of the cardiac cycle may be identified using other signals, for example, ECG signal 612. The system may determine periods of the cardiac cycle and apply a cardiac cycle modulation to a second light source. For example, red light drive signal 614 may be switched off during systole period 602, on at period 618 during diastole period 604, off during systole period 606, and on at period 620 during diastole period 608. Red light drive signal 614 may, for example, correspond to the second light drive signal generated at step 408 of FIG. 4. Thus, the cardiac cycle modulation applied to red light drive signal 614 may be substantially synchronous with the diastole periods of the cardiac cycle.

Figure 7:
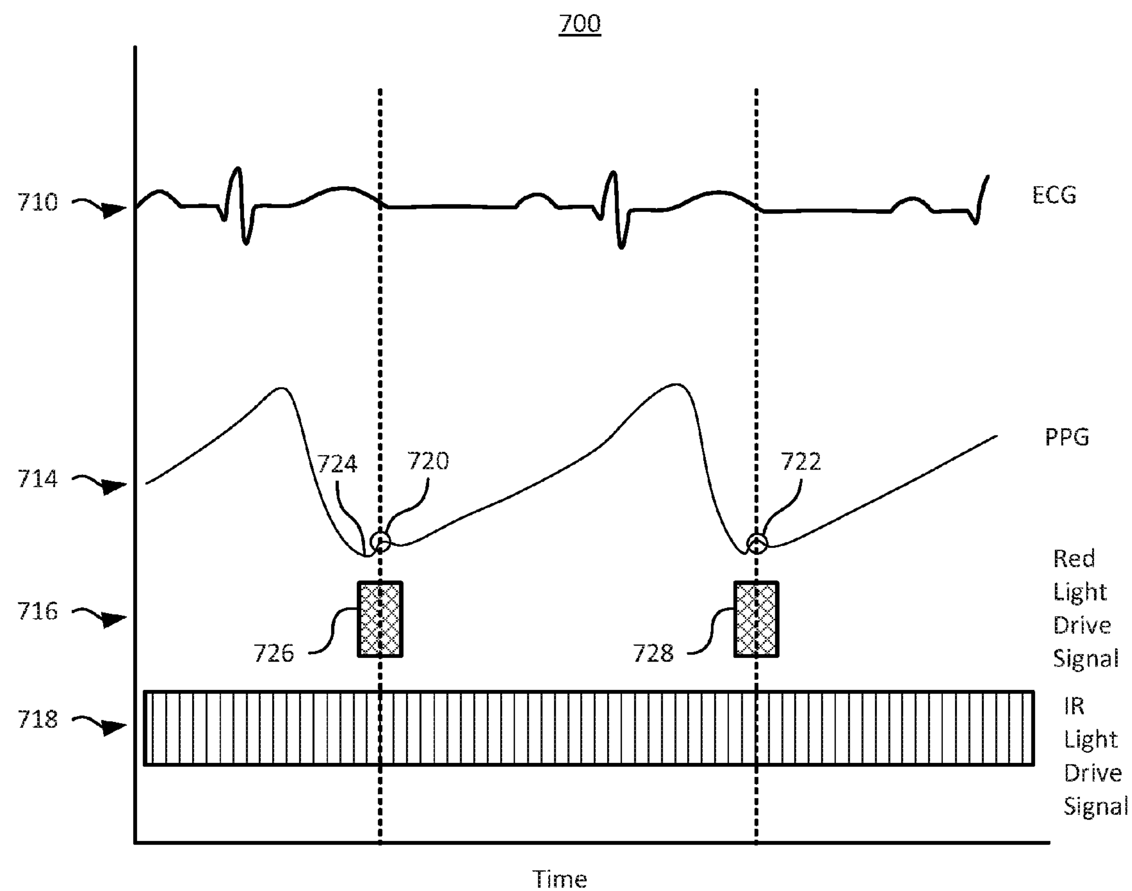
FIG. 7 shows another illustrative timing diagram of a physiological monitoring system in accordance with some embodiments of the present disclosure.

FIG. 7 shows another illustrative timing diagram 700 of a physiological monitoring system in accordance with some embodiments of the present disclosure. In some embodiments, the system may use a first light drive signal to identify a dicrotic notch or other point of interest in the cardiac cycle and modulate a second light drive signal to increase light intensity concurrent with the dicrotic notch. Timing diagram 700 may include ECG signal 710, PPG signal 714, red light drive signal 716, and IR light drive signal 718. ECG signal 710 and PPG signal 714 are shown with arbitrary units on the ordinate axis. PPG signal 714 is shown as a light intensity signal where a higher amplitude is indicative of more received light, or less blood in the sampled tissue. In some embodiments, PPG signal 714 in timing diagram 700 may be illustrated in a manner inverted from the common technique of illustrating PPG signals. Accordingly, elements of PPG signal 714 labeled herein as, for example, peaks and troughs, may be inverted from certain medical conventions. Red light drive signal 716 and IR light drive signal 718 are shown as "on" or "off" states without units associated with the ordinate axis.

In some embodiments, the system may send a drive signal to a first light source without cardiac modulation. For example, the system may not apply a cardiac cycle modulation to IR light drive signal 718. IR light drive signal 718 may be the first light drive signal of step 402 of FIG. 4. In some embodiments, the system may detect an attenuated photonic signal associated with IR light drive signal 718 throughout the cardiac pulse cycle. In some embodiments, elements of the cardiac cycle may be identified using other signals, for example, ECG signal 710. The system may determine periods of the cardiac cycle and apply a cardiac cycle modulation to a second light source. For example, the system may identify notch 720 in PPG signal 714. In some embodiments, the system may identify notch 720 indirectly using an element of PPG signal 714 (e.g., trough 724), using elements of ECG signal 710, by any other suitable technique, or any combination thereof. For example, notch 720 may be identified using a time offset from an element of ECG signal 710. As illustrated, there may be a time delay between trough 724 and notch 720. For example, red light drive signal 716 may be switched on during period 726, substantially concurrent with notch 720, and on during period 728, substantially concurrent with notch 722. Red light drive signal 716 may be the second light drive signal of step 408 of FIG. 4. Thus, the cardiac cycle modulation applied to red light drive signal 716 is substantially synchronous with the dicrotic notch of the cardiac cycle. In some embodiments, the system may turn on a light source before period 726 or a desired point of interest and turn off a light source following period 726 or a point of interest so that the photonic signal can stabilize, so that the detector can stabilize, so that the processing equipment can obtain extra samples for averaging, interpolating, or decimating, for amplifier gain adjustments to stabilize, for any other suitable reason, or any combination thereof. The system may determine the time offsets between the "on" portions and the region of interest based on user input, predetermined parameters, previous measurements, other suitable parameters, or any combination thereof. It will be understood that the use of a dicrotic notch for notch 720 is merely exemplary and that the system may identify any suitable point of interest. For example, the system may identify fiducial points such as local maxima and minima. Light sources may be illuminated, for example, as described below in reference to elements of FIG. 25.

Figure 8A:
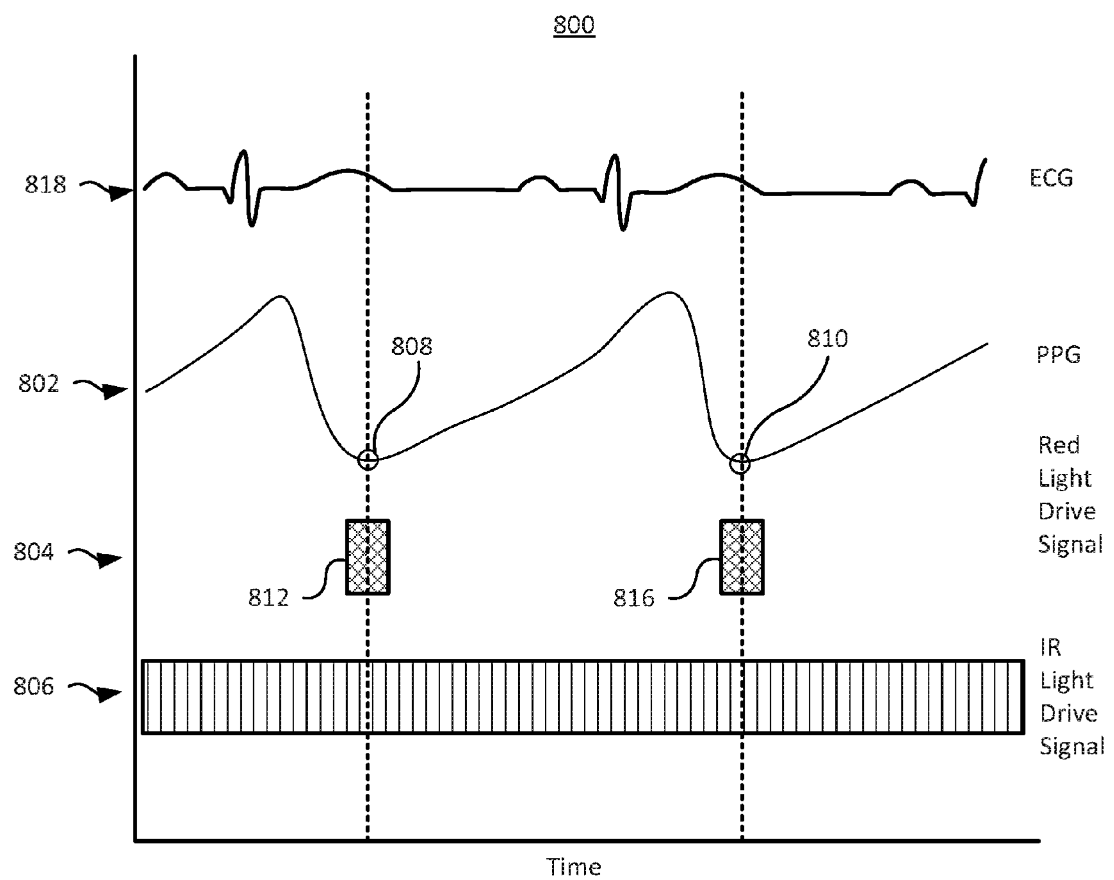
FIG. 8A shows another illustrative timing diagram of a physiological monitoring system in accordance with some embodiments of the present disclosure.

FIG. 8A shows another illustrative timing diagram 800 of a physiological monitoring system in accordance with some embodiments of the present disclosure. In some embodiments, the system may use a first light drive signal to identify the peak and troughs of the PPG signal and modulate a second light drive signal to increase light intensity concurrent with the PPG peaks. Timing diagram 800 may include PPG signal 802, red light drive signal 804, IR light drive signal 806, and ECG signal 818. PPG signal 802 and ECG signal 818 are shown with arbitrary units on the ordinate axis. Red light drive signal 804 and IR light drive signal 806 are shown as "on" or "off" states without units associated with the ordinate axis.

In some embodiments, the system may send a light drive signal to a first light source without a cardiac cycle modulation. For example, IR light drive signal 806 may not include a cardiac cycle modulation. IR light drive signal 806 may be the first light drive signal of step 402 of FIG. 4. In some embodiments, the system may detect an attenuated photonic signal associated with IR light drive signal 806 throughout the cardiac pulse cycle. In some embodiments, peaks, troughs, and other elements of the PPG signal or cardiac may be identified using other signals, for example, an ECG signal. The system may determine periods of the cardiac cycle and apply a cardiac cycle modulation to a second light source. For example, the system may identify point 808 and point 810 in PPG signal 802. In some embodiments, point 808 and 810 may represent peaks or troughs, depending on the orientation of the PPG signal. The system may turn on red light drive signal 804 during period 812, substantially concurrent with peak 808, and during period 816, substantially concurrent with peak 810. Red light drive signal 804 may be the second light drive signal of step 408 of FIG. 4. Thus, the cardiac cycle modulation applied to red light drive signal 804 is substantially synchronous with the peak of the PPG signal. In some embodiments, the system may turn on a light source before peaks 808 and 810 and turn off a light source following peaks 808 and 810 so that the photonic signal can stabilize, so that the detector can stabilize, so that the processing equipment can obtain extra samples for averaging, interpolating, or decimating, for amplifier gain adjustments to stabilize, for any other suitable reason, or any combination thereof. The system may determine the time offsets between the "on" periods and the region of interest based on user input, predetermined parameters, previous measurements, other suitable parameters, or any combination thereof.

Figure 8B:
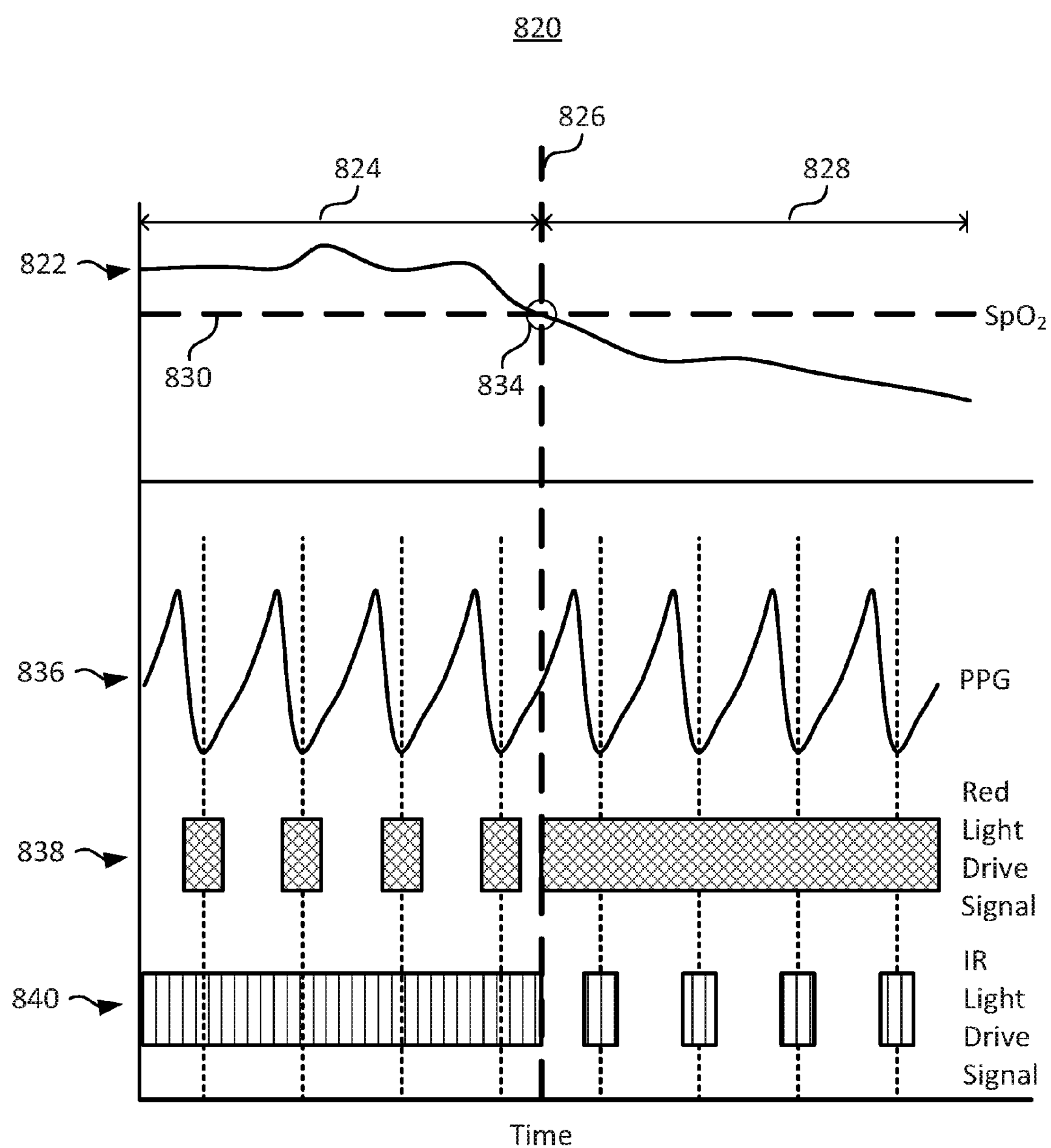
FIG. 8B shows another illustrative timing diagram of a physiological monitoring system in accordance with some embodiments of the present disclosure.

FIG. 8B shows another illustrative timing diagram 820 of a physiological monitoring system in accordance with some embodiments of the present disclosure. As shown in FIG. 8A, the system may use a first light drive signal to identify the peak and troughs of the PPG signal and modulate a second light drive signal to increase light intensity concurrent with the PPG peaks. In some embodiments, the use of the first and second light drive signals may be selected based on the blood oxygen saturation, other physiological parameters, other system parameters, or any combination thereof.

Timing diagram 820 may include $SpO_2$ signal 822, PPG signal 836, red light drive signal 838, and IR light drive signal 840. $SpO_2$ signal 822 may be shown with units of percentage on the ordinate axis. PPG signal 836 may be shown with arbitrary units on the ordinate axis. Red light drive signal 838 and IR light drive signal 840 may be shown as "on" or "off" states without units associated with the ordinate axis.

In some embodiments, the blood oxygen saturation may be compared to a threshold or target value, such as threshold 830. For example, threshold 830 may be approximately 70-80% of maximum blood oxygen saturation. During time interval 824, when the $SpO_2$ signal is greater than threshold 830, the system may operate in a first mode. For example, as illustrated, the system may use IR light drive signal 840 to monitor cardiac activity throughout a cardiac pulse cycle, and may modulate red light drive signal 838 accordingly. At time point 826, $SpO_2$ signal may cross threshold 830 at point 834. In some embodiments, this may be indicative of decreasing blood oxygen saturation. During time interval 828 following time point 826, the system may operate in a second mode. For example, as illustrated, the system may use red light drive signal 838 to monitor cardiac activity throughout a cardiac pulse cycle, and may modulate IR light drive signal 840 accordingly.

In some embodiments, blood with a relatively high blood oxygen saturation may absorb IR light more strongly than red light. Thus, the IR light may be more sensitive to pulsatile signals than red light. For example, blood with a high blood oxygen saturation may have a relatively higher concentration of oxyhemoglobin and a relatively lower concentration of deoxyhemoglobin, resulting in higher IR sensitivity. Conversely, in some embodiments, blood with a relatively low blood oxygen saturation may absorb red light more strongly than infrared light. For example, blood with a low blood oxygen saturation may have a relatively lower concentration of oxyhemoglobin and a relatively higher concentration of deoxyhemoglobin, resulting in higher red sensitivity. Thus, it may be desired to monitor activity with the more sensitive available wavelength.

It will be understood that selection and/or switching of the first and second light sources may depend on the blood oxygen saturation as well as additional physiological parameters and system parameters. For example, a red wavelength LED may consume more power than an IR LED, and thus it may be desired to use the lowest power consuming technique possible. In some embodiments, the system may select the light source capable of detecting the greatest pulsatile amplitude per unit of power consumed. In some other embodiments, the system may select the light source capable of detecting the greatest pulsatile amplitude. It will also be understood that in some embodiments, a decreasing blood oxygen saturation or other physiological parameter may result in the system not using a cardiac cycle modulation technique in order to attain the highest possible quality physiological information. This will be discussed below, for example with relation to FIG. 21.

Figure 9:
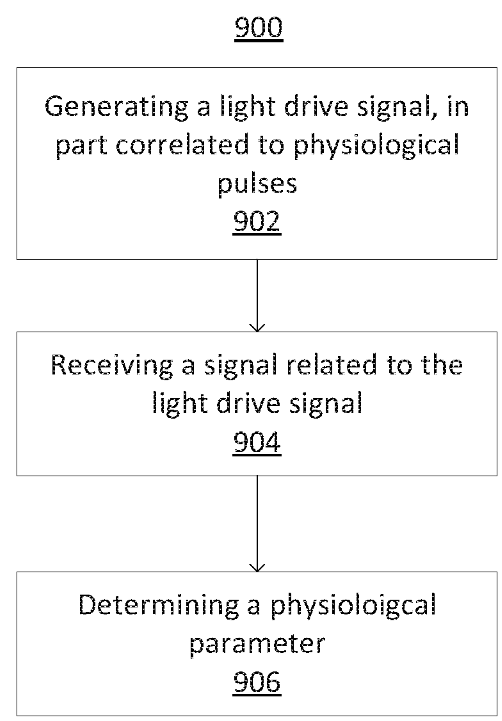
FIG. 9 is a flow diagram showing illustrative steps for determining a physiological parameter in accordance with some embodiments of the present disclosure.

FIG. 9 is flow diagram 900 showing illustrative steps for determining a physiological parameter in accordance with some embodiments of the present disclosure. In some embodiments, the system may emit a photonic signal correlated to physiological pulses from a light source, and use information from the related attenuated signal to determine physiological parameters. In some embodiments, varying parameters of the light drive signal may reduce, optimize, or otherwise suitably alter the power consumption of the system.

In step 902, the system may generate a light drive signal, in part correlated to physiological pulses. The system may generate a light drive signal used by a light source to emit a photonic signal. The light source may be one or more emitters of one or more wavelengths, and they may emit one or more photonic signals. For example, the light source may include light source 130 of FIG. 1 or light source 316 of FIG. 3. In some embodiments, the light source may include LEDs of multiple wavelengths, for example, a red LED and an IR LED. In some embodiments, the light source may include multiple LEDs of the same wavelength, multiple LEDs of different wavelengths, any other suitable arrangement, or any combination thereof. In some embodiments, the light source may include a fiber optic or other light pipe to communicate light from one location to another.

The system may generate the light drive signal such that a parameter of the emitted one or more photonic signals varies substantially synchronously with physiological pulses of the subject. For example, the system may generate a light drive signal that varies with a period the same as or closely related to the period of the cardiac cycle, thus generating a cardiac cycle modulation. The system may vary parameters related to the light drive signal including drive current or light brightness, duty cycle, firing rate, modulation parameters, other suitable parameters, or any combination thereof. In some embodiments, the system may use a cardiac cycle modulation that spans several cardiac cycles (e.g., emitting light from a light source during the first one of every five cycles). In some embodiments, the system may generate a light drive signal that modulates parameters of more than one light source using more than one modulation technique. It will be understood that the system may apply this cardiac cycle modulation to the light drive signal in addition to a drive cycle modulation, as illustrated in FIG. 2C, and conventional servo algorithms.

In some embodiments, physiological pulses may be cardiac pulses, respiratory pulses, muscular pulses, any other suitable pulses, or any combination thereof. Where physiological pulses are respiratory pulses, they may relate to respiration rate, inspiration, expiration, ventilator parameters, changes in a respiratory pressure signals, any other suitable parameter, or any combination thereof. In some embodiments, particular segments of a respiratory cycle may provide an increased signal to noise ratio, increased signal strength, increased physiological parameter accuracy, increased physiological parameter precision, any other suitable parameters, or any combination thereof. In some embodiments, respiration may cause variations in photoplethysmography data, and thus it may be desired to correlate a modulation technique with respiration variations or both respiration variations and cardiac pulses.

In some embodiments, the system may use information to determine the cardiac cycle modulation. Information may include, for example, historical analysis of prior cardiac cycles and information from external sensors. For example, the system may determine an average pulse period from a number of prior pulse cycles. Statistical information such as the standard deviation may also be calculated to in part determine a confidence parameter for the historical information. In some embodiments, the cardiac cycle modulation applied to the light drive signal may be varied based on the historical and statistical information.

In step 904, the system may receive a light signal. The light may be received using a sensor, for example, detector 140 of FIG. 1 or detector 318 of FIG. 3. The light signal may be attenuated by the subject. The received light signal may in part include light from the photonic signal. For example, the system may emit light that is reflected by the subject or transmitted through the subject. Interactions of the emitted light with the subject may cause the light to become attenuated. In some embodiments, the attenuation of the light may depend on the wavelength of the light and the tissue with which the light interacts. For example, particular wavelengths of light may be attenuated more strongly by oxyhemoglobin than other wavelengths. In some embodiments, the system may amplify the received signal using front end processor circuitry. The gain of the amplifier may be adjusted based on the emitted light brightness, historical information related to the brightness of prior received attenuated signals, other suitable information, or any combination thereof, so that the amplified signal matches the range of the analog-to-digital converter and thus increases resolution. In some embodiments, the system may account for the gain using hardware, software, or any combination thereof, such that the original intensity information is retained.

In step 906, the system may determine a physiological parameter using information from the attenuated photonic signals. The physiological parameter may be determined using any suitable hardware technique, software technique, or combination thereof. In some embodiments, processing equipment remote to the system may be used to determine physiological parameters. The system may display the determined physiological parameter using a local display (e.g., display 320 of FIG. 3 or display 328 of FIG. 3), display them on a remote display, publish the data to a server or website, make the parameters available to a user by any other suitable technique, or any combination thereof.

Figure 10:
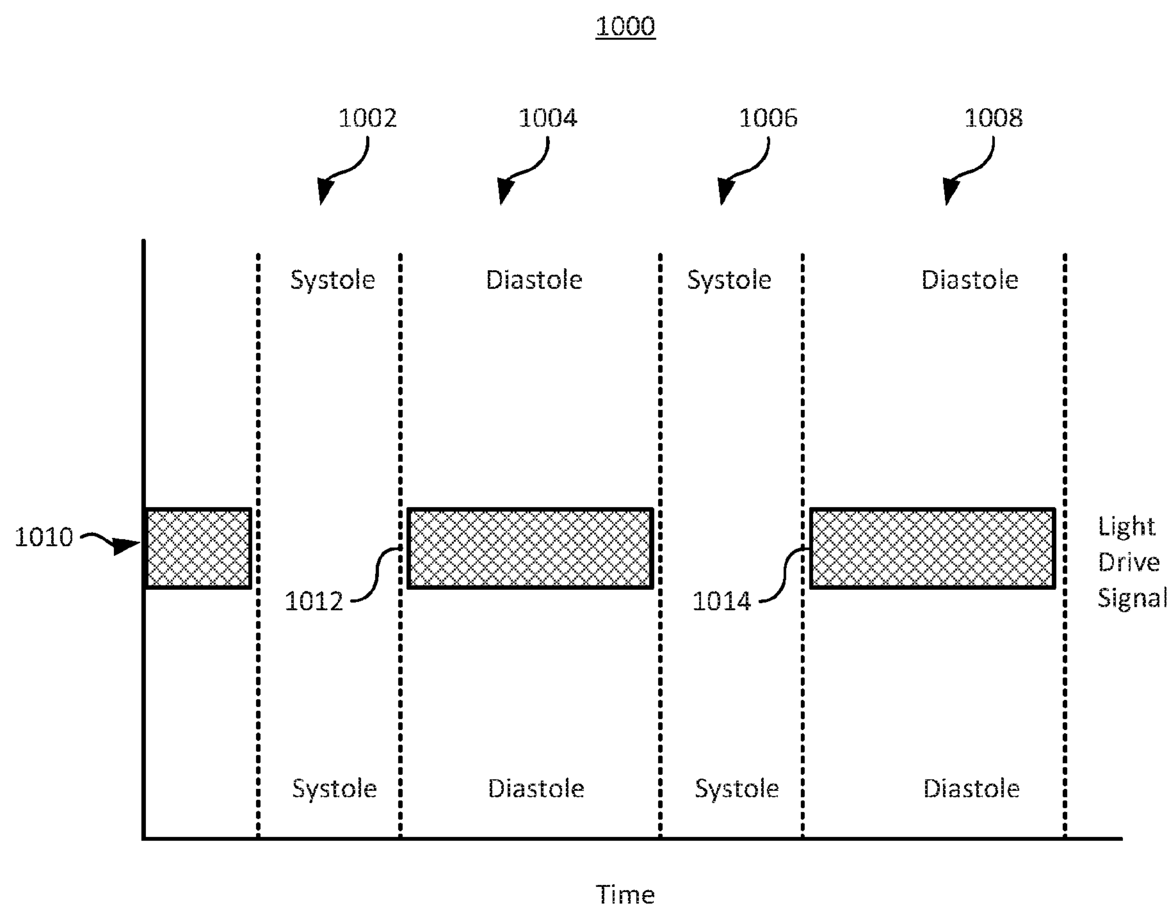
FIG. 10 shows another illustrative timing diagram of a physiological monitoring system in accordance with some embodiments of the present disclosure.

FIG. 10 shows another illustrative timing diagram 1000 of a physiological monitoring system in accordance with some embodiments of the present disclosure. In some embodiments, the system may vary a light drive signal such that a parameter is varied concurrent with diastole periods of the cardiac cycle. Timing diagram 1000 may include time periods related to the cardiac cycle, including systole period 1002, diastole period 1004, systole period 1006, and diastole period 1008. Timing diagram 1000 may include light drive signal 1010, shown in "on" and "off" states without units on the ordinate axis. It will be understood that light drive signal 1010 may provide a light drive signal to one or more emitters. It will also be understood any suitable number of cardiac cycle modulation techniques may be used with any suitable number of emitters.

In some embodiments, the system may modulate light drive signal 1010 in a way related to the cardiac cycle. For example, light drive signal 1010 may correspond to the light drive signal generated at step 902 of FIG. 9. In some embodiments, the system may turn off a light drive signal for systole period 1002, turn on the light drive signal for diastole period 1004, turn off the light drive signal for systole period 1006, and turn on the light drive signal for diastole period 1008. Thus, the cardiac cycle modulation applied to light drive signal 1010 may be substantially synchronous with the diastole periods of the cardiac cycle. In some embodiments, the system may turn on a light source before diastole periods 1004 and 1008 and turn off a light source following diastole periods 1004 and 1008 so that the photonic signal can stabilize, so that the detector can stabilize, so that the processing equipment can obtain extra samples for averaging, interpolating, or decimating, for amplifier gain adjustments to stabilize, for any other suitable reason, or any combination thereof.

The system may determine the time offsets between the "on" periods and the region of interest based on user input, predetermined parameters, previous measurements, other suitable parameters, or any combination thereof. The system may determine the timing of the diastole periods using historical information from previous cardiac cycles, from an external sensor, from user input, from measurements made with a different cardiac cycle modulation, by any other suitable technique, or any combination thereof. For example, the system may desire to align a particular portion of the received signal with the center of a modulation cycle (or other suitable criteria) and advance or delay subsequent modulation cycles to improve the alignment. It will be understood that the system may align modulation with pulses of the heart, pulses of a particular muscle group, other suitable pulses, any other suitable physiological function, or any combination thereof.

It will also be understood that modulation of the light drive signal (i.e., the "on" and "off" states illustrated by light drive signal 1010) is merely exemplary and may include modulation of parameters including drive current or light brightness, duty cycle, firing rate, modulation parameters, other suitable parameters, or any combination thereof. It will also be understood that the "on" and "off" states are merely exemplary and that the system may use any suitable variations of discrete and/or continuous modulations. For example, discrete modulations may include drive signals with one or more step functions. Continuous modulations may include sinusoidal waveforms.

Figure 11:
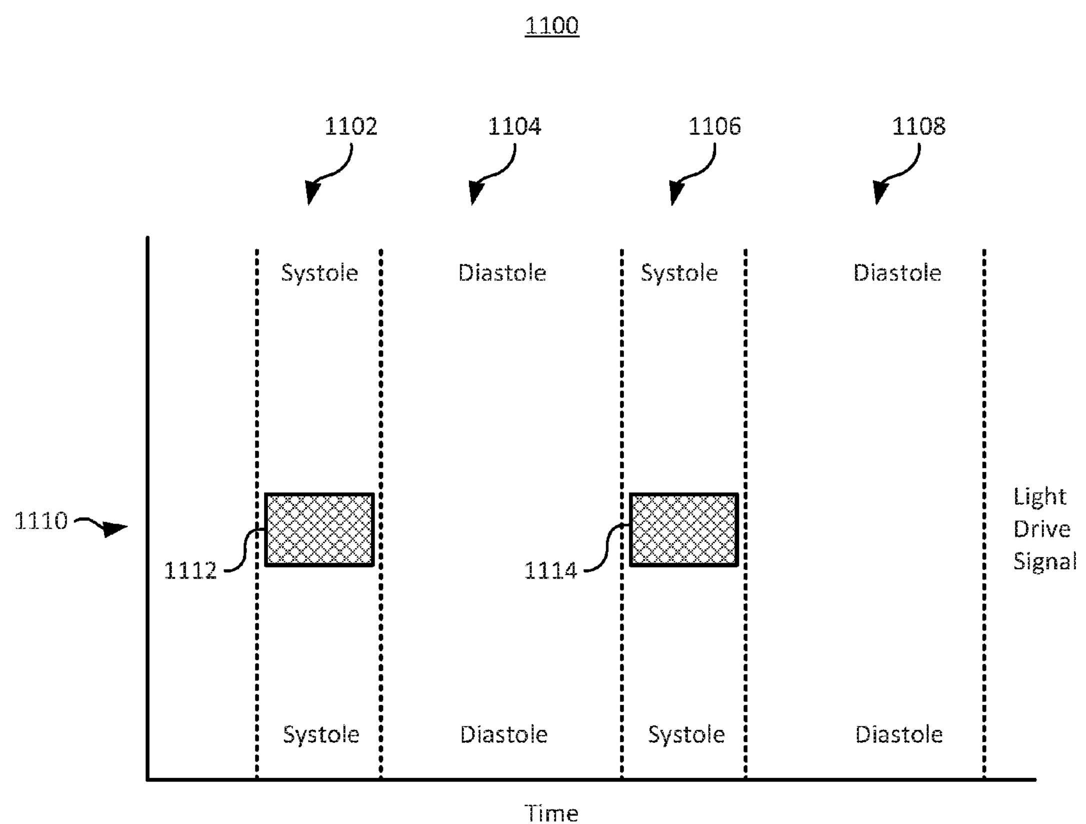
FIG. 11 shows another illustrative timing diagram of a physiological monitoring system in accordance with some embodiments of the present disclosure.

FIG. 11 shows another illustrative timing diagram 1100 of a physiological monitoring system in accordance with some embodiments of the present disclosure. In some embodiments, the system may vary a light drive signal such that a parameter is increased concurrent with systole periods of the cardiac cycle. Timing diagram 1100 may include time periods related to the cardiac cycle, including systole period 1102, diastole period 1104, systole period 1106, and diastole period 1108. Timing diagram 1100 may include light drive signal 1110, shown in "on" and "off" states without units on the ordinate axis. It will be understood that light drive signal 1110 may provide a light drive signal to one or more emitters. It will also be understood any suitable number of cardiac cycle modulation techniques may be used with any suitable number of emitters.

In some embodiments, the system may modulate light drive signal 1110 in a way related to the cardiac cycle. Light drive signal 1110 may correspond to the light drive signal generated at step 902 of FIG. 9. In some embodiments, the system may turn on a light drive signal for systole period 1102, turn off the light drive signal for diastole period 1104, turn on the light drive signal for systole period 1106, and turn off the light drive signal for diastole period 1108. Thus, the cardiac cycle modulation applied to light drive signal 1110 may be substantially synchronous with the systole periods of the cardiac cycle. In some embodiments, the system may turn on a light source before systole periods 1102 and 1106 and turn off a light source following systole periods 1102 and 1106 so that the photonic signal can stabilize, so that the detector can stabilize, so that the processing equipment can obtain extra samples for averaging, interpolating, or decimating, for amplifier gain adjustments to stabilize, for any other suitable reason, or any combination thereof. The system may determine the time offsets between the "on" periods and the region of interest based on user input, predetermined parameters, previous measurements, other suitable parameters, or any combination thereof. The system may determine the timing of the systole periods using historical information from previous cardiac cycles, from an external sensor, from user input, from measurements made with a different cardiac cycle modulation, by any other suitable technique, or any combination thereof. It will be understood that the system may align modulation with pulses of the heart, pulses of a particular muscle group, other suitable pulses, any other suitable physiological function, or any combination thereof. It will also be understood that modulation of the light drive signal (i.e., the "on" and "off" states illustrated by light drive signal 1110) is merely exemplary and may include modulation of parameters including drive current or light brightness, duty cycle, firing rate, modulation parameters, other suitable parameters, or any combination thereof. It will also be understood that the "on" and "off" states are merely exemplary and that the system may use any suitable number of discrete or continuous modulation variations.

Figure 12:
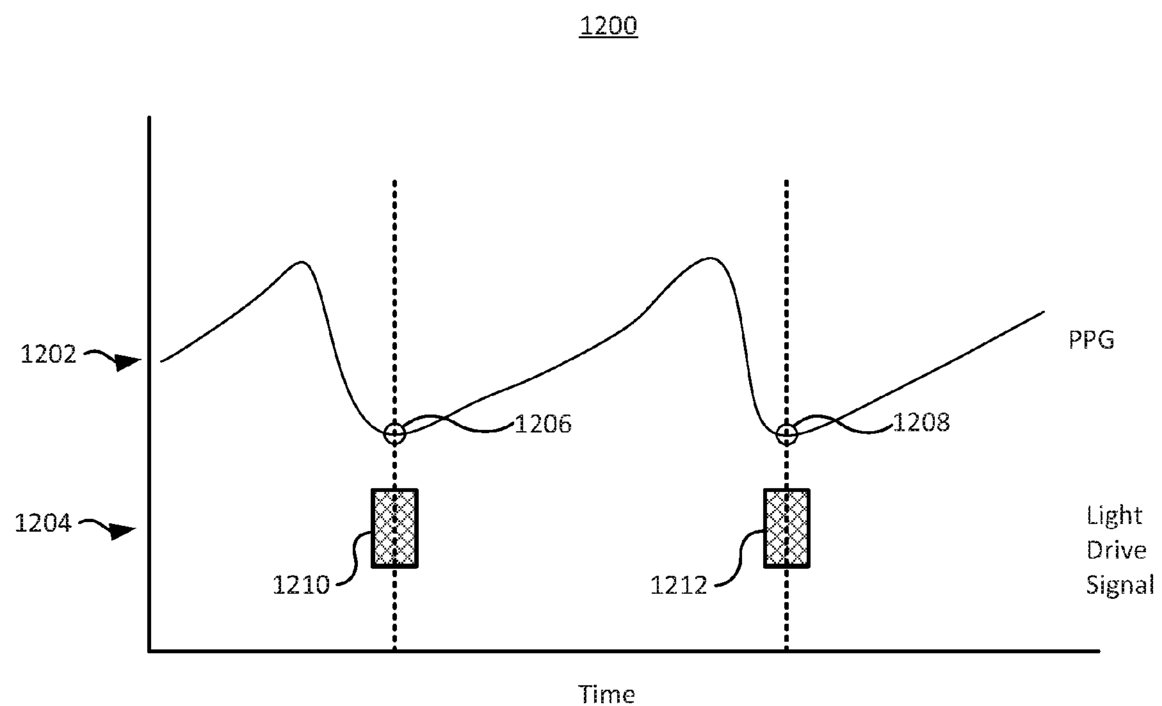
FIG. 12 shows another illustrative timing diagram of a physiological monitoring system in accordance with some embodiments of the present disclosure.

FIG. 12 shows another illustrative timing diagram 1200 of a physiological monitoring system in accordance with some embodiments of the present disclosure. In some embodiments, the system may vary a light drive signal such that a parameter is varied concurrent with peaks or troughs in the PPG signal. Timing diagram 1200 may include PPG signal 1202 and light drive signal 1204. PPG signal 1202 is shown with arbitrary units on the ordinate axis. Light drive signal 1204 is shown in "on" or "off" states without units associated with the ordinate axis. It will be understood that light drive signal 1204 may provide a light drive signal to one or more emitters. It will also be understood any suitable number of cardiac cycle modulation techniques may be used with any suitable number of emitters.

In some embodiments, the system may modulate light drive signal 1202 in a way related to the cardiac cycle. Light drive signal 1204 may correspond to the light drive signal generated at step 902 of FIG. 9. In some embodiments, the system may turn on a light drive signal for point 1206 and point 1208. In some embodiments, point 1206 and 1208 may represent peaks or troughs, depending on the orientation of the PPG signal. Thus, the cardiac cycle modulation applied to light drive signal 1204 may be substantially synchronous with the troughs of the PPG signal. In some embodiments, the PPG signal may be inverted such that the periods of interest as illustrated in plot 1200 are peaks. It will be understood that the system may identify periods of interest at any point in the cardiac cycle and that those illustrated in plot 1200 are merely exemplary. For example, periods of interest may include peaks, valleys, troughs, dicrotic notches, fiducial points, other suitable points, or any combination thereof. In some embodiments, the light drive signal may be in an "on" mode for both the peak and trough of a PPG signal, and in an "off" mode for the rising and falling portion of the PPG signal. In some embodiments, the system may turn on a light source before peaks 1206 and 1208 and turn off a light source following peaks 1206 and 1208 so that the photonic signal can stabilize, so that the detector can stabilize, so that the processing equipment can obtain extra samples for averaging, interpolating, or decimating, for amplifier gain adjustments to stabilize, for any other suitable reason, or any combination thereof. The system may determine the time offsets between the "on" periods and the region of interest based on user input, predetermined parameters, previous measurements, other suitable parameters, or any combination thereof. The system may determine the timing of the PPG peaks using information from previous cardiac cycles, from an external sensor, from user input, from measurements made with a different cardiac cycle modulation, by any other suitable technique, or any combination thereof. It will be understood that the system may align modulation with pulses of the heart, pulses of a particular muscle group, other suitable pulses, any other suitable physiological function, or any combination thereof. It will also be understood that modulation of the light drive signal (i.e., the "on" and "off" states illustrated by light drive signal 1204) is merely exemplary and may include modulation of parameters including drive current or light brightness, duty cycle, firing rate, modulation parameters, other suitable parameters, or any combination thereof. It will also be understood that the "on" and "off" states are merely exemplary and that the system may use any suitable number of discrete or continuous modulation variations.

Figure 13:
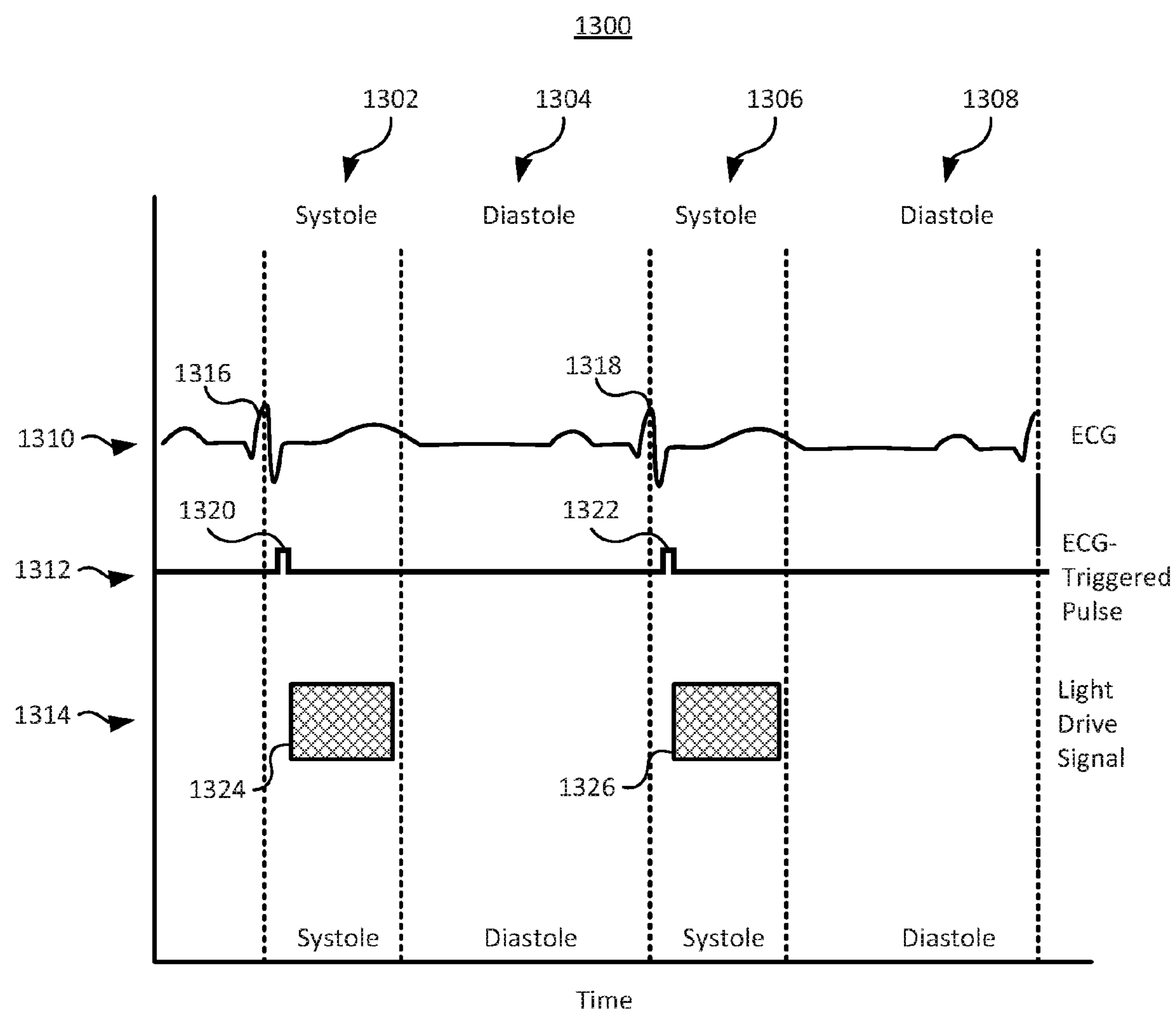
FIG. 13 shows another illustrative timing diagram of a physiological monitoring system in accordance with some embodiments of the present disclosure.

FIG. 13 shows another illustrative timing diagram 1300 of a physiological monitoring system in accordance with some embodiments of the present disclosure. In some embodiments, the system may vary a light drive signal such that a parameter is varied concurrent with receiving an external trigger, for example, an ECG. Timing diagram 1300 may include time periods related to the cardiac cycle, including systole period 1302, diastole period 1304, systole period 1306, and diastole period 1308. Timing diagram 1300 may include ECG signal 1310, ECG-triggered pulse signal 1312, and light drive signal 1314. ECG signal 1310 and ECG-triggered pulse signal 1312 are shown with arbitrary units on the ordinate axis. Light drive signal 1314 is shown in "on" or "off" states without units associated with the ordinate axis. It will be understood that light drive signal 1314 may provide a light drive signal to one or more emitters. It will also be understood any suitable number of cardiac cycle modulation techniques may be used with any suitable number of emitters.

In some embodiments, the system may modulate light drive signal 1314 in a way related to the cardiac cycle. Light drive signal 1314 may correspond to the light drive signal generated at step 902 of FIG. 9. In some embodiments, the system may receive ECG signal 1310 from an ECG sensor, from an external system, from any other suitable source, or any combination thereof. The system may process the ECG signal to determine a point of interest in the ECG signal. For example, the system may identify R wave peaks 1316 and 1318 in ECG signal 1310. In some embodiments, the systole period may begin at a time substantially correlated to the R wave peak. It will be understood that any suitable feature of any suitable external signal may be used to trigger changes in light drive signal modulation. For example, other features of the ECG may be identified. In a further example, a time offset from a particular ECG signal feature may correlate the cardiac cycle modulation with a desired cardiac cycle feature (e.g., a particular number of milliseconds in advance or delay of a particular ECG feature). In a further example, the system may identify features of other external signals such as an EEG, respiration rate, any other suitable signal, or any combination thereof.

The system may generate ECG-triggered pulse signal 1312 including a signal pulse 1320 substantially concurrent with R wave peak 1316 and signal pulse 1322 substantially concurrent with R wave peak 1318. In some embodiments, the system may determine the timing of the ECG-triggered pulse cycles using historical information from previous cardiac cycles in addition to the instant pulse cycle. In some embodiments, the system may receive only ECG-triggered pulse signal 1312 (i.e., the ECG-triggered pulse signal may be generated by an external system). In some embodiments, the system may generate ECG-triggered pulse signal 1312. In some embodiments, the system may receive ECG-triggered pulse signal 1312 from user input or from an external processing device not related to the ECG. In some embodiments, the system may modulate light drive signal 1314 in a way correlated to ECG-triggered pulse signal 1312, ECG signal 1310, any other suitable signal, or any combination thereof. For example, the system may change light drive signal 1314 during period 1324 to an "on" state in response to signal pulse 1320 and during period 1326 to an "on" state in response to signal pulse 1322. In some embodiments, the system may delay or advance periods 1324 and 1326 in relation to signal pulses 1320 and 1322, respectively. For example, the system may delay or advance the "on" state of the light drive signal to account for a delay between the ECG signal measured near the heart and the features of a PPG signal measured by a sensor remote from the heart (e.g., on a digit). In some embodiments, multiple signal pulses or multiple pulse signals (not shown) may be used to change the state of the light drive signal. For example, the system may receive a second signal pulse associated with a physiological parameter to turn the light drive signal to an "off" state. In some embodiments, the duration of the "on" state following a signal pulse (e.g., signal pulse 1320) may be a predetermined length of time, a length of time determined by previous measurements, a length of time determined by data collected during previous periods, a length of time set by user input, a length of time determined by any other suitable technique, or any combination thereof.

It will be understood that the system may align light drive signal modulation with pulses of the heart, pulses of a particular muscle group, other suitable pulses, any other suitable physiological function, or any combination thereof. It will also be understood that modulation of the light drive signal (i.e., the "on" and "off" states illustrated by light drive signal 1314) is merely exemplary and may include modulation of parameters including drive current or light brightness, duty cycle, firing rate, modulation parameters, other suitable parameters, or any combination thereof. It will also be understood that the "on" and "off" states are merely exemplary and that the system may use any suitable number of discrete or continuous modulation variations.

Figure 14:
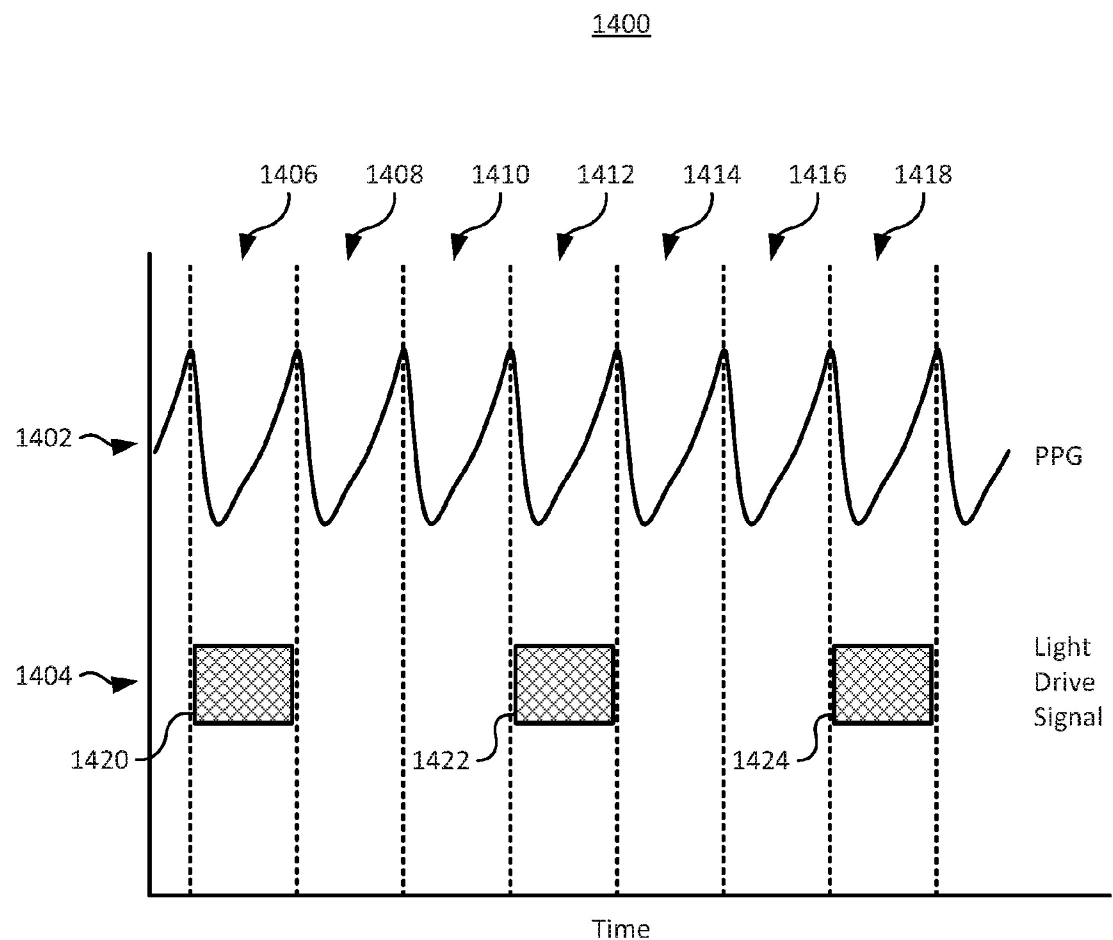
FIG. 14 shows another illustrative timing diagram of a physiological monitoring system in accordance with some embodiments of the present disclosure.

FIG. 14 shows another illustrative timing diagram 1400 of a physiological monitoring system in accordance with some embodiments of the present disclosure. In some embodiments, the system may vary the light drive signal using a technique that skips cardiac cycles. Timing diagram 1400 may include time periods related to the cardiac cycle, including pulse cycles 1406, 1408, 1410, 1412, 1414, 1416, and 1418. Timing diagram 1400 may include PPG signal 1402, and light drive signal 1404. PPG signal 1402 is shown with arbitrary units on the ordinate axis. Light drive signal 1404 is shown in "on" or "off" states without units associated with the ordinate axis. It will be understood that light drive signal 1404 may provide a light drive signal to one or more emitters. It will also be understood any suitable number of cardiac cycle modulation techniques may be used with any suitable number of emitters.

The system may vary the light drive signal in a way correlated to the cardiac pulse signal of the subject. The system may generate an "on" light drive signal during one or more cardiac cycles and an "off" light drive signal during one or more cardiac cycles. For example, the system may generate an "on" light drive signal during period 1420 concurrent with pulse cycle 1406, an "off" light drive signal during pulse cycles 1408 and 1410, an "on" light drive signal during period 1422 concurrent with pulse cycle 1412, an "off" light drive signal during pulse cycles 1414 and 1416, and an "on" light drive signal during period 1424 concurrent with pulse cycle 1418. It will be understood that this particular modulation is merely exemplary and that any suitable inter-cycle modulation may be used.

In some embodiments, the system may use an intra-cardiac cycle modulation as described above during "on" periods 1420, 1422, and 1424 of the inter-cardiac cycle modulation illustrated in timing diagram 1400. For example, the system may emit light during any suitable intra-cycle period (e.g., systole period, diastole period, peak, etc.) of pulse cycle 1406, 1412, and 1418, as described in flow diagram 900 of FIG. 9. In some embodiments, the system may emit light from a first light source during the "off" cardiac cycles and emit light from a second light source during the "on" periods (or a portion of the "on" periods), such that information related to the first light source is used to determine when to generate the second light drive signal as described in flow diagram 400 of FIG. 4.

The system may determine the timing of the cardiac cycles using historical information from previous cardiac cycles, from an external sensor, from user input, from measurements made with a different cardiac cycle modulation, by any other suitable technique, or any combination thereof. It will be understood that the system may align modulation with pulses of the heart, pulses of a particular muscle group, other suitable pulses, any other suitable physiological function, or any combination thereof. It will also be understood that modulation of the light drive signal (i.e., the "on" and "off" states illustrated by light drive signal 1110) is merely exemplary and may include modulation of parameters including drive current or light brightness, duty cycle, firing rate, modulation parameters, other suitable parameters, or any combination thereof. It will also be understood that the "on" and "off" states are merely exemplary and that the system may use any suitable number of discrete or continuous modulation variations.

Figure 15:
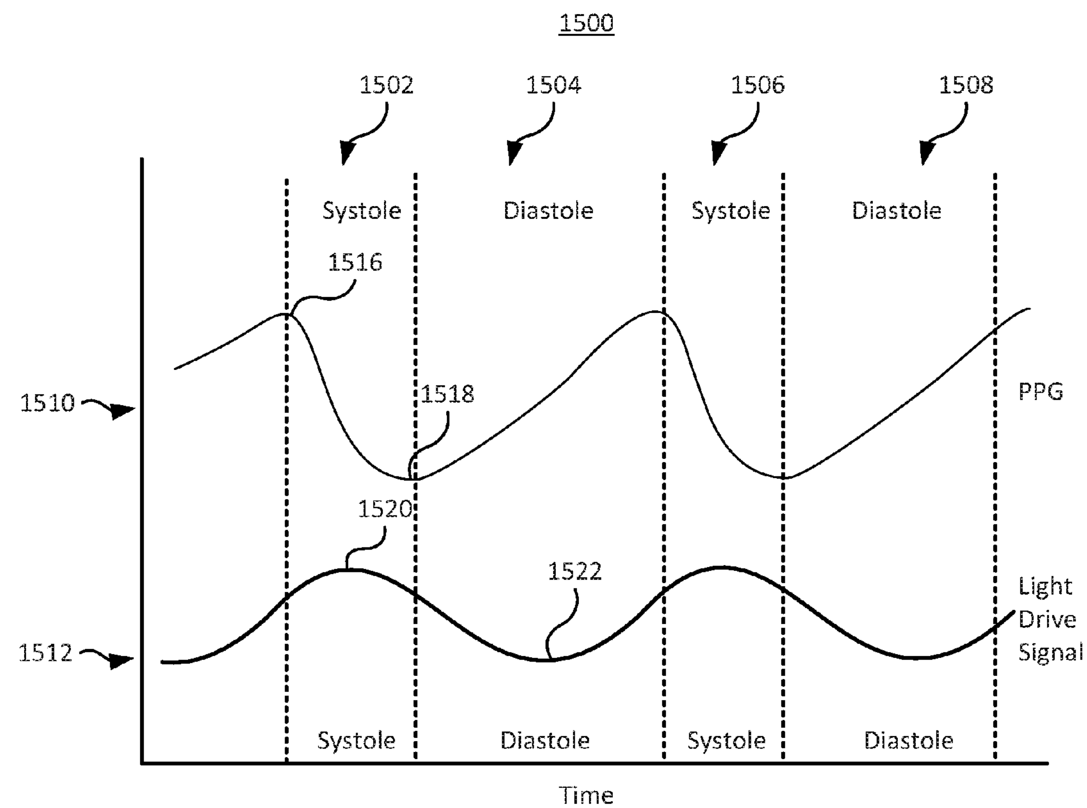
FIG. 15 shows another illustrative timing diagram of a physiological monitoring system in accordance with some embodiments of the present disclosure.

FIG. 15 shows another illustrative timing diagram 1500 of a physiological monitoring system in accordance with some embodiments of the present disclosure. In some embodiments, the system may vary a light drive signal such that a parameter is varied continuously according to a periodic waveform. Timing diagram 1500 may include time periods related to the cardiac cycle, including systole period 1502, diastole period 1504, systole period 1506, and diastole period 1508. Timing diagram 1500 may include PPG signal 1510 and light drive signal 1512, shown with arbitrary units on the ordinate axis. It will be understood that light drive signal 1512 may provide a light drive signal to one or more emitters. It will also be understood any suitable number of cardiac cycle modulation techniques may be used with any suitable number of emitters.

In some embodiments, the system may modulate light drive signal 1512 in a way related to the cardiac cycle. Light drive signal 1512 may correspond to the light drive signal generated at step 902 of FIG. 9. In some embodiments, the system may apply a waveform modulation to light drive signal 1512 such that the waveform maxima are substantially aligned with a cardiac cycle feature. For example, the system may align peak 1520 of light drive signal 1512 with systole period 1502. The amplitude of light drive signal 1512 may relate to drive current or light brightness, duty cycle, firing rate, modulation parameters, other suitable parameters, or any combination thereof. In some embodiments, the system may superimpose the amplitude of light drive signal 1512 as a cardiac cycle modulation envelope function on the amplitudes of a drive cycle modulation.

In some embodiments, the system may determine the position of systole period 1502 using PPG signal 1510. For example, the system may apply a time offset to PPG peak 1516 or PPG trough 1518 to determine the center of the systole period, and the system may adjust the light drive signal such that peak 1520 is aligned with the center of the systole period. It will be understood that the system may align any suitable feature of the waveform of light drive signal 1512 with any one or more suitable features of the cardiac cycle. For example, the waveform may be aligned such that peak 1520 is correlated with diastole period 1504. In some embodiments, the waveform may be aligned with features of the PPG signal. For example, peak 1520 may be aligned with peak 1516, trough 1518, or a dicrotic notch (not shown). It will be understood that these alignments are merely exemplary and that any suitable feature of one signal may be aligned with any suitable feature of the other.

In some embodiments, the system may modulate light drive signal 1512 with any suitable periodic waveform, for example, a square wave, triangle wave, sawtooth wave, sinusoidal wave, any other suitable wave, or any combination thereof. In some embodiments, continuous periodic waveforms may be preferable to discontinuous waveform (e.g., square waves) with regards to further processing steps. In some embodiments, the system may determine the alignment of the waveform using information from previous cardiac cycles, from an external sensor, from user input, from measurements made with a different cardiac cycle modulation, by any other suitable technique, or any combination thereof. It will be understood that the system may align modulation with pulses of the heart, pulses of a particular muscle group, other suitable pulses, any other suitable physiological function, or any combination thereof. It will be understood that the system may implement cardiac cycle modulations in addition to drive cycle modulations and conventional servo algorithms. It will be understood that the amplitudes of light drive signal 1512 may represent amplitudes of any suitable cardiac cycle modulation parameter, as described above. For example, amplitudes of light drive signal 1512 may relate to parameters including drive current or light brightness, duty cycle, firing rate, modulation parameters, other suitable parameters, or any combination thereof.

Figure 16:
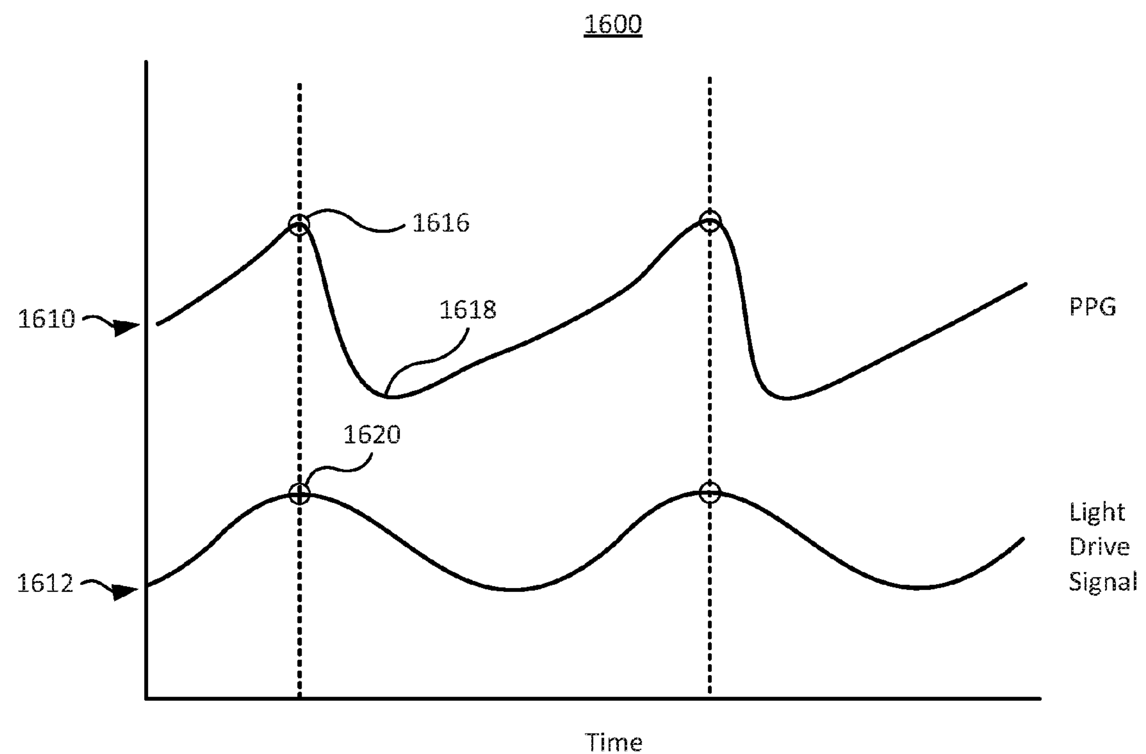
FIG. 16 shows another illustrative timing diagram of a physiological monitoring system in accordance with some embodiments of the present disclosure.

FIG. 16 shows another illustrative timing diagram 1600 of a physiological monitoring system in accordance with some embodiments of the present disclosure. In some embodiments, the system may vary a light drive signal such that a parameter is varied continuously according to a periodic waveform. Timing diagram 1600 may include PPG signal 1610 and light drive signal 1612, shown with arbitrary units on the ordinate axis. It will be understood that light drive signal 1612 may provide a light drive signal to one or more emitters. It will also be understood any suitable number of cardiac cycle modulation techniques may be used with any suitable number of emitters.

In some embodiments, the system may modulate light drive signal 1612 in a way related to the cardiac cycle. Light drive signal 1612 may correspond to the light drive signal generated at step 902 of FIG. 9. In some embodiments, the system may apply a waveform modulation to light drive signal 1612 such that the waveform maxima are substantially aligned with a cardiac cycle feature. For example, the system may align peak 1620 of light drive signal 1612 with peak 1616 in PPG signal 1610. In another embodiment, the system may align peak 1620 of light drive signal 1612 with PPG trough 1618, a dicrotic notch, a fiducial point, any other suitable feature, or any combination thereof. It will be understood that these alignments are merely exemplary and that any suitable feature of one signal may be aligned with any suitable feature of the other. For example, the system may apply a time offset to PPG peak 1616 or PPG trough 1618 to determine the desired location of peak 1620.

The system may determine the timing of the cardiac cycles using historical information from previous cardiac cycles, from an external sensor, from user input, from measurements made with a different cardiac cycle modulation, by any other suitable technique, or any combination thereof. It will be understood that the system may align modulation with pulses of the heart, pulses of a particular muscle group, other suitable pulses, any other suitable physiological function, or any combination thereof. It will also be understood that modulation of the light drive signal (i.e., the "on" and "off" states illustrated by light drive signal 1612) is merely exemplary and may include modulation of parameters including drive current or light brightness, duty cycle, firing rate, modulation parameters, other suitable parameters, or any combination thereof. It will also be understood that the "on" and "off" states are merely exemplary and that the system may use any suitable number of discrete or continuous modulation variations.

Figure 17:
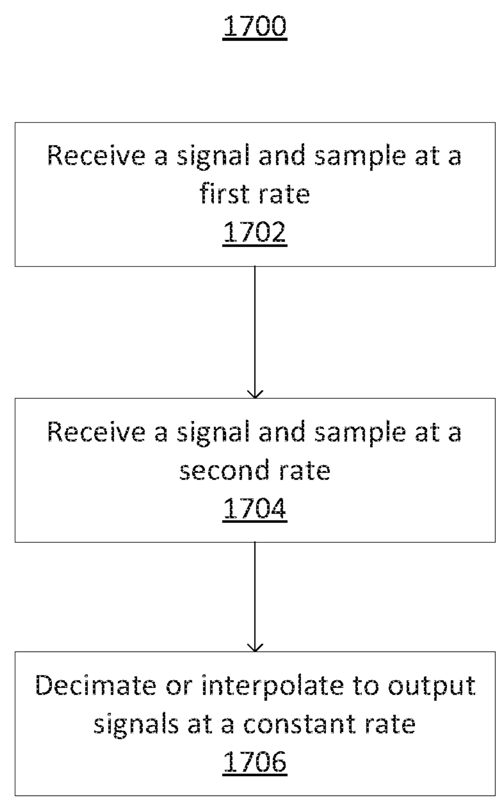
FIG. 17 is a flow diagram showing illustrative steps for decimating and interpolating a signal in accordance with some embodiments of the present disclosure.

FIG. 17 is flow diagram 1700 showing illustrative steps for decimating and interpolating a signal in accordance with some embodiments of the present disclosure. In some embodiments, the system may sample a signal at different rates throughout a cardiac cycle. The system may process the sampled signal to produce an output signal with a constant rate. In some embodiments, the system may vary the sampling rate to reduce or optimize power consumption. In some embodiments, sampling rate modulation may be correlated with light drive signal modulation. Varying the sampling rate may reduce power consumption by reducing emitter drive time and lowering utilization of an analog-to-digital converter. In some embodiments, varying the sampling rate may increase the time resolution of identified features. For example, in a continuous non-invasive blood pressure measurement where the pulse transit time is used in calculations, increasing the sampling rate for a portion of the cardiac cycle may result in more accurate and reliable physiological information. In another example, varying the sampling rate around a cardiac pulse cycle feature, such as a peak or notch, may increase the accuracy of determining the location of that feature in time. In some embodiments, lower frequency or less critical parts of the cardiac pulse cycle may be sampled at a lower rate while maintaining highly accuracy and reliable physiological parameter determination.

In step 1702, the system may receive a signal. The signal may be sampled at a first rate. The signal may be sampled using an analog-to-digital converter in the front end processing circuitry. For example, an attenuated light signal may be converted to an analog electronic signal by a detector. The analog electronic signal may be converted to a digital signal at a particular rate by an analog to digital converter, such that at each sampling point the converter determines the amplitude of the analog signal (e.g., current or voltage) and outputs a digital word related to that amplitude. The rate at which sampling occurs may be controlled by, for example, a timing control signal (e.g., provided by control circuitry 110 of FIG. 1). In some embodiments, the sampling rate may represent the number of samples taken during an "on" period of the drive cycle modulation. In some embodiments, the sampling rate may represent the amount of time between "on" periods.

In step 1704, the system may receive a signal and sample it at a second sampling rate. For example, the period between samples may be increased or reduced. In some embodiments, this may relate to a higher resolution digitization of an analog signal. In some embodiments, changes in the sampling period may vary continuously according to some predetermined periodic waveform, may change as a step functions, may be varied by any other suitable technique, or any combination thereof. In some embodiments, the system may store, communicate, or otherwise utilize the sampling rate along with the digitized sample. The sampling rate may be used in subsequent processing steps.

In step 1706, the system may decimate or interpolate the received signals to output signals at a constant rate. In some embodiments, it may be desirable for further processing to make the sampling rate constant throughout a signal. In some embodiments, the system may select the first and second sampling rates to ease or improve the interpolation and decimation of step 1706. For example, the second rate may be an integer multiple of the first rate.

The system may increase the sampling rate at a particular region in a signal by interpolation. Interpolation may add additional samples using information from the existing samples. For example, a data point may be added between two existing data points by calculating a mathematical average of the existing data. The system may use more complex interpolation schemes such as linear interpolation, polynomial interpolation, spline interpolation, any other suitable interpolation scheme, or any combination thereof. Interpolation may include upsampling, where zero valued segments are inserted into the digital signal. Upsampling may be followed by filtering to smooth the output. In some embodiments, filtering may be carried out by processing equipment discrete from sampling processing equipment, by integrated processing equipment, or any combination thereof. Interpolation may be carried out using hardware equipment, software equipment, or any combination thereof.

The system may decrease the sampling rate at a particular region in a signal by decimation. Decimation may decrease the sampling rate by removing samples from a signal. Decimation techniques may include downsampling, where segments of a sample are removed. Downsampling may include or be followed by filtering to smooth the output signal. It will be understood that a decimated signal originally sampled at a higher sampling rate may provide improved data as compared to a signal initially sampled at a lower rate. In some embodiments, interpolation may be used to decrease the sampling rate. For example, interpolation may decrease the sampling rate by replacing samples in a signal with a smaller number of samples.

The desired sampling rate may be determined based on the highest sampling rate available in the samples, the lowest sampling rate available in the samples, the downstream processing equipment, any other suitable determining factors, or any combination thereof. In some embodiments, a signal may be decimated, interpolated, or both, depending on the sampling rates used throughout and the desired output sampling rate. It will be understood that the output rate may not be a constant rate. It will also be understood that sampling rate is one of the components that may be modulated in cardiac cycle modulation as described above. It will also be understood that the earlier described embodiments relating to varying light output may also apply to sampling rate.

In some embodiments, the sampling rate may represent the number of samples taken during an "on" period of the drive cycle modulation. For example, an "on" period may be "on" period 202 of FIG. 2A. The system may sample that drive cycle modulation "on" period a lower number of times at a low sampling rate, and a greater number of times at a high sampling rate. In this embodiment, the firing rate of the emitters may not be modulated along with the analog-to-digital sampling rate. For example, at a low sampling rate, the system may sample once per "on" period, while at a high sampling rate the system may take several samples per "on" period and average them. In some embodiments, averaging multiple samples for the same "on" period may include oversampling techniques.

In some embodiments, the sampling rate may represent the amount of time between "on" periods. For example, the time between "on" periods may be the length of time of "off" period 220 of FIG. 2A. Increasing the duration of the "off" periods (i.e., decreasing the emitter firing rate) relates to a decreased sampling rate. Similarly, decreasing the duration of the "off" periods (i.e., increasing the emitter firing rate) relates to an increased sampling rate.

Figure 18:
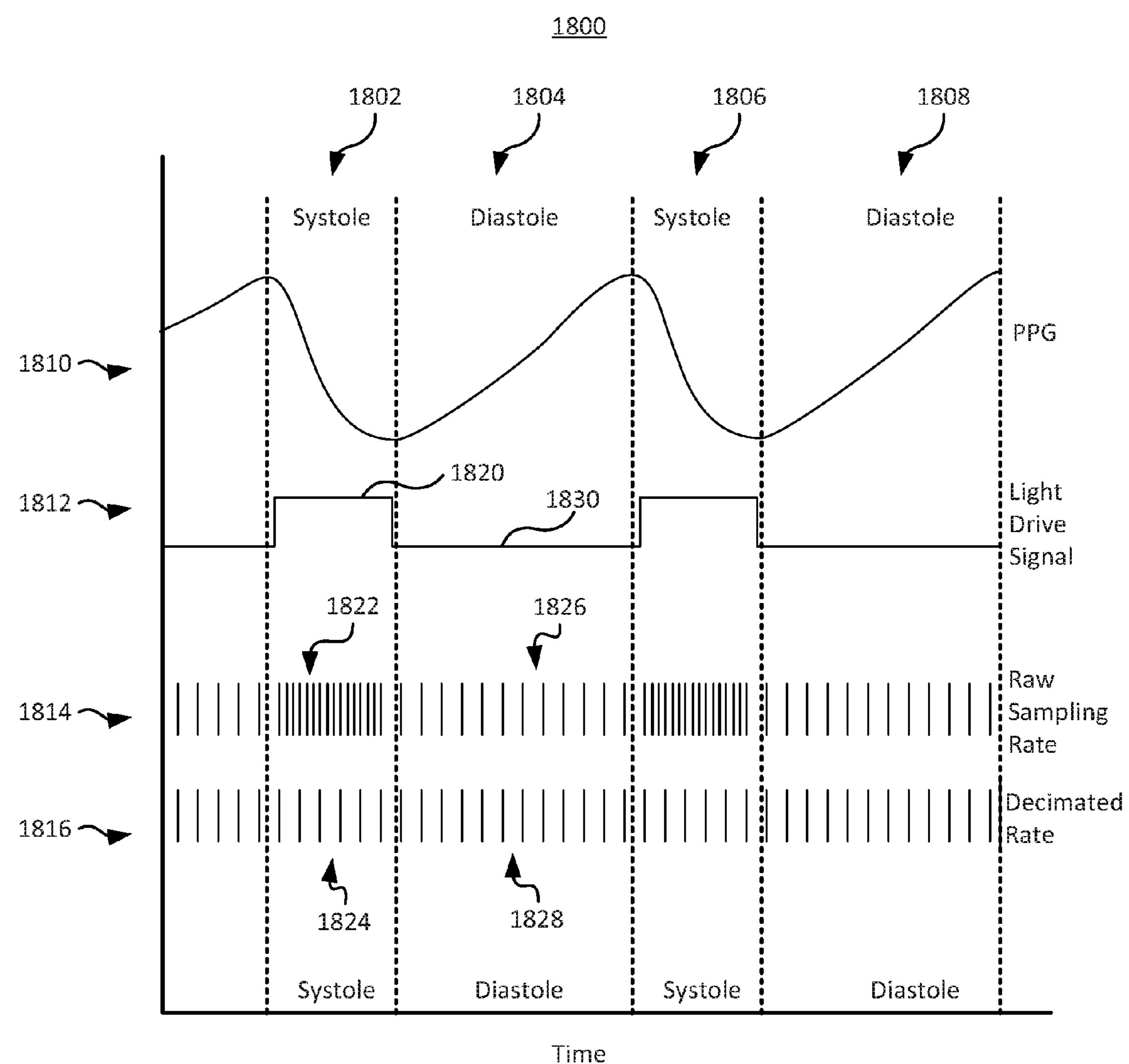
FIG. 18 shows an illustrative timing diagram of a physiological monitoring system including sampling rate variation in accordance with some embodiments of the present disclosure.

FIG. 18 shows an illustrative timing diagram of a physiological monitoring system including sampling rate variation in accordance with some embodiments of the present disclosure. Plot 1800 may include systole periods 1802 and 1806, and diastole periods 1804 and 1808. Plot 1800 may include PPG signal 1810, light drive signal 1812, raw sampling rate signal 1814, and decimated sampling rate signal 1816.

The vertical lines illustrated in raw sampling rate signal 1814 and decimated sampling rate signal 1816 may be indicative of individual samples, or a representative sampling rate, as described above. Thus, an increased number of vertical lines in a region may be indicative of a relatively higher sampling rate, while a decreased number of vertical lines in a region may be indicative of a relatively lower sampling rate. The system may vary other cardiac cycle modulation parameters along with sampling rate. For example, as illustrated by light drive signal 1812, the system may sample at a high rate during high light drive signal period 1820, as indicated by high raw sampling rate period 1822 and sample at a low rate during lower during a low light output drive signal 1830, as indicated by low raw sampling rate period 1826. The amplitude of light drive signal 1812 may relate to modulation of parameters including drive current or light brightness, duty cycle, firing rate, modulation parameters, other suitable parameters, or any combination thereof. It will be understood that the square wave modulation of light drive signal 1812 is merely exemplary and that any suitable modulation technique may be used.

In the example illustrated in plot 1800, the high light drive signal period 1820 is substantially aligned with systole period 1802, though it will be understood that the system may use any suitable cardiac cycle modulation technique and may correlate modulation features with any suitable signal elements. The system may use a relatively high raw sampling rate period 1822 for a period substantially aligned with high light drive signal period 1820. The system may use a relatively low raw sampling rate period 1826 for a period substantially aligned with low light drive signal period 1830.

In some embodiments, the system may use a high sampling rate during the high light output periods and a low sampling rate during low light output periods to reduce power consumption while still obtaining high quality determinations of physiological parameters. It will be understood that the particular sampling rates shown in plot 1800 are merely exemplary and that the system may employ any suitable sampling rate and any suitable sampling rate modulation.

In some embodiments, the system may process raw sampling rate signal 1814 to produce decimated sampling rate signal 1816 by decimation, interpolation, any other suitable sampling rate modification, or any combination thereof. As used herein, "raw" refers to the sampling rate at the analog-to-digital converter prior to interpolation or decimation. It will be understood that the system may decimate and interpolate samples using any suitable hardware technique, software technique, or any combination thereof.

In the example illustrated in plot 1800, the raw sampling rate signal 1814 during high raw sampling rate period 1822 is decimated to a lower sampling rate in one or more processing steps to produce decimated sampling rate signal 1816 in sampling rate period 1824. Low sampling rate period 1826 of raw sampling rate signal 1814 is kept the same in sampling rate period 1828 of decimated sampling rate signal 1816. Thus, while the sampling rate in raw sampling rate signal 1814 varies throughout the cardiac cycle, the sampling rate in the decimated sampling rate signal 1816 is constant throughout the cardiac cycle. In another embodiment (not shown), the sampling during low sampling rate period 1826 may be interpolated to increase the sampling rate to match that of high sampling rate period 1822 to produce a decimated sampling rate signal 1816 with a constant sampling rate. In another embodiment, sampling rates may be decimated, interpolated, or a combination thereof to achieve a constant sampling rate in decimated sampling rate signal 1816.

In some embodiments, the system may alter sampling rate modulation, sampling rate decimation, and sampling rate interpolation to optimize power consumption. For example, the system may use a modulated method when powered by battery power and a constant sampling rate when powered by an external power source. In some embodiments, the sampling rate may be modulated using a step function (as illustrated in FIG. 18), by multiple step functions, by a periodic continuous function, by any other suitable modulation, or any combination thereof.

Figure 19:
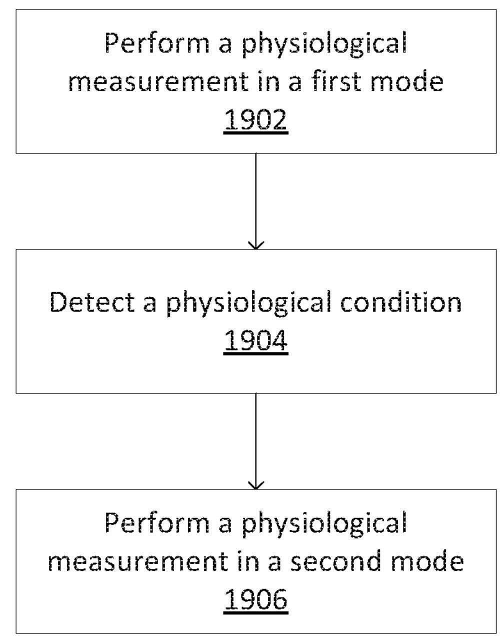
FIG. 19 is a flow chart showing steps to adjust a cardiac cycle modulation based on a physiological condition in accordance with some embodiments of the present disclosure.

FIG. 19 is flow chart 1900 showing steps to adjust a cardiac cycle modulation based on a physiological condition in accordance with some embodiments of the present disclosure.

In step 1902, the system may perform a physiological measurement in a first mode. The first mode may be, for example, a first cardiac cycle modulation technique.

In step 1904, the system may detect a physiological condition. For example, the system may detect dysrhythmia, arrhythmia, fibrillation, non-periodic heartbeat, tachycardia, other cardiac irregularity, or any combination thereof. The system may also detect no heartbeat. In some embodiments, the system may false-positive detect a physiological condition in the presence of noise, ambient light, a loss of detector signal, any other suitable reason, or any combination thereof. In some embodiments, the system may detect a physiological parameter, for example, a low blood oxygen saturation, low pulse rate, high pulse rate, high blood pressure, low blood pressure, any other suitable condition, or any combination thereof. In some embodiments, the system may detect a signal indicative of a system error such as a physiologically impossible value, a probe-off signal, any other suitable signal, or any combination thereof. The system may detect the physiological condition using information obtained through measurements in step 1902, from an external sensor or controller, by any other suitable technique, or any combination thereof.

In some embodiments, the system may detect a condition where a second mode is required that is not related to a physiological condition. For example, the system may detect a change in background noise, a change in ambient light, a change in the available power, other suitable changes, or any combination thereof. In some embodiments, an increase in the number of identified fiducial points (e.g., zero crossings of the derivatives) may cause the system to vary drive signals.

In step 1906, the system may perform a physiological measurement in a second mode. For example, the system may stop cardiac cycle modulation and emit light at a constant brightness. In a further example, the system may increase the emitter intensity used in a cardiac cycle modulation. In a further example, the system may lengthen the "on" periods of a cardiac cycle modulation. In a further example, the system may alter the cardiac cycle modulation technique as described above with relation to FIG. 8B. In some embodiments, a non-periodic heartbeat may make cardiac cycle modulation not desirable or not possible. In some embodiments, the system may return to the first mode after the detected physiological condition ceases, after a predetermined time period, after receiving user input, after any other suitable command, or any combination thereof. In some embodiments, when performing the measurement in a second mode, the system may also notify the user by an alarm, by a display, by any other suitable notification technique, or any combination thereof.

Figure 20:
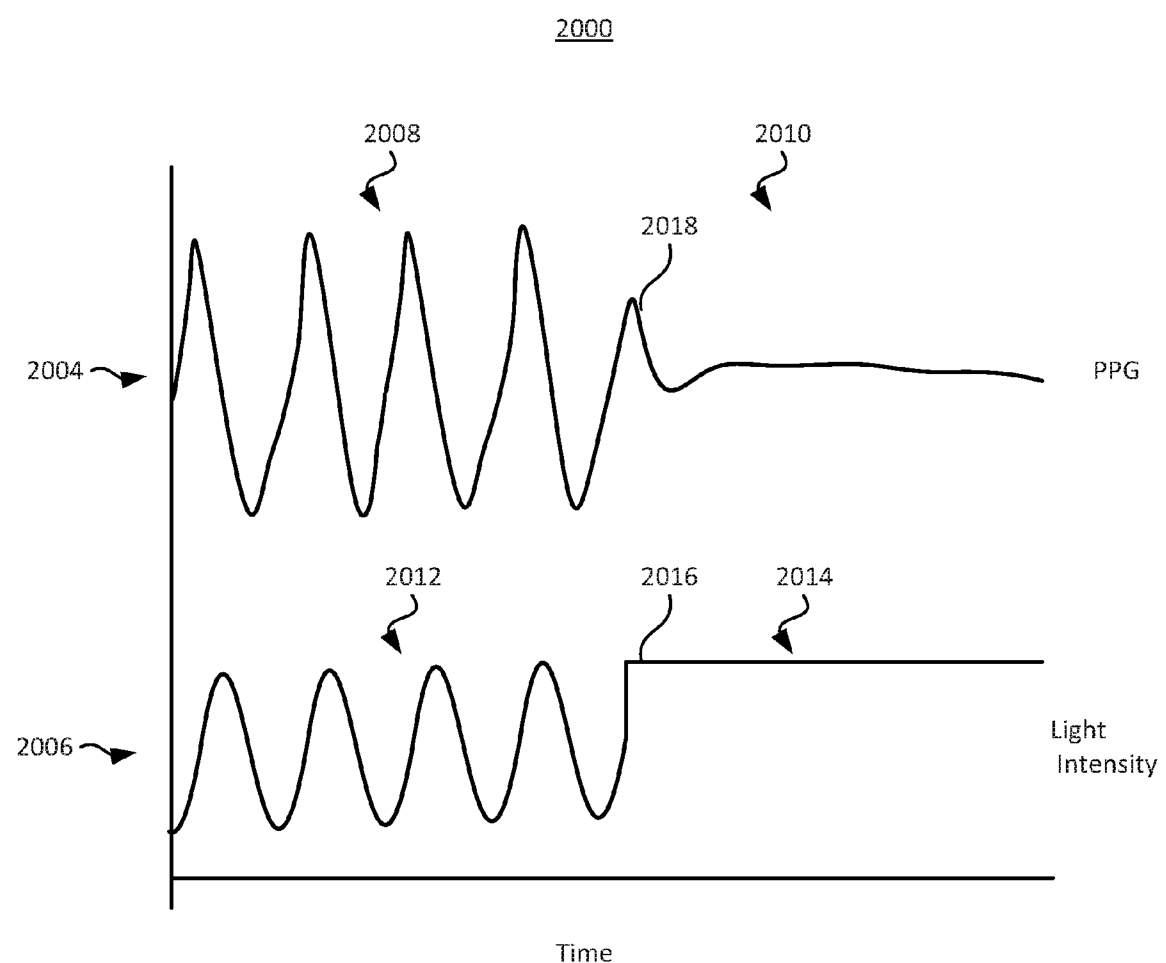
FIG. 20 is an illustrative timing diagram of a system operating in a first and second mode following detection of a physiological condition in accordance with some embodiments of the present disclosure.

FIG. 20 is illustrative timing diagram 2000 of a system operating in a first and second mode following detection of a physiological condition in accordance with some embodiments of the present disclosure. Plot 2000 may include PPG signal 2004 and cardiac cycle modulation 2006. PPG signal 2004 may include normal cardiac waveform period 2008 and abnormal cardiac waveform period 2010. For example, abnormal cardiac waveform period 2010 may include the heart ceasing to beat (i.e., "flatline") or entering a cardiac dysrhythmia (e.g., ventricular fibrillation, atrial fibrillation, AV blockage). At point 2018, the system may detect in PPG signal 2004 the beginning of abnormal cardiac waveform period 2010. As described above, the system may detect abnormal cardiac waveform period 2010 by processing PPG signal 2004 during normal cardiac internal 2008, by an external trigger, from any other suitable input, or any combination thereof. In some embodiments, the system may output light using cardiac cycle modulation 2006. For example, the system may output light or vary any suitable light drive signal component with sinusoidal modulation during period 2012 substantially aligned with normal cardiac operation period 2008. The system may change the cardiac cycle modulation technique at point 2016 based on the abnormal cardiac waveform identified at point 2018. For example, the system may output light at constant brightness during period 2014 substantially aligned with abnormal cardiac waveform period 2010. It will be understood that sinusoidal modulation 2012 is merely exemplary and that the system may use any suitable modulation technique. It will also be understood that there may be a time offset between identifying the abnormal cardiac waveform at point 2018 and modifying the modulation technique at point 2016, and that the delay illustrated in plot 2000 is merely exemplary.

Figure 21:
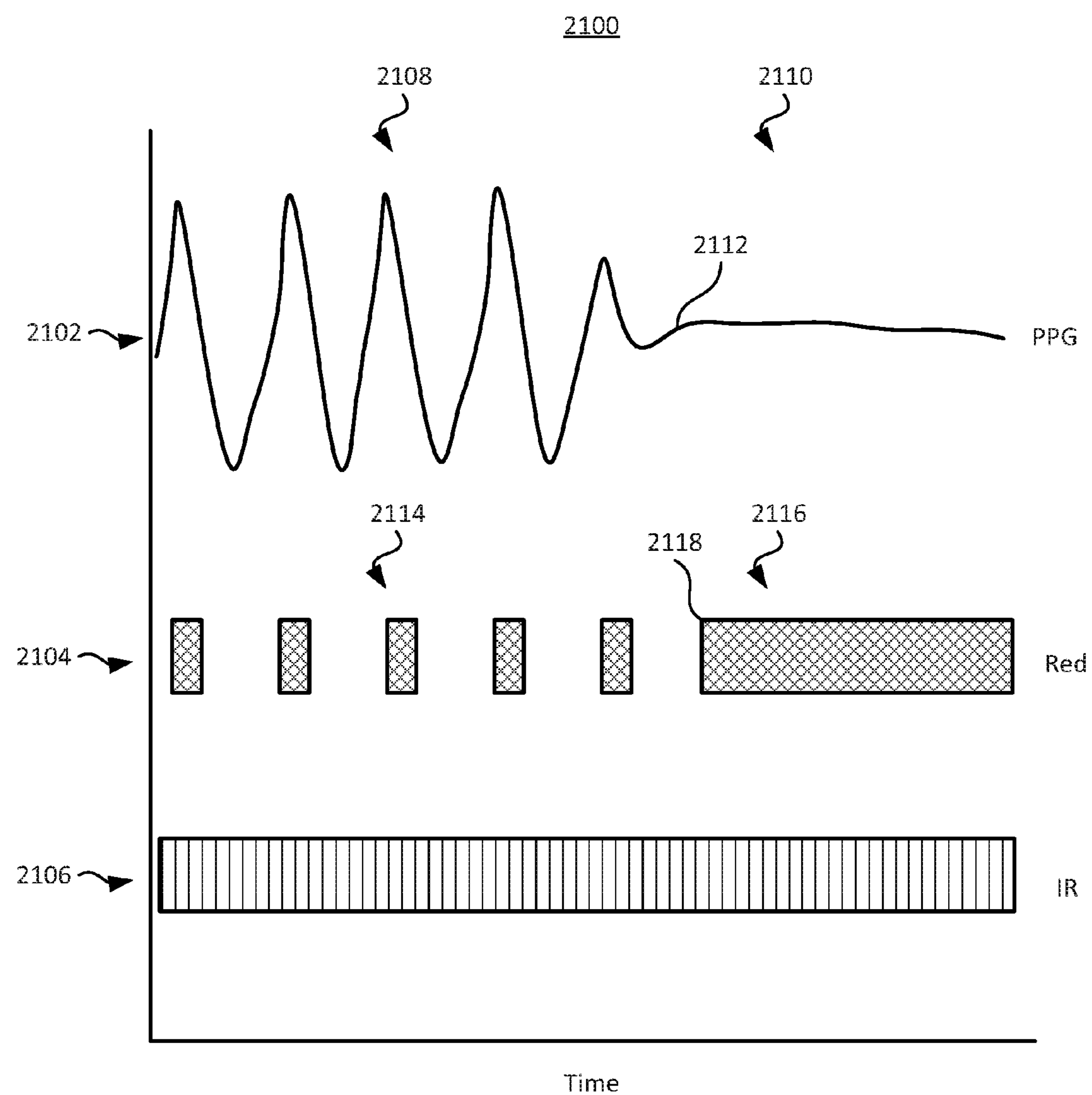
FIG. 21 is another illustrative timing diagram of a system operating in a first and second mode following detection of a physiological condition in accordance with some embodiments of the present disclosure.

FIG. 21 is another illustrative timing diagram 2100 of a system operating in a first and second mode following detection of a physiological condition in accordance with some embodiments of the present disclosure. Plot 2100 may include PPG signal 2102, red light drive signal 2104 and IR light drive signal 2016. PPG signal 2102 may include normal cardiac waveform period 2108 and abnormal cardiac waveform period 2110. For example, abnormal cardiac waveform period 2110 may include the heart ceasing to beat or entering a cardiac dysrhythmia. At point 2112, the system may detect in PPG signal 2102 the start of abnormal cardiac waveform period 2110. As described above, the system may detect abnormal cardiac waveform period 2110 by processing PPG signal 2102 during normal cardiac waveform interval 2108, by an external trigger, from any other suitable input, or any combination thereof. In some embodiments, the system may output light using a cardiac cycle modulation shown by red light drive signal 2104 and IR light drive signal 2016. For example, the system may output IR light with a constant output, as indicated by the solid block of IR light drive signal 2016. The system may modulate red light output with a square wave, as indicated by the broken blocks of red light drive signal 2104 in modulated light period 2114. The system may change the cardiac cycle modulation technique at point 2118 based on the abnormal cardiac waveform identified at point 2112 in PPG 2102. For example, the system may output light at constant brightness during period 2116 substantially aligned with abnormal cardiac waveform period 2110. In a further example, where in the first mode the system emits light from a first light source at a constant rate and a modulated intensity from a second light source, the system may switch to a constant brightness for both the first and second light sources. It will be understood that the square wave modulation of modulated light period 2114 is merely exemplary and that the system may use any suitable modulation technique. It will also be understood that there may be a time delay between identifying the abnormal cardiac operation at point 2112 and modifying the modulation technique at point 2118, and that the delay illustrated in plot 2100 is merely exemplary.

Figure 22:
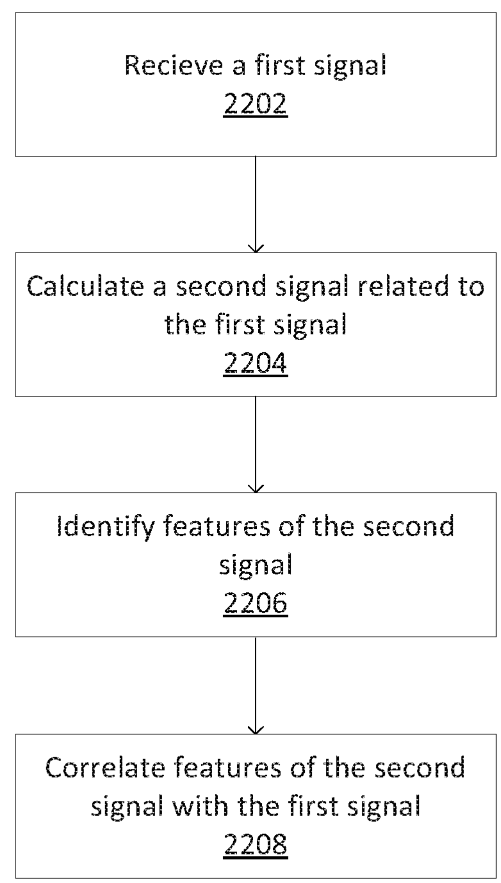
FIG. 22 is a flow diagram showing illustrative steps for identifying features in a signal in accordance with some embodiments of the present disclosure.

FIG. 22 is flow diagram 2200 showing illustrative steps for identifying features in a signal in accordance with some embodiments of the present disclosure. In some embodiments, the system may perform processing steps to identify points of interest in a signal. The signal may be, for example, a received attenuated photonic signal. In some embodiments, the system may use the identified points of interest in adjusting cardiac cycle modulation. Identified points of interest may include local maxima and minima of a PPG signal, fiducial points, any other suitable points, or any combination thereof. In some embodiments, identification of fiducials may be intra-channel, where information from a signal is used to identify fiducials in that signal. In some embodiments, identification of fiducial may be inter-channel, where information from a first signal is used to identify fiducials in a second signal. The system may use any suitable combination of inter-channel and intra-channel identification techniques. The selection of an inter-channel or intra-channel identification technique may depend, in part, on the light sources and the cardiac cycle modulation technique.

In step 2202, the system may receive a signal. The signal may be, for example, an attenuated photonic signal. The signal may have been detected by a detector. The detected signal may be processed by processing equipment including, for example, digitizers, filters, decimators, interpolators, other suitable processing equipment, or any combination thereof. In some embodiments, the system may amplify the received signal using front end processor circuitry. The gain of the amplifier may be adjusted based on the emitted light brightness, historical information related to the brightness of prior received attenuated signals, other suitable information, or any combination thereof, so that the amplified signal matches the range of the analog-to-digital converter and thus increases resolution. In some embodiments, the system may account for the gain using hardware, software, or any combination thereof, such that the original intensity information is retained.

In step 2204, the system may calculate a second signal related to the first signal. For example, the system may calculate the derivative of the signal. In some embodiments, the system may calculate the second, third, fourth, or any other suitable derivative of the signal. The "derivative" is understood to be the rate of change of a signal, and n-th (where n is understood to represent a positive integer) derivatives are understood to be iterative applications of the derivative calculation. In some embodiments, the system may calculate an integral, moving average, any other suitable function, or any combination thereof. "Fiducials" are understood to represent points of interest that may correspond to features in a signal. Fiducials may be associated with zero crossings of the derivative of a signal.

In step 2206, the system may identify features of the second signal such as fiducials. In some embodiments, the system may identify zero crossings of the second signal. In some embodiments, the system may identify crossings of a non-zero threshold.

In step 2208, the system may correlate identified features of the second signal with the first signal. In some embodiments, when the second signal is the first derivative of the first signal, the system may correlate zero crossings of the second signal as local maxima and minima of the first signal. In some embodiments, where the second signal is the second derivative of the first signal, the system may correlate zero crossings of the second signal as inflection points of the first signal. The system may use higher order derivatives to identify other points in the first signal. In some embodiments, zero crossings of the second derivative may be associated with cardiovascular aging.

In some embodiments, a non-zero threshold crossing of the second signal may be used in determining cardiac cycle modulation (illustrated in FIG. 25 discussed below). For example, where the system desires to measure a feature located at the zero crossing of the second signal, it may turn on the light source when the signal is at some small, non-zero level such that the light source will be stabilized once the zero crossing is reached. Similarly, the system may use a subsequent non-zero crossing as a turn-off point.

In some embodiments, the system may use a photonic signal from a first light source to determine fiducials and other points of interest, and modulate a second light source based on the information determined using the first light source (e.g., using the method described by flow diagram 400 of FIG. 4). In some embodiments, the system may use fiducials and other points to modulate light drive signals, sampling rates, other suitable parameters, or any combination thereof.

It will be understood that the above identified algorithms for identifying fiducials and other points of interest are merely exemplary and that the system may use any suitable algorithm or technique, implemented in hardware, software, or any combination thereof.

Figure 23:
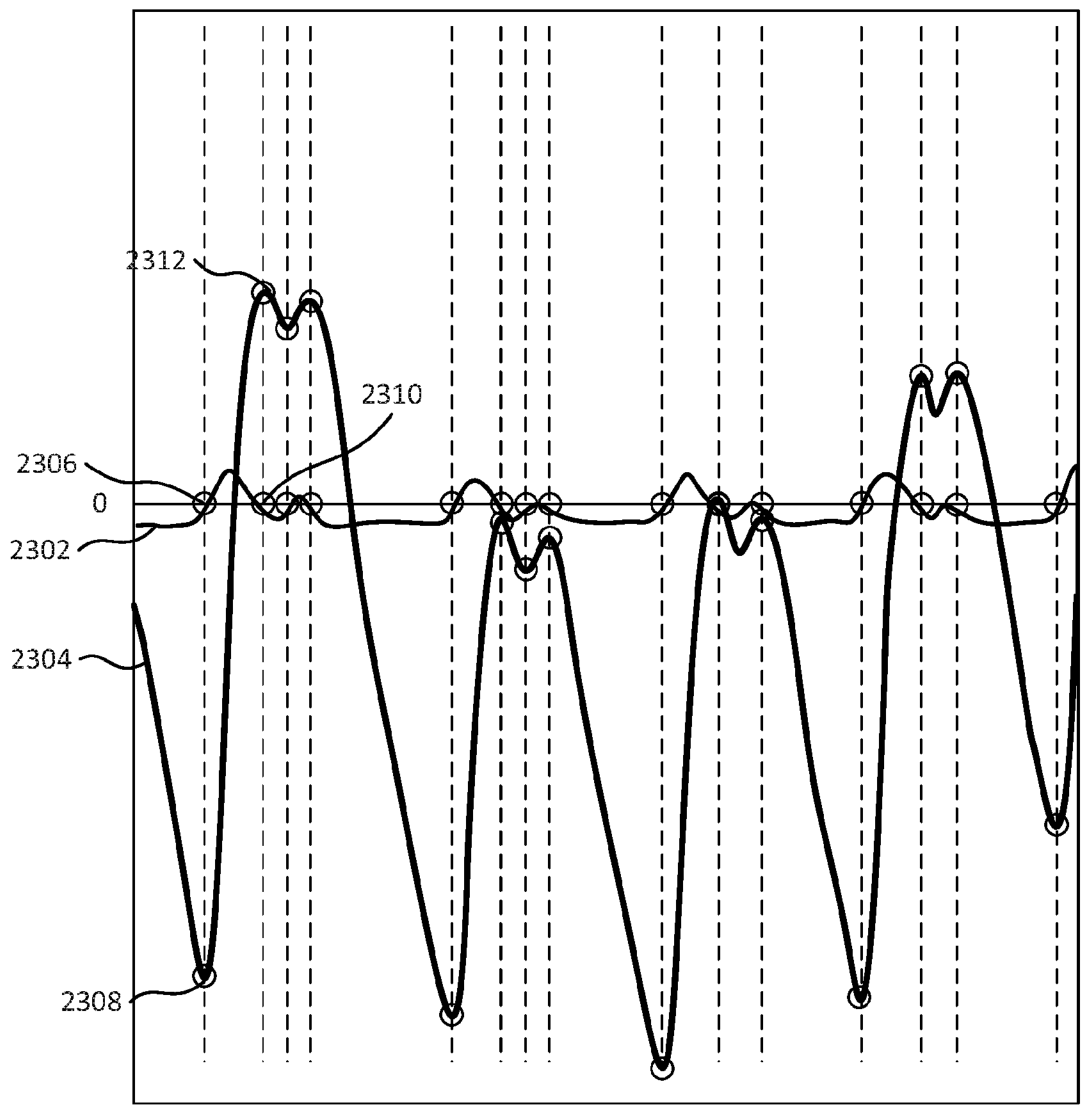
FIG. 23 is an illustrative plot of a waveform showing identification of fiducials in accordance with some embodiments of the present disclosure.

FIG. 23 is illustrative plot 2300 of a waveform showing identification of fiducials in accordance with some embodiments of the present disclosure. Plot 2300 may include waveform 2304 and first derivative 2302, where first derivative 2302 is determined by calculating the derivative of waveform 2304. Waveform 2304 may be the first signal of step 2202 of FIG. 22 and first derivative 2302 may be the second signal of step 2204. In some embodiments, zero crossings of the first derivative may be identified as fiducial points. Zero crossing 2306 of first derivative 2302 may be identified, for example, in step 2206 of FIG. 22. The system may identify local minimum 2308 of waveform 2302 in relation to zero crossing 2306. In some embodiments, the system may identify the negative-to-positive nature of zero crossing 2306 and thus identify local minimum 2308 as a minimum. Similarly, the system may identify the positiveto-negative nature of zero crossing 2310 and thus identify local maximum 2312 as a maximum.

Figure 24:
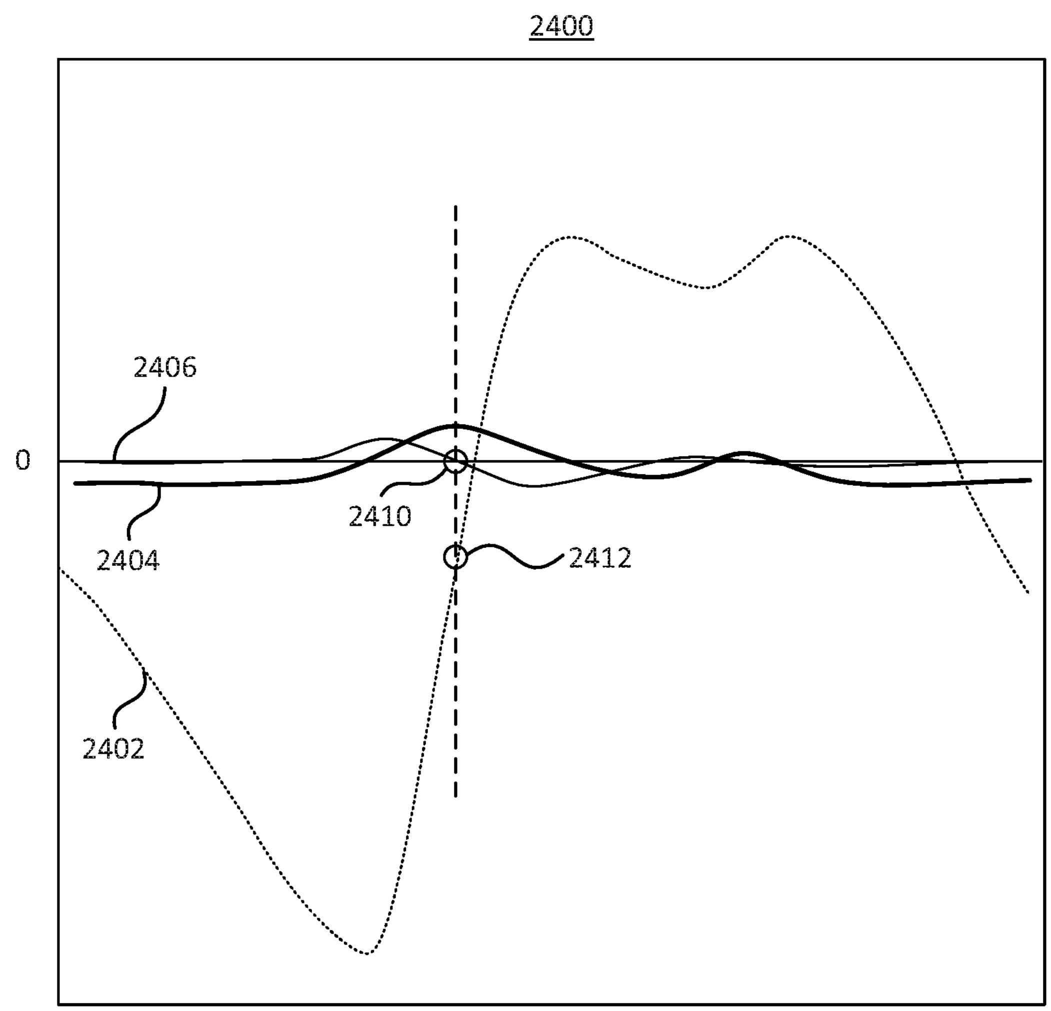
FIG. 24 is another illustrative plot of a waveform showing identification of fiducials in accordance with some embodiments of the present disclosure.

FIG. 24 is another illustrative plot 2400 of a waveform showing identification of fiducials in accordance with some embodiments of the present disclosure. In some embodiments, the system may identify the zero crossings of a second derivative and relate them to fiducial points on the received signal.

Plot 2400 may include waveform 2402, first derivative 2404 and second derivative 2406, where the first and second derivatives are derivatives of waveform 2402, as described above. In some embodiments, the system may identify the zero crossings of second derivative 2406. For example, second derivative 2406 may have a zero crossing at point 2410. The system may relate the position of point 2410 with point 2412 on waveform 2402. In some embodiments, the system may determine the amplitude of waveform 2402 at point 2412 and include that information in further processing of a physiological parameter. For example, information related to the zero crossings of second derivatives may be used in part in determining cardiovascular aging. In some embodiments, information from multiple derivatives may be combined. For example, when the first derivative is approaching zero, the second derivative may be used to estimate how quickly it will approach zero. In another example, when fiducial points are based on the second derivative, the third derivative may be used in part to determine the optical light drive signal.

Waveform 2402 may be the first signal of step 2202 of FIG. 22 and second derivative 2404 may be the second signal of step 2204. The zero crossings of the second derivative may be the features identified in step 2206.

Figure 25:
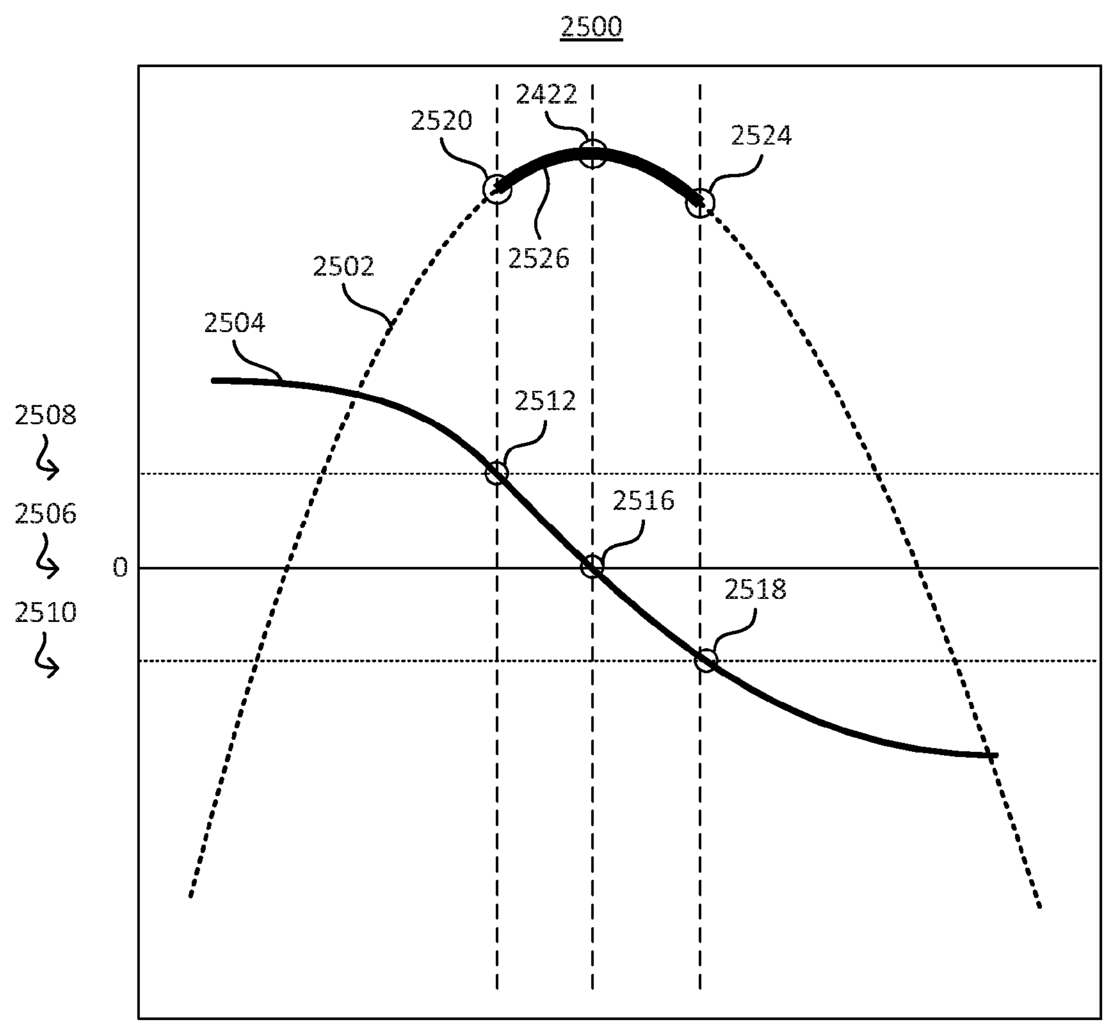
FIG. 25 is another illustrative plot of a waveform showing identification of fiducials in accordance with some embodiments of the present disclosure.

FIG. 25 is another illustrative plot 2500 of a waveform showing identification of fiducials in accordance with some embodiments of the present disclosure. In some embodiments, the system may use non-zero threshold crossings to identify a region of interest surrounding a fiducial or other point of interest. In some embodiments, the system may turn on a light source before a desired point of interest and turn off a light source following a point of interest so that the photonic signal can stabilize, so that the detector can stabilize, so that the processing equipment can obtain extra samples for averaging, interpolating, or decimating, for any other suitable reason, for amplifier gain adjustments to stabilize, or any combination thereof. In some embodiments, the system may use historical information from previous pulse cycles in determining thresholds. In some embodiments, the system may collect data without using cardiac cycle modulation until enough information is collected to determine thresholds and other alignment information for cardiac cycle modulation. In some embodiments, the system may adjust thresholds using historical information from previous cardiac cycle modulated pulse cycles. In some embodiments, the system may determine ensemble averages of previous pulse cycles. In some embodiments, the system may use multiple thresholds depending on the period of interest, the light source, the cardiac cycle modulation, the drive cycle modulation, convention servo algorithms, other suitable criteria, or any combination thereof. In some embodiments, the system may use the shape, slope, trend, derivatives, other suitable information, and any combination thereof, to determine parameters for cardiac cycle modulation (e.g., emitter brightness).

Plot 2500 may include waveform 2502 and derivative 2504. Thresholds may include zero threshold 2506, positive threshold 2508, and negative threshold 2510. In some embodiments, the positive and negative threshold offsets from zero may or may not be equal. In some embodiments, the offsets may be determined by user input, by predetermined values, by processing of previous data, by system settings related to the sensor and detector, by system settings related to the physiological parameter determined, by any other suitable parameters, or any combination thereof.

The system may identify threshold crossings of derivative 2504. For example, the system may identify positive threshold crossing 2512, zero threshold crossing 2516, and negative threshold crossing 2518. The system may use these points to determine light drive signals, to vary cardiac cycle modulation, to vary any other suitable parameters, or any combination thereof. The system may correlate threshold crossings with points on waveform 2502, for example, correlating positive threshold crossing 2512 with point 2520, zero threshold crossing 2516 with point 2422, and negative threshold crossing 2518 with point 2524. For example, in an embodiment described by flow diagram 400 of FIG. 4, where a second photonic signal is controlled using in part information determined by a first photonic signal, positive threshold crossing 2512 may be used as a turn on point for the second photonic signal and negative threshold crossing 2518 may be used as a turn off point for the second photonic signal. The system would thus sample waveform 2502 from point 2520 to 2524 (i.e., segment 2526) with, for example, the second photonic signal. In some embodiments, information related to threshold crossings may be used to determine other information related to waveform 2502. For example, the order of positive and negative threshold crossings of a first derivative may be used to identify a related zero crossing as a local maximum or minimum.

Figure 26:
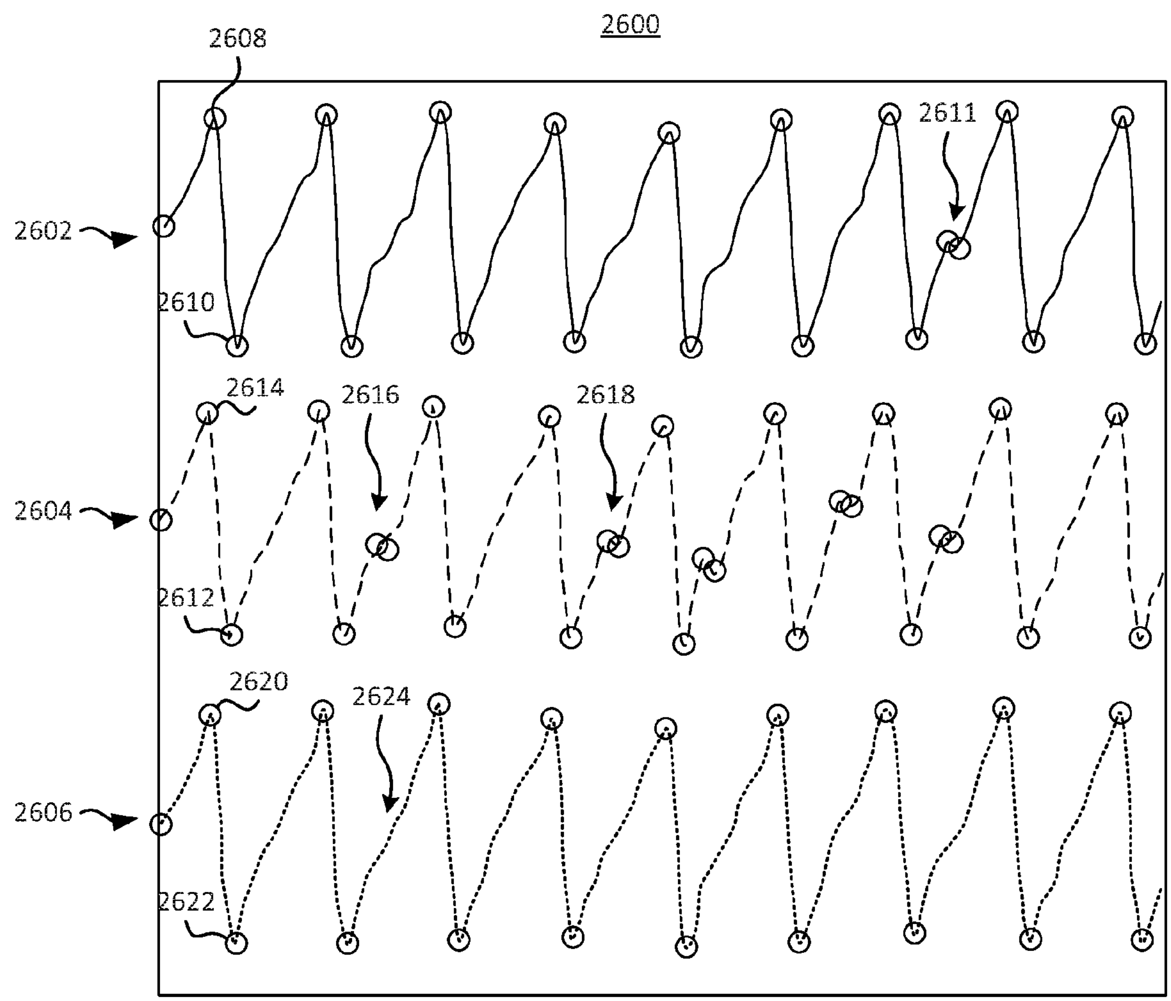
FIG. 26 is an illustrative plot of waveforms showing pulse identification in accordance with some embodiments of the present disclosure.

FIG. 26 is illustrative plot 2600 of waveforms showing pulse identification in accordance with some embodiments of the present disclosure. Plot 2600 may include PPG signal 2602, systole period modulated PPG signal 2604, and diastole period modulated PPG signal 2606. Plot 2600 may be shown with arbitrary units on the ordinate axis and time on the abscissa. The signals shown in plot 2600 are simulated sawtooth-shaped 60 BPM IR waveforms with a moderate amount of noise (e.g., Gaussian noise from approximately 0-5 Hz with amplitude independent of emitter output). The signals provide examples that illustrate when cardiac cycle modulation is properly selected, the accuracy of monitoring functions can be enhanced. The circles shown in plot 2600 indicate the occurrence of local minima and maxima using, for example, a roughly 150 ms window centered on each sample.

PPG signal 2602 may be representative of a PPG signal determined using a fixed power output throughout the cardiac cycle. Identified local maximum 2608 and local minimum 2610 are representative of a correctly identified peak and valley of physiological pulse in PPG signal 2602. The identified local maximum and minimum in region 2611 are representative of noise and do not correctly identify the peak and valley of a physiological pulse.

Systole period modulated PPG signal 2604 may be representative of a PPG signal determined using a cardiac cycle modulation, where the light source is modulated with a sinusoidal waveform that varies the brightness of the emitter from 50-150% of the mean. The peak emitter output is centered during the systole period of the cardiac cycle. For example, the light drive signal may drive an IR modulated LED using sinusoidal cardiac cycle modulation where peak LED output occurs during systole. In a further example, the cardiac cycle modulations may relate to cardiac cycle modulations illustrated in plot 500 of FIG. 5 and plot 1100 of FIG. 11. Identified local maximum 2614 and local minimum 2612 are representative of a correctly identified peak and valley of a physiological pulse. The identified maxima and minima in, for example, regions 2616 and 2618 are representative of noise and do not correctly identify the peak and valley of a physiological pulse. Because systole period modulated PPG signal 2604 uses lower power during the diastole portion of the cardiac cycle, noise may have a greater influence and cause spurious local maxima and minima to appear in the diastole portion of signal 2604. In some embodiments, the increased effect of noise during the diastole portions may reduce the accuracy or reliability of a pulse determination.

Diastole period modulated PPG signal 2606 may be representative of a PPG signal determined using a cardiac cycle modulation, where the light source is modulated with a sinusoidal waveform that varies the brightness of the emitter from 50-150% of the mean. The peak emitter output is centered during the diastole period of the cardiac cycle. For example, the light drive signal may drive an IR modulated LED using sinusoidal cardiac cycle modulation where peak LED output occurs during diastole. In a further example, the cardiac cycle modulations may relate to cardiac cycle modulations illustrated in plot 600 of FIG. 6 and plot 1000 of FIG. 10. Identified local maximum 2620 and local minimum 2622 are representative of a correctly identified peak and valley of a physiological pulse. Diastole period modulated PPG signal 2606, however, does not include any spurious local maxima and minima due to noise. For example, region 2624 of diastole period modulated PPG signal 2606 does not include a spurious local maximum and minimum whereas corresponding region 2616 of systole period modulated PPG signal 2604 includes a spurious local maximum and minimum.

In view of the foregoing, for pulse identification techniques in the presence of moderate noise, the diastole period cardiac cycle modulation technique may provide improved performance. For example, diastole period cardiac modulation may result in reduced identification of spurious pairs of incorrectly identified local maxima and minima.

Pulse amplitude and variations thereof are common calculations in physiological monitors. The simulated waveforms of plot 2600 of FIG. 26 may be used to calculate pulse amplitudes (i.e., the differences between maxima and minima). The calculations may be computed on the maxima and minima of correctly identified pulses. Based on this analysis, it may be determined that noise contributes coefficients of variation of 2.6%, 1.9%, and 3.8% to the computed pulse amplitudes of PPG signal 2602, systole period modulated PPG signal 2604, and diastole period modulated PPG signal 2606, respectively. Accordingly, for pulse amplitude calculation techniques in the presence of moderate noise, the systole period cardiac cycle modulation technique may provide improved performance.

Figure 27:
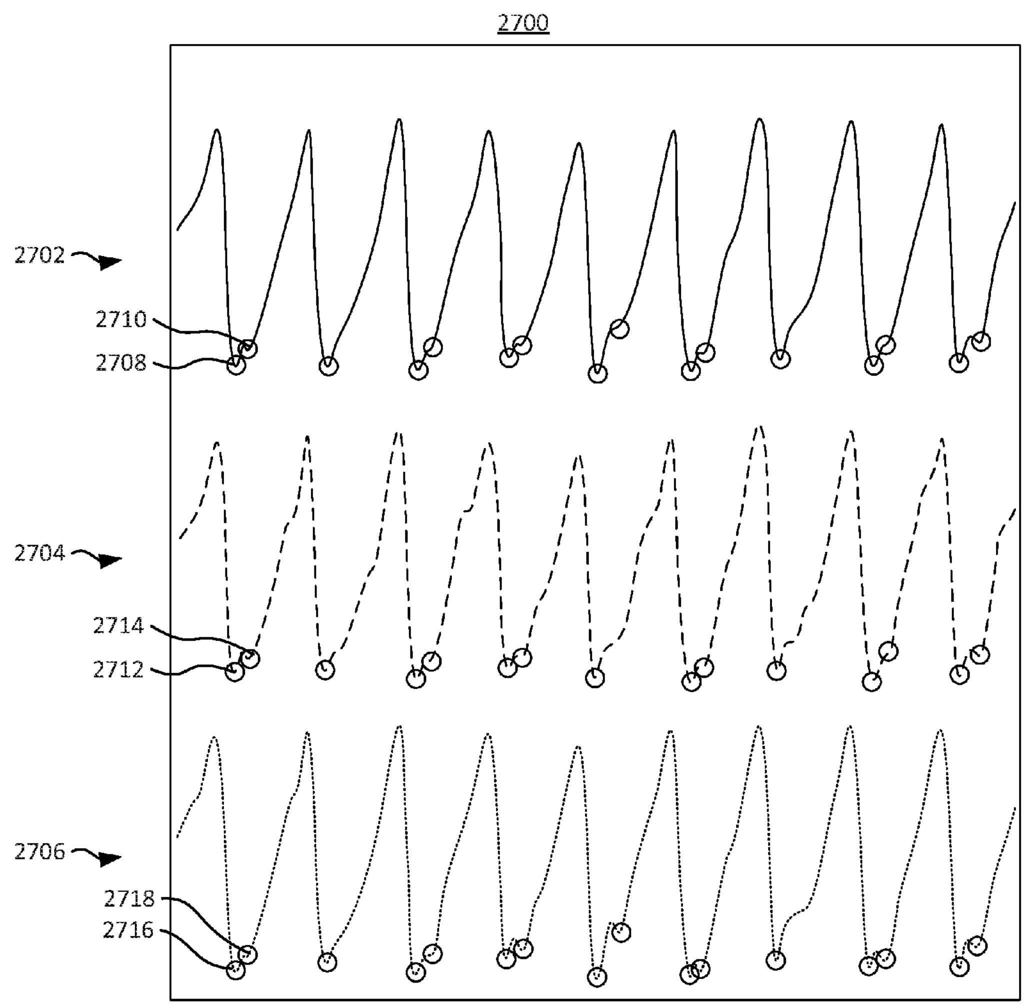
FIG. 27 is an illustrative plot of waveforms showing dicrotic notch identification in accordance with some embodiments of the present disclosure.

FIG. 27 is illustrative plot 2700 of waveforms showing dicrotic notch identification in accordance with some embodiments of the present disclosure. Plot 2700 may include PPG signal 2702, notch high modulated PPG signal 2704, and notch low modulated PPG signal 2706. "Notch high" will be understood to represent a cardiac cycle modulation technique where the light source brightness is relatively high during the dicrotic notch. "Notch low" will be understood to represent a cardiac cycle modulation technique where the light source brightness is relatively low during the dicrotic notch. For example, notch high modulated PPG signal 2704 may include a signal where the phase relationship between pulse and LED output has been shifted so that the maximum LED output is aligned with the occurrence of the dicrotic notch. In a further example, the notch low modulated PPG signal 2706 may include a signal where the phase relationship between pulse and LED output has been shifted so that the minimum LED output is aligned with the occurrence of the dicrotic notch. Phase relationships may be determined, for example, using information from prior pulse cycles. Plot 2700 may be shown with arbitrary units on the ordinate axis and time on the abscissa. The signals shown in plot 2700 are simulated sawtooth-shaped 60 BPM IR waveforms with a moderate amount of noise (e.g., Gaussian noise from approximately 0-5 Hz with amplitude independent of emitter output). The signals provide examples that illustrate when cardiac cycle modulation is properly selected, the accuracy of monitoring functions can be enhanced. The circles shown in plot 2700 indicate the occurrence of pulse minima and notch minima. Minima may be identified using any suitable processing technique. In some pulse cycles, pulse and or notch minima may be obscured by noise and not indicated.

PPG signal 2702 may be representative of a PPG signal determined using a fixed power output throughout the cardiac cycle. Identified pulse minimum 2708 and dicrotic notch minimum 2710 are representative of a correctly identified dicrotic notch in a physiological pulse in PPG signal 2702.

Notch high modulated PPG signal 2704 may be representative of a PPG signal determined using a cardiac cycle modulation, where the light source is modulated with a sinusoidal waveform that varies the brightness of the emitter from, for example, 50-150% of the mean. The peak emitter output is centered during the dicrotic notch period of the cardiac cycle. For example, the light drive signal may drive an IR modulated LED using sinusoidal cardiac cycle modulation where peak LED output occurs during the dicrotic notch. In a further example, the cardiac cycle modulations may relate to cardiac cycle modulations illustrated in plot 700 of FIG. 7 and plot 1200 of FIG. 12. Identified pulse minimum 2712 and dicrotic notch minimum 2714 are representative of a correctly identified dicrotic notch in a physiological pulse in notch high modulated PPG signal 2704.

Notch low modulated PPG signal 2706 may be representative of a PPG signal determined using a cardiac cycle modulation, where the light source is modulated with a sinusoidal waveform that varies the brightness of the emitter from, for example, 50-150% of the mean. The minimum emitter output is centered during the dicrotic notch of the cardiac cycle. For example, the light drive signal may drive an IR modulated LED using notch low cardiac cycle modulation where minimum LED output occurs during the dicrotic notch. In a further example, the cardiac cycle modulations may relate to cardiac cycle modulations illustrated in plot 700 of FIG. 7 where the "on" period of the red light drive signal is indicative of the cardiac cycle minimum, and plot 1200 of FIG. 12 where the "on" period of the light drive signal is indicative of the cardiac cycle minimum. Identified pulse minimum 2716 and dicrotic notch minimum 2718 are representative of a correctly identified dicrotic notch in a physiological pulse in notch high modulated PPG signal 2704. Because notch low period modulated PPG signal 2706 uses lower power during the dicrotic notch portion of the cardiac cycle, noise may have a greater influence on the detection of the pulse minimum and dicrotic notch minimum of notch low modulated PPG signal 2706. In some embodiments, the increased effect of noise during the dicrotic notch portions may reduce the accuracy or reliability of a pulse determination.

Dicrotic notch and variations thereof are common calculations in physiological monitors. Continuous non-invasive blood pressure measurements may be based on a differential pulse transit time. The differential pulse transit time may be based in part on the interval, magnitude, or interval and magnitude of the dicrotic notch, relative to the pulse minimum. The simulated waveforms of plot 2700 of FIG. 27 may be used to calculate the notch interval and magnitude (i.e., the differences between the pulse minimum and the dicrotic notch minimum). The calculations may be computed on the pulse minimum and notch minimum of correctly identified cycles. Based on this analysis, it may be determined that the notch interval standard deviation was 24 ms, 14 ms, and 32 ms for the computed dicrotic notches of PPG signal 2702, notch high modulated PPG signal 2704, and notch low modulated PPG signal 2706, respectively. It may be determined that the notch magnitude standard deviation was 4.0% of the pulse amplitude, 1.9% of the pulse amplitude, and 6.2% of the pulse amplitude for the computed dicrotic notches of PPG signal 2702, notch high modulated PPG signal 2704, and notch low modulated PPG signal 2706, respectively. Accordingly, for dicrotic notch related calculation techniques in the presence of moderate noise, the notch high cardiac cycle modulation technique may provide improved performance. In some embodiments, optimal cardiac cycle modulation for identification or analysis of the dicrotic notch may include a maximum output centered on the dicrotic notch, which may be slightly after the systole period. More generally, a modulation technique with a maximum emission centered on any pulse feature may increase the accuracy or reliability of that particular pulse feature.

Figure 28:
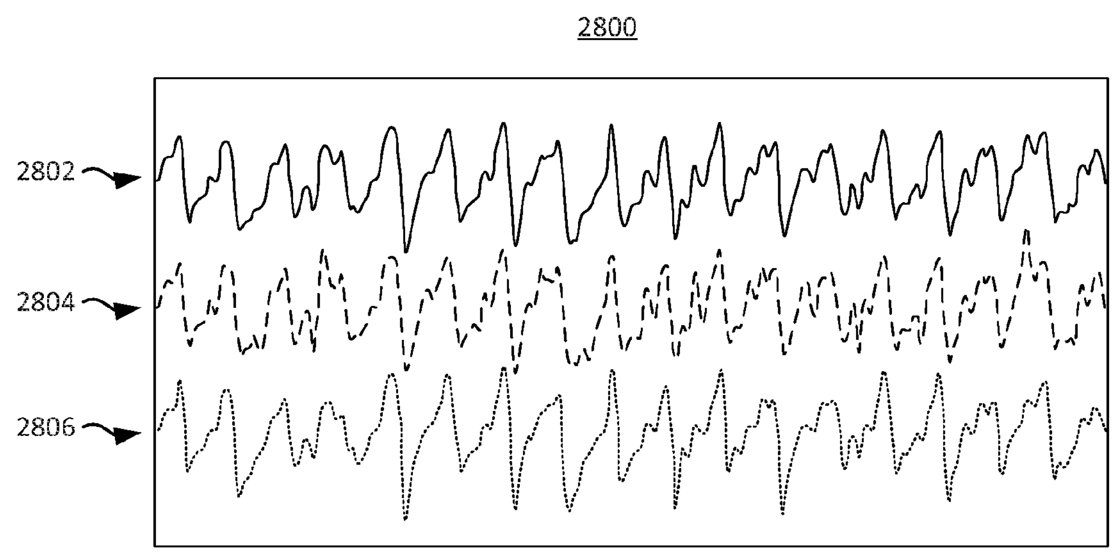
FIG. 28 is an illustrative plot of waveforms showing PPG signals in accordance with some embodiments of the present disclosure.

FIG. 28 is illustrative plot 2800 of waveforms showing PPG signals in accordance with some embodiments of the present disclosure. Plot 2800 may include PPG signal 2802, systole period modulated PPG signal 2804, and diastole period modulated PPG signal 2806. Plot 2800 may be shown with arbitrary units on the ordinate axis and time on the abscissa. The signals shown in plot 2800 are simulated sawtooth-shaped 60 BPM red waveforms with a moderate amount of noise (e.g., Gaussian noise from approximately 0-5 Hz with amplitude independent of emitter output). The red waveforms may be 25% of the intensity of the IR waveforms, as may occur in patients with dark skin pigmentation. As a result, the signals illustrated in FIG. 28 may have reduced signal quality as compared to, for example, plot 2600 of FIG. 26. The signals provide examples that illustrate that when cardiac cycle modulation is properly selected, the accuracy of monitoring functions can be enhanced.

Systole period modulated PPG signal 2804 may be representative of a PPG signal determined using a cardiac cycle modulation, where the light source is modulated with a sinusoidal waveform that varies the brightness of the emitter from 50-150% of the mean. The peak emitter output is centered during the systole period of the cardiac cycle. For example, the light drive signal may drive a red modulated LED using sinusoidal cardiac cycle modulation where peak LED output occurs during systole. In a further example, the cardiac cycle modulations may relate to cardiac cycle modulations illustrated in plot 1100 of FIG. 11.

Diastole period modulated PPG signal 2806 may be representative of a PPG signal determined using a cardiac cycle modulation, where the light source is modulated with a sinusoidal waveform that varies the brightness of the emitter from 50-150% of the mean. The peak emitter output is centered during the diastole period of the cardiac cycle. For example, the light drive signal may drive red modulated LEDs using sinusoidal cardiac cycle modulation where peak LED output occurs during diastole. In a further example, the cardiac cycle modulations may relate to cardiac cycle modulations illustrated in plot 1000 of FIG. 10.

Ratio-of-ratio calculations are common calculations in pulse oximeters. Ratio-of-ratio calculations may use IR and red (or some other combination of wavelengths) to determine oxygen saturation. The calculation may include wavelength-dependent and empirically determined calibration factors. The ratio-of-ratio calculation term may be approximated as:

$$\frac{\left(\frac{Red_{max} - Red_{min}}{Red_{mean}}\right)}{\left(\frac{IR_{max} - IR_{min}}{IR_{mean}}\right)}$$

where terms relate to the maximum, minimum, and mean amplitudes of the associated signals. In some embodiments, the term may be calculated for each pulse cycle.

The simulated waveforms of plot 2800 of FIG. 28 may be used to calculate the ratio-of-ratios. The ratio-of-ratios term for the signals of plot 2800, in the absence of noise may be 1.0 for each pulse cycle. Based on the analysis of illustrated signals with included noise, it may be determined that the mean ratio-of-ratios term is 1.013 with a standard deviation of 0.243, 0.995 with a standard deviation of 0.164, and 1.103 with a standard deviation of 0.511 for the computed pulse cycles of PPG signal 2802, systole period modulated PPG signal 2804, and diastole period modulated PPG signal 2806, respectively. Accordingly, for ratio-of-ratios calculation techniques in the presence of moderate noise, the systole period cardiac cycle modulation technique may provide improved performance.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed:

1. A method of operating a pulse oximeter, the method comprising:

receiving, using the pulse oximeter, a photoplethysmograph (PPG) signal from a pulse oximetry sensor, which comprises a light source and a detector;

determining, using the pulse oximeter, pulse period information related to physiological pulses in the PPG signal;

determining, using the pulse oximeter, at least one parameter of a light drive signal based on the pulse period information, wherein the at least one parameter is determined to vary substantially synchronously with the physiological pulses, and wherein the determined at least one parameter comprises at least one of light intensity, light source firing rate, and duty cycle; and generating, using the pulse oximeter, the light drive signal for activating the light source of the pulse oximetry sensor to emit a photonic signal according to the determined at least one parameter.

2. The method of claim 1, wherein the determined at least one parameter comprises the light intensity.

3. The method of claim 2, wherein the light intensity comprises a high value and a low value, and wherein the light intensity is varied so that the high value coincides with at least one of a systole period, a diastole period, a dicrotic notch, a peak, and a trough of the physiological pulses.

4. The method of claim 3, wherein the light intensity is varied according to a periodic waveform, wherein the periodic waveform comprises a plurality of peaks, and wherein the peaks are configured to coincide with at least one of a systole period, a diastole period, a dicrotic notch, a peak, and a trough of the physiological pulses.

5. The method of claim 1, wherein the determined at least one parameter comprises the light source firing rate.

6. The method of claim 5, wherein the light source firing rate comprises a high value and a low value, and wherein the light source firing rate is varied so that the high value coincides with at least one of a systole period, a diastole period, a dicrotic notch, a peak, and a trough of the physiological pulses.

7. The method of claim 6, wherein the light source firing rate is varied according to a periodic waveform, wherein the periodic waveform comprises a plurality peaks, and wherein the peaks are configured to coincide with at least one of a systole period, a diastole period, a dicrotic notch, a peak, and a trough of the physiological pulses.

8. The method of claim 1, further comprising:

determining, using the pulse oximeter, a sampling rate of an analog-to-digital converter of the pulse oximeter based on the pulse period information, wherein the sampling rate is determined to vary substantially synchronously with the physiological pulses in the PPG signal; and sampling, using the analog-to-digital converter of the pulse oximeter, the PPG signal according to the determined sampling rate.

9. The method of claim 1, wherein the determined at least one parameter comprises the duty cycle.

10. The method of claim 9, wherein the duty cycle comprises a high value corresponding to a longer duty cycle and a low value corresponding to a shorter duty cycle, and wherein the duty cycle is varied so that the high value coincides with at least one of a systole period, a diastole period, a dicrotic notch, a peak, and a trough of the physiological pulses.

11. The method of claim 10, wherein the duty cycle is varied according to a periodic waveform, wherein the periodic waveform comprises a plurality of peaks, and wherein the peaks are configured to coincide with at least one of a systole period, a diastole period, a dicrotic notch, a peak, and a trough of the physiological pulses.

12. The method of claim 1, wherein the physiological pulses of the subject comprise one of cardiac pulses and respiratory pulses.

13. The method of claim 1, wherein the light source comprises at least two emitters and wherein the light drive signal is configured to activate the at least two emitters.

14. The method of claim 13, the wherein the at least one parameter is determined to vary for each of the at least two emitters.

15. The method of claim 1, further comprising receiving an external trigger, wherein the at least one parameter is further determined based on the external trigger.

16. The method of claim 1, further comprising:

receiving, using the pulse oximeter, a subsequent portion of the PPG signal that is generated based on the light source being activated by the light drive signal; and determining, using the pulse oximeter, at least one of pulse rate and oxygen saturation of the subject based on the subsequent portion of the PPG signal.

17. A method of claim 1, wherein the pulse period information comprises at least one pulse period of the physiological pulses.

18. The method of claim 17, wherein the physiological pulses comprise at least one period of interest and wherein the at least one parameter of the light drive signal is determined to increase power during the at least one period of interest.

19. The method of claim 18, wherein the at least one parameter of the light drive signal is determined to increase power based on when the period of interest occurred in a prior physiological pulse and based on the at least one determined pulse period.

20. The method of claim 19, wherein the at least one parameter of the light drive signal is determined to increase power further based on a time offset.

21. The method of claim 20, wherein the pulse period information further comprises a standard deviation of pulse periods of the physiological pulses and wherein the time offset is determined based on the standard deviation.

* * * * *